United States Patent
TeKoppele et al.

(10) Patent No.: US 6,733,988 B1
(45) Date of Patent: May 11, 2004

(54) INHIBITION OF TELOPEPTIDE LYSYL HYDROXYLASE ACTIVITY OR PRODUCTION AS ANTI-FIBROTIC THERAPY

(75) Inventors: Johannes Maria TeKoppele, Leiderdorp (NL); Rudolf Antonius Bank, Hoofddorp (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 09/450,209

(22) Filed: Nov. 29, 1999

(51) Int. Cl.$^7$ .............................. C12P 21/06; C12N 9/02
(52) U.S. Cl. ....................................... 435/68.1; 435/184
(58) Field of Search ................................. 435/189, 944, 435/68.1; 530/356

(56) References Cited

PUBLICATIONS

Valtavaara, M., et al. (1997) J. Biol. Chem. 272(11), 6831–6834.*
R.A. Bank et al.; Defective Collagen Crosslinking in Bone, but not in Ligament or Cartilage, in Bruck Syndrome: Indications for a Bone–specific Telopeptide Lysyl Hydroxylase on Chromosome 17; Proc. Natl.Acad.Sci. USA vol. 96, Feb. 1999, pp. 1054–1058.
R.A. Bank et al.; The Molecular Defect in Bruck Syndrome: Evidence for Tissue–Specific Telopeptide Lysyl Hydroxylases; Official Journal of the International Bone and Mineral Society; 1998 Program and Abstracts from Second Joint Meeting; SA066, p. S543.
R.J. Fernandes et al.; Post–Translational Overmodification of Collagen Expressed by SAOS–2–Osteoblast–like Cells; 44th Annual Meeting, Orthopaedic Research Society, Mar. 16–19, 1998, p. 933.
R.A. Banks et al.; The Bruck Syndrome Evidence for Tissue–Specific Telopeptidyl Lysy; Hydroxylases; 44th Annual Meeting, Orthopaedic Research Society, Mar. 16–19, 1998; p. 324.
R. Myllylä et al.; Molecular Cloning of Chick Lysyl Hyydroxylase; The Journal of Biological Chemistry, vol. 266, No. 5, Feb., 15, 1991; pp. 2805–2810.
R. Myllylä et al.; Ascorbate Is Consumed Stoichimetrically in the Uncoupled Reactions Catalyzed by Prolyl 4–Hydroxylase and Lysyl Hydroxylase; The Journal of Biological Chemistry, vol. 259, No. 9, May 10, 1984, pp. 5403–5405.
J. Brinckmann et al.; Ehlers–Danlos Syndrome Type VI: Lysyl Hydroxylase Deficiency Due to a Novel Point Mutation (W612C), Arch Dermatol Res (1998) vol. 290; pp. 181–186.
K. Majamaa et al.; Differences Between Collagen Hydroxylases and 2–oxogutarate Dehydrogenase in their Inhibition by Structural Analogues of 2–oxoglutarate; Biochem. J. (1985) vol. 229; pp. 127–133.
K. Kivirikko et al.; Recent Development in Posttranslational Modification: Intracellular Processing; Methods in Enzymology, vol. 144, 1987, pp. 96–114.
M.J. Barnes et al.; Hydroxylysine in the N–Terminal Telopeptides of Skin Collagen from Chick Embryo and Newbnorn Rat; Biochem. J. (1971) vol. 125; pp. 925–928.
M.J. Barnes et al.; Hydroxylysine in the N–Terminal Regions of $\alpha_1$ and $\alpha_2$–Chains of Various Collagens; Biochem. J., vol. 125, 1971; pp. 433–437.
R. Myllylä et al.; Modification of Vertebrate and Algal Prolyl 4–Hydroxylases and Vertebrate Lysyl Hydroxylase by Diethyl Pyrocarbonate; Biochem. J. vol. 286, 1992, pp. 923–927.
P.M. Royce et al.; Failure of Highly Purified Lysyl Hydroxylase to Hydroxylate Lysyl Residues in the Non–Helical Regions of Collagen; Biochem. J. vol. 230, 1985, pp. 475–480.
L. Risteli et al.; Preferential Hydroxylation of Type IV Collegen by Lysyl Hydroxylase from Ehlers–Danlos Syndrome Type VI Fibroblasts; Biochemical and Biophysical Research Communications, vol. 96, No. 4 1980, Oct. 31, 1980, pp. 1778–1784.
A. Ihme et al.; Ehlers–Danlos Syndrome Type VI: Collagen Type Specificity of Defective Lysyl Hydroxylation in Various Tissues; The Journal of Investigative Dermatology vol. 83, No. 3, 1984, pp. 161–165.
J. Chang et al.; Urinary Pyridinoline Cross–links in Ehlers–Danlos Syndrome Type VI; Am. J. Hum. Genet. vol. 57, 1995, pp. 1505–1508.

(List continued on next page.)

*Primary Examiner*—Charles L. Patterson, Jr.
(74) *Attorney, Agent, or Firm*—Norris McLaughlin & Marcus

(57) ABSTRACT

The invention uses the existence of tissue-specific telopeptide lysyl hydroxylases, enzymes that hydroxylate lysine residues of the telopeptides of collagen, and the discovery that collagen molecules cross-linked by hydroxyallysine (derived from telopeptide hydroxylysine) are less susceptible to degradation/turnover than collagen molecules cross-linked by means of allysine (derived from telopeptide lysine) due to a different intrafibrillar packing of said collagen molecules. Further, the invention contemplates that one of the characteristics of collagen in scars and other fibrotic tissues is an increase in hydroxyallysine derived cross-links (making the collagen less susceptible to proteolytic breakdown), that this increase in hydroxyallysine cross-links is due to increased levels of telopeptide lysyl hydroxylase, and that telopeptide lysyl hydroxylase plays an important role in the excessive accumulation of collagen in fibrosis/scarring. Still further, the invention relates to methods using said knowledge for the treatment of fibrosis/scarring by inhibiting telopeptide lysyl hydroxylase activity or inhibiting telopeptide lysyl hydroxylase translation/transcription in order to decrease selectively hydroxyallysine cross-links (leaving the allysine cross-link route intact).

8 Claims, 13 Drawing Sheets

OTHER PUBLICATIONS

H.N. Yeowell et al.; Sequence Analysis of a cDNA for Lysyl Hydroxylase Isolated from Human Skin Fibroblasts from a Normal Donor: Differences from Human Placental Lysyl Hydroxylase cDNA; J. F Investigative Dermatology, Inc. 0022–202X/94/S07.00 1994, pp. 382–384.

S. Murad et al.; Structure–Activity Relationship of Minoxidil Analogs as Inhibitors of Lysyl Hydroxylase in Cultured Fibroblasts; Archives of Biochemistry and Biophysics, vol. 292, No. 1, Jan. 1992, pp. 234–238.

J. Hanada et al.; Inhibition of Cultured Human RPE Cell Proliferation and Lysyl Hydroxylase Activity in Hydroxy Derivatives of Minoxidil; Investigative Ophthalmology & Visual Science, vol. 35, No. 2, Feb. 1994, pp. 463–469.

J. Handa et al.; Minoxidil Inhibits Ocular Cell Proliferation and Lysyl Hydroxylase Activity; Investigative Ophithalmology & Visual Science, vol. 34, No. 3 Mar. 1993, pp. 567–575.

T. Hautala et al.; Minoxidil Specifically Decreases the Expression of Lysine Hydroxylase in Cultured Human Skin Fibroblasts; Biochem. J. vol. 283, 1992, pp. 51–54.

K. Passoja et al.; Identifiacation of Arginine–700 as the Residue That Binds the C–5 Carboxyl Group of 2–Oxoglutarate in Human Lysyl Hydroxylase 1; Federation of European Biochemical Societies Letters 434, 1998, pp. 145–148.

T. Hautala et al.; Cloning of Human Lysyl Hydroxylase: Complete cDNA–Derived Amino Acid Sequence and Assignment of the Gene (PLOD) to Chromosome 1p36.6–p36.2; Genomics 13, 1992, pp. 62–69.

K. Passoja et al.; Cloning and Characterization of a Third Human Lysyl Hydroxylase Isoform; Proc. Natl. Acad. Sci, USA, vol. 95, Sep. 1998, pp. 10482–10486.

M. Valtavaara et al.; Cloning and Characterization of a Novel Human Lysyl Hydroxylase Isoform Highly Expressed in Pancreas and Muscle; The Journal of Biological Chemistry, vol. 272, No. 11, Mar. 14, 1997, pp. 6831–6834.

A. Pirskanen et al.; Site–directed Mutagenesis of Human Lysyl Hydroxylase Expressed in Insect Cells; The Journal of Biologifal Chemistry, vol. 271, No. 16, Apr. 19, 1996, pp. 9398–9402.

M. Valtavaara et al.; Primary Structure, Tissue Distributrion, and Chromosomal Localization of a Novel Isoform of Lysyl Hydroxylase (Lysyl Hydroxylase 3); The Journal of Biological Chemistry, vol. 273, No. 21, MAy 22, 1998, pp. 12881–12886.

B. Krol et al.; The Expression of a Functional, Secreted Human Lysyl Hydroxylase in a Baculovirus System; J. of Investigative Dermatology, Inc., vol. 106 1996, pp. 11–16.

J. Gerriets et al.; Tendon Hypertrophy is Associated witH Increased Hydroxylation of Nonhelical Lysine Residues at Two Specific Cross–linking Sites in Type I Collagen; The Journal of Biological Chemistry, vol. 268, No. 34, Dec. 5, 1993, pp. 25553–255560.

L. Forrest et al.; A Comparison Between the Reducible Intermolecular Crosslinks of the Collagens from Mature Dermis and Young Dermal Scar Tissue of the Guinea Pig; Biochemical and Biophysical Research Communications, vol. 46, No. 5, 1972, pp. 1776–1781.

D. Cannon et al.; Collagen Cross–linking in Corneal Scar Formation; Biochimica et Biophysica Acta. 412 (1975) pp. 18–25.

K. Reiser et al.; A Molecular Marker for Fibrotic Collagen in Lungs of Infants with Respiratory Distress Syndrome; Biochemical Medicine and Metabolic Biology, vol. 37, 1987; pp. 16–21.

J. Last et al.; Hydroxylation of Collagen by Lungs of Rats Administered Bleomycin; American Journal of Respiratory Cell and Molecular Biology, vol. 2, 1990, pp. 543–548.

J. Last et al.; Collagen Cross–linking in Adult Patients with Acute and Chronic Fibrotic Lung Disease; Department of Internal Medicine, School of Medicine and California Primate Research Center, University of California, et al.; Mar. 14, 1989, pp. 307–313.

T. Morigunchi et al.; Crosslink of Collagen in Hypertrophic Scar; The Journal of Investigative Dermatology, vol. 72, 1979, pp. 143–145.

S. Ricard–Blum et al.; Mechanism of Collagen Network Stabilization in Human Irreversible Granulomatous Liver Fibrosis; Gastroenterology, vol. 111, 1996, pp. 172–182.

A. Bailey et al.; Intermolecular Cross–linking in Fibrotic Collagen; AFRC Food Research Institute; 1985 Fibrosis pp. 80–86.

K. Uzawa et al.; Altered Posttranslational Modifications of collagen in Keloid; Biochemical and Biophysical Research Communications, vol. 249, 1998, pp. 652–655.

S. Ricard–Blum et al.; Hydroxypyridinium Collagen Cross–links in Human Liver Fibrosis: Study of Alveolar Echinococcosis; Hepatology, 15 1991, pp. 599–602.

J. Gerriets et al.; Lung Collagen Cross–links in Rats with Experimentally Induced Pulmonary Fibrosis; Biochimica et Biophysica Acta, vol. 1316. 1996, pp. 121–131.

J. Brinckman et al.; Altered X–ray Diffraction Pattern is Accompanied by a Change in the Mode of Cross–link Formation in Lipodermatosclerosis; J. of Investigative Dermatology, Inc., 107, 1996, pp. 589–592.

L. Knott et al.; Collagen Cross–links in Mineralizing Tissues: A Review of Their Chemistry, Function, and Clinical Relevance; Elsevier, Bone vol. 22, No. 3, Mar. 1998, pp. 181–187.

M. Pasquali et al.; Abnormal Formation of Collagen Cross–links in Skin Fibroblasts Cultures from Patients with Ehlers–Danlos Syndrome Type VI; Proceedings of the Association of American Physicans, vol. 109, No. 1, pp. 33–41.

S. Ricard–Blum et al.; *Pyridinoline*, a Mature Collagen Cross–link, in Fibrotic Livers from *Schistosoma Mansoni*–Infected Mice; Am. J. Trop. Med. Hyg., No. 47 (6), 1992, pp. 816–820.

S. Richard–Blum et al.; Covalent Cross–linking of Liver Collagen by Pyridinoline Increases in the Course of Expermental Alveolar Echinococcosis; Parasite, vol. 2 1995, pp. 113–118.

S. Ricard–Blum et al.; The Level of the Collagen Cross–link Pyridinoline Reflects the Improvement of Cutaneous in One Case of Skin Aleveolar Echinococcosis; Parasitol Res, 1998, vol. 84, pp. 715–719.

S. Ricard–Blum et al.; Collagen Cross–linking by Pyridinoline Occurs in Non–reversible Skin Fibrosis; Cellular And Molecular Biology vol. 39 7), 1993, pp. 723–727.

K. Uzawa et al.; Differential Expression of Human Lysyl Hydroxylase Genes, Lysine Hydroxylation, and Cross–linking of Type I Collagen During Osteoblastic Differentiation in Vitro; Journal of Bone and Mineral Research; vol. 14, No. 8, 1999, pp. 1272–1280.

S. Robins; Fibrillogenesis and Maturation of Collagens; Dynamics of Bone and Cartliage Metabolism, 1999 Academic Press; pp. 31–42.

J. Last et al.; Biosynthesis of Collagen Crosslinks. III. In Vivo Labeling and Stability of Lung Collagen in Rats with Bleomycin–induced Pulmonary Fibrosis; American Journal of Respiratory Cell and Molecular Biology, vol. 1, 1989, pp. 111–117.

K. Reiser et al.; Changes in Collagen Cross–linking in Bleomycin–induced Pulmonary Fibrosis; Journal of Biochemical Toxicology 1, 1986, pp. 83–91.

* cited by examiner-

FIGURE 9A

SEQUENCE HUMAN PLOD1, PLOD2 and PLOD3

```
PLOD1  *  *  *  *  *  *  *  *  *  *  M  R  P  L  L  L  A  L  L
PLOD2  M  G  G  C  T  V  K  P  Q  L  L  L  L  A  L  V  L  H  P  W  N
PLOD3  M  T  S  S  G  P  G  P  R  F  L  L  L  L  P  L  L  L  P  P  A
PLOD1  **********************************atgcggcccctgctgctactggccctgctg
PLOD2  atggggggatgcacggtgaagcctcagctgctgctcctggcgctcgtcctccaccoctggaat
PLOD3  atgacctcctcggggcctggaccccggttcctgctgctgctgccgctgctgctgcccctgcg PLOD1  G  W  L  L  L  A  E  A  K  G  D  A  K  P  E  D  N  L  L  V  L
PLOD2  P  C  L  G  A  D  S  E  K  P  S  S  I  P  T  D  K  L  L  V  I
PLOD3  A  S  A  S  D  R  P  R  G  R  D  P  V  N  P  E  K  L  L  V  I
PLOD1  ggctggctgctgctggccgaagcgaagggcgacgccaagccggaggacaaccttttagtcctc
PLOD2  ccctgtctgggtgcggactcggagaagccctcgagcatccccacagataaattattagtcata
PLOD3  gcctcagcctccgaccggccccggggccgagacccggtcaacccagagaagctgctggtgatc PLOD1  T  V  A  T  K  E  T  E  G  F  R  R  F  K  R  S  A  Q  F  N
PLOD2  T  V  A  T  K  E  S  D  G  F  H  R  F  M  Q  S  A  K  Y  F  N
PLOD3  T  V  A  T  A  E  T  E  G  Y  L  R  F  L  R  S  A  E  F  F  N
PLOD1  acggtggccactaaggagaccgagggattccgtcgcttcaagcgctcagctcagttcttcaac
PLOD2  actgtagcaacaaaagaaagtgatggattccatcgatttatgcagtcagccaaatatttcaat
PLOD3  actgtggccacagctgaaaccgaggggtacctgcgtttcctgcgctctgcggagttcttcaac PLOD1  Y  K  I  Q  A  L  G  L  G  E  D  W  N  V  E  K  G  T  *  S  A
PLOD2  Y  T  V  K  V  L  G  Q  G  E  E  W  R  G  G  D  G  I  N  S  I
PLOD3  Y  T  V  R  T  L  G  L  G  E  E  W  R  G  G  D  V  A  R  T  V
PLOD1  tacaagatccaggcgcttggcctaggggaggactggaatgtggagaagggggacg***tcggca
PLOD2  tatactgtgaaggtccttggtcaaggagaagaatggagaggtggtgatggaattaatagtatt
PLOD3  tacactgtgcggaccctgggcctgggagaggagtggcgaggggggtgatgtggctcgaacagtt PLOD1  G  G  G  Q  K  V  R  L  L  K  K  A  L  E  K  H  A  D  K  E  D
PLOD2  G  G  G  Q  K  V  R  L  M  K  E  V  M  E  H  Y  A  D  Q  D  D
PLOD3  G  G  G  Q  K  V  R  W  L  K  K  E  M  E  K  Y  A  D  R  E  D
PLOD1  ggtggagggcagaaggtccggctgctgaagaaagctctggagaagcacgcagacaaggaggat
PLOD2  ggaggggggccagaaagtgagattaatgaaagaagtcatggaacactatgctgatcaagatgat
PLOD3  ggtggaggacagaaggtccggtggttaaagaaggaaatggagaaatacgctgaccgggaggat PLOD1  L  V  I  L  F  T  D  S  Y  D  V  L  F  A  S  G  P  R  E  L  L
PLOD2  L  V  V  M  F  T  E  C  F  D  V  I  F  A  G  G  P  E  E  V  L
PLOD3  M  I  I  M  F  V  D  S  Y  D  V  I  L  A  G  S  P  T  E  L  L
PLOD1  ctggtcattctcttcacagacagctatgacgtgctgtttgcatcggggccccgggagctcctg
PLOD2  ctggttgtcatgtttactgaatgctttgatgtcatatttgctggtggtccagaagaagttcta
PLOD3  atgatcatcatgtttgtggatagctacgacgtgattctggccggcagccccacagagctgctg PLOD1  K  K  F  R  Q  A  R  S  Q  V  V  F  S  A  E  E  L  I  Y  P  D
PLOD2  K  K  F  Q  K  A  N  H  K  V  V  F  A  A  D  G  I  L  W  P  D
PLOD3  K  K  F  V  Q  S  G  S  R  L  L  F  S  A  E  S  F  C  W  P  E
PLOD1  aagaagttccggcaggccaggagccaggtggtcttctctgctgaggagctcatctacccagac
PLOD2  aaaaaattccaaaaggcaaaccacaaagtggtctttgcagcagatggaattttgtggccagat
PLOD3  aagaagttcgtccagagtggcagccgcctgctcttctctgcagagagcttctgctggcccgag PLOD1  R  R  L  E  T  K  Y  P  V  V  S  D  G  K  R  F  L  G  S  G  G
PLOD2  K  R  L  A  D  K  Y  P  V  V  H  I  G  K  R  Y  L  N  S  G  G
PLOD3  W  G  L  A  E  Q  Y  P  E  V  G  T  G  K  R  F  L  N  S  G  G
PLOD1  cgcaggctggagaccaagtatccggtggtgtccgatggcaagaggttcctgggctctggaggc
PLOD2  aaaagactagcagacaagtatcctgttgtgcacattgggaaacgctatctgaattcaggagga
PLOD3  tgggggctggcggagcagtaccctgaggtgggcacggggaagcgcttcctcaattctggtgga PLOD1  F  I  G  Y  A  P  N  L  S  K  L  V  A  E  W  E  G  Q  D  S  D
PLOD2  F  I  G  Y  A  P  Y  V  N  R  I  V  Q  Q  W  N  L  Q  D  N  D
PLOD3  F  I  G  F  A  T  T  I  H  Q  I  V  R  Q  W  K  Y  D  D  D
PLOD1  ttcatcggttatgcccccaacctcagcaaactggtggccgagtgggagggccaggacagcgac
PLOD2  tttattggctatgctccatatgtcaaccgtatagttcaacaatggaatctccaggataatgat
PLOD3  ttcatcggttttgccaccaccatccaccaaatcgtgcgccagtggaagtacaaggatgatgac
```

FIGURE 9B

```
PLOD1 S D Q L F Y T K I F L D P E K R E Q I N I
PLOD2 D D Q L F Y T K V Y I D P L K R E A I N I
PLOD3 D D Q L F Y T R L Y L D P G L R E K L S L
PLOD1 agcgatcagctgttttacaccaagatcttcttggacccggagaagagggagcagatcaatatc
PLOD2 gatgatcagctcttttacactaaagtttacattgatccactgaaaagggaagctattaacatc
PLOD3 gacgaccagctgttctacacacggctctacctggacccaggactgagggagaaactcagcctt PLOD1 T L D H R C R I F Q N L D G A L D E V V L
PLOD2 T L D H K C K I F Q T L N G A V D E V V L
PLOD3 N L D H K S R I F Q N L N G A L D E V V L
PLOD1 accctggaccaccgctgccgtatcttccagaacctggatggagccttggatgaggtcgtgctc
PLOD2 acattggatcacaaatgcaaaatttccagaccttaaatggagctgtagatgaagttgtttta
PLOD3 aatctggatcataagtctcggatctttcagaacctcaacggggctttagatgaagtggtttta PLOD1 K F E M G H V R A R N L A Y D T L P V L I
PLOD2 K F E N G K A R A K N T F Y E T L P V A I
PLOD3 K F D R N R V R I R N V A Y D T L P I V V
PLOD1 aagtttgaaatgggccatgtgagagcgaggaacctggcctatgacaccctcccggtcctgatc
PLOD2 aaatttgaaaatggcaaagccagagctaagaatacatttatgaaacattaccagtggcaatt
PLOD3 aagtttgatcggaaccgtgtgcgtatccggaacgtggcctacgacacgctccccattgtggtc PLOD1 H G N G P T K L Q L N Y L G N Y I P R F W
PLOD2 N G N G P T K I L L N Y F G N Y V P N S W
PLOD3 H G N G P T K L Q L N Y L G N Y V P N G W
PLOD1 catggcaacgggccaaccaagctgcagttgaactacctgggcaactacatcccgcgcttctgg
PLOD2 aatggaaatggacccaccaagattctcctgaattattttggaaactatgtacccaattcatgg
PLOD3 catggaaacggtcccactaagctgcagctcaactacctgggaaactacgtccccaatggctgg PLOD1 T F E T G C T V C D E G L R S L K G I G D
PLOD2 T Q D N G C T L C E * F * D T V D L S A V
PLOD3 T P E G G C G F C N * Q * D R R T L P G G
PLOD1 accttcgaaacaggctgcaccgtgtgtgacgaaggcttgcgcagcctcaagggcattggggat
PLOD2 acacaggataatggctgcactctttgtgaa***ttc***gatacagtcgacttgtctgcagta
PLOD3 actcctgagggaggctgtggcttctgcaac*cag*gaccggaggacactcccggggggg PLOD1 E A L P T V L V G V F I E Q P T P F V S L
PLOD2 D V H P N V S I G V F I E Q P T P F L P R
PLOD3 Q P P R V F L A V F V E Q P T P F L P R
PLOD1 gaagctctgcccacggtcctggtcggcgtgttcatcgaacagcccacgccgtttgtgtccctg
PLOD2 gatgtccatccaaacgtatcaataggtgttttattgagcaaccaaccccttttctaccctcgg
PLOD3 cagcctcccccgggtgtttctggccgtgtttgtggaacagcctactccgtttctgccccgc PLOD1 F F Q R L L R L H Y P Q K H M R L F I H N
PLOD2 F L D I L L T L D Y P K E A L K L F I H N
PLOD3 F L Q R L L L L D Y P P D R V T L F L H N
PLOD1 ttcttccagcggctcctgcggctccactaccccagaaacacatgcgacttttcatccacaac
PLOD2 tttctggacatattgttgacactggattacccaaaagaagcacttaaacttttattcataac
PLOD3 ttcctgcagcggctgctactcctggactatcccccgacagggtcacccttttcctgcacaac PLOD1 H E Q H H K A Q V E E F L A Q H G S E Y Q
PLOD2 K E V Y H E K D I K V F F D K A K H E I K
PLOD3 N E V F H E P H I A D S W P Q L Q D H F S
PLOD1 cacgagcagcaccacaaggctcaggtggaagagttcctggcacagcatggcagcgagtaccag
PLOD2 aaagaagtttatcatgaaaaggacatcaaggtattttttgataaagctaagcatgaaatcaaa
PLOD3 aacgaggtcttccatgaacccacatcgctgactcctggccgcagctccaggaccacttctca PLOD1 S V K L V G P E V R M A N A D A R N M G A
PLOD2 T I K I V G P E E N L S Q A E A R N M G M
PLOD3 A V K L V G P E E A L S P G E A R D M A M
PLOD1 tctgtgaagctggtgggccctgaggtgcggatggcgaatgcagatgccaggaacatgggcgca
PLOD2 actataaaaatagtaggaccagaagaaaatctaagtcaagcggaagccagaaacatgggaatg
PLOD3 gctgtgaagctcgtggggccggaggagctctgagcccaggcgaggccagggacatggccatg
```

FIGURE 9C

```
PLOD1  D  L  C  R  Q  D  R  S  C  T  Y  Y  F  S  V  D  A  D  V  A  L
PLOD2  D  F  C  R  Q  D  E  K  C  D  Y  Y  F  S  V  D  A  D  V  V  L
PLOD3  D  L  C  R  Q  D  P  E  C  E  F  Y  F  S  L  D  A  D  A  V  L
PLOD1  gacctgtgccggcaggaccgcagctgcacctactacttcagcgtggatgctgacgtggccctg
PLOD2  gacttttgccgtcaggatgaaagtgtgattattactttagtgtggatgcagatgttgttttg
PLOD3  gacctgtgtcggcaggaccccgagtgtgagttctacttcagcctggacgccgacgctgtcctc
_____

PLOD1  T  E  P  N  S  L  R  L  I  Q  Q  N  K  N  V  I  A  P  L  M
PLOD2  T  N  P  R  T  L  K  I  L  I  E  Q  N  R  K  I  I  A  P  L  V
PLOD3  T  N  L  Q  T  L  R  I  L  I  E  E  N  R  K  V  I  A  P  M  L
PLOD1  accgagcccaacagcctgcggctgctgatccaacagaacaagaatgtcattgccccgctgatg
PLOD2  acaaatccaaggactttaaaaattttgattgaacaaaacagaaagatcattgctcctcttgta
PLOD3  accaacctgcagaccctgcgtatcctcattgaggagaacaggaaggtgatcgcccccatgctg
_____

PLOD1  T  R  H  G  R  L  W  S  N  F  W  G  A  L  S  A  D  G  Y  Y  A
PLOD2  T  R  H  G  K  L  W  S  N  F  W  G  A  L  S  P  D  G  Y  Y  A
PLOD3  S  R  H  G  K  L  W  S  N  F  W  G  A  L  S  P  D  E  Y  Y  A
PLOD1  acccggcatggaggctgtggtcgaacttctgggggctctcagtgcagatggctactatgcc
PLOD2  actcgtcatggaaagctgtggtccaatttctggggagcattgagtcctgatggatactatgca
PLOD3  tcccgccacggcaagctgtggtccaacttctggggcgccctgagccccgatgagtactacgcc
_____

PLOD1  R  S  E  D  Y  V  D  I  V  Q  G  R  R  V  G  V  W  N  V  P  Y
PLOD2  R  S  E  D  Y  V  D  I  V  Q  G  N  R  V  G  V  W  N  V  P  Y
PLOD3  R  S  E  D  Y  V  E  L  V  Q  R  K  R  V  G  V  W  N  V  P  Y
PLOD1  cgttccgaggactacgtggacattgtgcaggggcggcgtgttggtgtctggaatgtgccctat
PLOD2  cgatctgaagattatgtggatattgttcaagggaatagagtaggagtatggaatgtcccatat
PLOD3  cgctccgaggactacgtggagctggtgcagcggaagcgagtgggtgtgtggaatgtaccatac
_____

PLOD1  I  S  N  I  Y  L  I  K  G  S  A  L  R  G  E  L  Q  S  S  D  L
PLOD2  M  A  N  V  Y  L  I  K  G  K  T  L  R  S  E  M  N  E  R  N  Y
PLOD3  I  S  Q  A  Y  V  I  R  G  D  T  L  R  M  E  L  P  Q  R  D  V
PLOD1  atttcaaacatctacttgatcaagggcagtgccctgcggggtgagctgcagtcctcagatctc
PLOD2  atggctaatgtgtacttaattaaaggaaagacactccgatcagagatgaatgaaaggaactat
PLOD3  atctcccaggcctatgtgatccggggtgatacsctgcggatggagctgccccagagggatgtg
_____

PLOD1  F  H  H  S  K  L  D  P  D  M  A  F  C  A  N  I  R  Q  Q  D  V
PLOD2  F  V  R  D  K  L  D  P  D  M  A  L  C  R  N  A  R  E  M  G  V
PLOD3  F  S  G  S  D  T  D  P  D  M  A  F  C  K  S  F  R  D  K  G  I
PLOD1  ttccaccacagcaagctggaccccgacatggccttctgtgccaacatccggcagcaggatgtg
PLOD2  tttgttcgtgataaactggatcctgatatggctctttgccgaaatgctagagaaatgggtgta
PLOD3  ttctcgggcagtgacacagacccggacatggccttctgtaagagcttcgagacaagggcatc
_____

PLOD1  F  M  F  L  T  N  R  H  T  L  G  H  L  L  S  L  D  S  Y  R  T
PLOD2  F  M  Y  I  S  N  R  H  E  F  G  R  L  L  S  T  A  N  Y  N  T
PLOD3  F  L  H  L  S  N  Q  H  E  F  G  R  L  L  A  T  S  R  Y  D  T
PLOD1  ttcatgttcctgaccaaccggcacacccttggccatctgctctccctagacagctaccgcacc
PLOD2  tttatgtacatttctaatagacatgaatttggaaggctattatccactgctaattacaatact
PLOD3  ttcctccatctgagcaatcagcatgaatttggccggctcctggccacttccagatacgacacg
_____

PLOD1  T  H  L  H  N  D  L  W  E  V  F  S  N  P  E  D  W  K  E  K  Y
PLOD2  S  H  Y  N  N  D  L  W  Q  I  F  E  N  P  V  D  W  K  E  K  Y
PLOD3  E  H  L  H  P  D  L  W  Q  I  F  D  N  P  V  D  W  K  E  Q  Y
PLOD1  acccacctgcacaacgacctctgggaggtgttcagcaaccccgaggactggaaggagaagtac
PLOD2  tccattataacaatgacctctggcagatttttgaaaatcctgtggactggaaggaaaagtat
PLOD3  gagcacctgcaccccgacctctggcagatcttcgacaaccccgtcgactggaaggagcagtac
_____

PLOD1  I  H  Q  N  Y  T  K  A  L  A  *  G  K  L  V  E  T  P  C  P  D
PLOD2  I  N  R  D  Y  S  K  I  F  T  *  E  N  I  V  E  Q  P  C  P  D
PLOD3  I  H  E  N  Y  S  R  A  L  E  G  E  G  I  V  E  Q  P  C  P  D
PLOD1  atccaccagaactacaccaaagccctggca***gggaagctggtggagacgccctgcccggat
PLOD2  ataaaccgtgattattcaaagatttttcact***gaaaatatagttgaacagccctgtccagat
PLOD3  atccacgagaactacagccgggccctggaaggggaaggaatcgtggagcagccatgcccggac
_____
```

FIGURE 9D

```
PLOD1 V Y W F P I F T E V A C D E L V E E M E H
PLOD2 V F W F P I F S E K A C D E L V E E M E H
PLOD3 V Y W F P L L S E Q M C D E L V A E M E H
PLOD1 gtctattggttcccatcttcacggaggtggcctgtgatgagctggtggaggagatggagcac
PLOD2 gtcttttggttccccatatttctgaaaaagcctgtgatgaattggtagaagaaatggaacat
PLOD3 gtgtactggttcccactgctgtcagaacaaatgtgtgatgagctggtggcagagatggagcac
----------------------------------------------------------------
PLOD1 F G Q W S L G N N K D N R I Q G G Y E N V
PLOD2 Y G K W S G G K H H D S R I S G G Y E N V
PLOD3 Y G Q W S G G R H E D S R L A G G Y E N V
PLOD1 tttggccagtggtctctgggcaacaacaaggacaaccgcatccagggtggctacgagaacgtg
PLOD2 tacggcaaatggtctggggaaaacatcatgatagccgtatatctggtggttatgaaaatgtc
PLOD3 tacggccagtggtcaggcggccggcatgaggattcaaggctggctggaggctacgagaatgtg
----------------------------------------------------------------
PLOD1 P T I D I H M N Q I G F E R E W H K F L L
PLOD2 P T D D I H M K Q V D L E N V W L D F I R
PLOD3 P T V D I H M K Q V G Y E D Q W L Q L L R
PLOD1 ccgactattgacatccacatgaaccagatcggctttgagcgggagtggcacaaattcctgctg
PLOD2 ccaactgatgatatccacatgaagcaagttgatctggagaatgtatggcttgattttatccgg
PLOD3 cccaccgtggacatccacatgaagcaggtggggtacgaggaccagtggctgcagctgctgcgg
----------------------------------------------------------------
PLOD1 E Y I A P M T E K L Y P G Y Y T R A Q F D
PLOD2 E F I A P V T L K V F A G Y Y T K G F A L
PLOD3 T Y V G P M T E S L F P G Y H T K A R A V
PLOD1 gagtacattgcgcccatgacggagaagctctaccccggctactacaccagggcccagtttgac
PLOD2 gagttcattgcaccagttacactgaaggtctttgcaggctattatacgaagggatttgcacta
PLOD3 acgtatgtgggcccatgaccgagagcctgtttcccggttaccacaccaaggcgcggcggtg
----------------------------------------------------------------
PLOD1 L A F V V R Y K P D E Q P S L M P H H D A
PLOD2 L N F V V K Y S P E R Q R S L R P H H D A
PLOD3 M N F V V R Y R P D E Q P S L R P H H D S
PLOD1 ctggcctttgtcgtccgctacaagcctgatgagcagccctcactgatgccacaccatgatgcc
PLOD2 ctgaattttgtagtaaaatactcccctgaacgacagcgttctcttcgtcctcatcatgatgct
PLOD3 atgaactttgtggttcgctaccggccagacgagcagccgtctctgcggccacaccacgactca
----------------------------------------------------------------
PLOD1 S T F T I N I A L N R V G V D Y E G G G C
PLOD2 S T F T I N I A L N N V G E D F Q G G G C
PLOD3 S T F T L N V A L N H K G L D Y E G G G C
PLOD1 tccaccttcaccatcaacatcgccctgaaccgagtcggggtggattacgagggcggggggctgt
PLOD2 tctacatttaccataaacattgcacttaataacgtgggagaagactttcagggaggtggttgc
PLOD3 tccaccttcaccctcaacgttgccctcaaccacaagggcctggactatgagggaggtggctgc
----------------------------------------------------------------
PLOD1 R F L R Y N C S I R A P R K G W T L M H P
PLOD2 K F L R Y N C S I E S P R K G W S F M E P
PLOD3 R F L R Y D C V I S S P R K G W A L L H P
PLOD1 cggttcctgcgctacaactgttccatccgagccccaaggaagggctggacccctcatgcaccct
PLOD2 aaatttctaaggtacaattgctctattgagtcaccacgaaaaggctggagcttcatgcatcct
PLOD3 cgcttcctgcgctacgactgtgtgatctcctccccgaggaagggctgggcactcctgcacccc
----------------------------------------------------------------
PLOD1 G R L T H Y H E G L P T T R G T R Y I A V
PLOD2 G R L T H L H E G L P V K N G T R Y I A V
PLOD3 G R L T H Y H E G L P T T W G T R Y I M V
PLOD1 ggacgactcacgcattaccatgaggggctccccaccaccaggggcacccgctacatcgcagtc
PLOD2 gggagactcacacatttgcatgaaggacttcctgttaaaaatggaacaagatacattgcagtg
PLOD3 ggccgcctcacccactaccacgaggggctgccaacgacctggggcacacgctacatcatggtg
----------------------------------------------------------------
PLOD1 S F V D P
PLOD2 S F I D P
PLOD3 S F V D P
PLOD1 tccttcgtcgatccc
PLOD2 tcatttatagatccc
PLOD3 tcctttgtcgacccc
----------------------------------------------------------------
```

INHIBITION OF TELOPEPTIDE LYSYL HYDROXYLASE ACTIVITY OR PRODUCTION AS ANTI-FIBROTIC THERAPY

BACKGROUND OF THE INVENTION

Fibrosis and Scarring

Normal wound healing involves the formation of scars and fibrous tissues. Their structures consist largely of collagen fibrils. Although collagen is required in wound repair, collagen often accumulates in excessive amounts and impairs the normal function of the affected tissue. Such excessive amounts of collagen become an important event in scarring of the skin following burns or other traumatic injury, as well as in fibrosis of the liver, lungs and other organs following injury. Because of the central role of collagen in the pathogenesis of fibrosis, there has been considerable interest in agents capable of inhibiting collagen accumulation in fibrotic diseases. Potential target sites for inhibiting collagen accumulation include transcription of the genes, translation of the mRNAs, and some of the post-translational enzymes involved in the biosynthesis of collagen [G. C. Fuller, 1981, J. Med. Chem., 24: 651–658; M. Trojanowska et al., 1998, J. Mol. Med., 76: 266–274]. Here we will focus our attention to circumvent collagen accumulation in fibrosis by inhibiting cross-link levels. To understand the rationale behind attempts to circumvent collagen accumulation by inhibiting cross-link levels it is necessary to get an insight into the way cross-linking of collagen molecules occurs.

Hydroxylation and Cross-linking of Collagen: Some Basic Concepts

Biosynthesis of collagen is a multistep process, resulting in extensive modification of the molecule (FIG. 1). The different modifications of the molecule are catalyzed by various enzymes with an intra- or extracellular localization [K. Kadler, 1994, Protein Profile, 1: 515–638]. One of the steps in the biosynthesis of collagen is hydroxylation of certain proline residues in the triple helix by prolyl 4-hydroxylase (EC 1.14.11.2) and prolyl 3-hydroxylase (EC 1.14.11.7) as well as hydroxylation of certain lysine residues in the triple helix and telopeptides by lysyl hydroxylase (EC 1.14.11.4). In a next step, hydroxylysine residues in the triple helix can be subjected to glycosylation by glycosyl transferases. Hydroxylation of proline and lysine are essential for a proper functioning of collagen. There is hardly any variation in the level of prolyl hydroxylation within a specific collagen type. In fact, the hydroxylation level of prolyl residues of each fibrillar collagen type is close to a maximum; underhydroxylation of proline residues results in a non-functional molecule with a weakened triple helix that can easily be degraded. In contrast, there are large variations in lysyl hydroxylation within the same collagen type (e.g. type I collagen) between the different tissues. The functional significance of this variation is unknown, but under- and overhydroxylation of lysine residues is associated with several connective tissue disorders, such as Ehlers-Danlos type VI syndrome [A. Ihme et al., 1984, J. Invest. Dermatol., 83: 161–165] and osteogenesis imperfecta [W. G. Cole, 1994, Bone Miner. Res., 8: 167–2041].

Once the collagen molecule is secreted, the propeptides are cleaved off by procollagen N-peptidase (EC 3.4.24.14) and procollagen C-peptidase (EC 3.4.24.19), resulting in a mature molecule consisting of a triple helix with a short telopeptide at both termini. The mature molecules aggregate spontaneously into microfibrils. Further stabilization of the molecules occurs by means of cross-links. Cross-linking is initiated by conversion of specific lysine or hydroxylysine residues of the telopeptides into the aldehydes allysine and hydroxyallysine, respectively, by the enzyme lysyl oxidase (EC 1.4.3.13) [H. M. Kagan, 1994, Path. Res. Pract., 190: 910–919]. The aldehydes subsequently react with lysine or hydroxylysine residues of the triple helix to give characteristic difunctional cross-links. These cross-links eventually mature into tri- or tetra-functional cross-links [D. R. Eyre, 1987, Meth. Enzymol., 144: 115–139; A. J. Bailey et al., 1998, Mech. Ageing Developm., 106: 1–56]. Two related routes for the formation of cross-links have been described, one based on allysine from the telopeptides, the other based on the hydroxyallysine of the telopeptides. Each route results in chemically distinct cross-links. For the nomenclature and origin of some of the most common cross-links we refer to FIG. 2.

Hydroxylation of lysine in the triple helix of collagen occurs exclusively on lysine present in the helical amino acid sequence Gly-X-Lys-Gly; a lysine in the X position is not hydroxylated [K. Kadler, 1994, Protein Profile, 1: 515–638]. The hydroxylated lysine in the telopeptides is embedded in an entirely different amino acid sequence; in view thereof, the existence of another enzyme, whose substrate would be the non-helical telopeptide region, has occasionally been proposed [J. E. Gerriets et al., 1996, Biochim. Biophys. Acta, 1316: 121–131; J. E. Gerriets et al., 1993, J. Biol. Chem., 286: 25553–25560; L. Knott et al, 1997, Biochem. J., 322: 535–542; M. J. Barnes et al., 1974, Biochem. J., 139: 461–468; P. M. Royce & M. J. Barnes, 1985, Biochem. J., 230: 475–480]. However, the circumstantial evidence that an enzyme exists that specifically hydroxylates the telopeptide lysine has mostly been ignored and/or questioned. We will show later on that hydroxylation of telopeptide lysine residues is indeed under separate control from that of helical lysine residues, i.e. hydroxylation of telopeptide lysine and helical lysine is independently and specifically controlled.

Suppression of Cross-link Formation as an Antifibrotic Treatment

Essentially all stages of collagen biosynthesis have been used as targets for the pharmacological control of collagen accumulation in fibrosis, the most important ones being the inhibition of prolyl hydroxylation (e.g. by incorporation of prolyl analogues into the triple helix instead of prolyl) [H. M. Hanauske-Abel, 1991, J. Hepatol., 13 Suppl. 3: S8–S16] and cross-linking. Here we will focus our attention to the inhibition of cross-link formation as a tool to decrease collagen accumulation in fibrotic tissues. Collagen molecules that are not cross-linked are more easily degraded by proteinases [C. A. Vater et al., 1979, Biochem. J., 181: 639–645], thus facilitating the removal of collagen. Two routes have been described to achieve lower cross-link levels: compounds that are able to inhibit lysyl oxidase (so-called lathyrogens, an example being β-aminopropionitrile) and compounds that essentially block aldehydes (such as penicillamine, cysteine, and other analogues) [M. E. Nimni, 1983, Sem. Arthr. Rheum., 13: 1–86]. Both routes result in a decrease of both allysine and hydroxyallysine derived cross-links. The consequence of inhibition of lysyl oxidase is that aldehydes cannot be formed in the telopeptides; as a result, cross-link formation does not take place (FIG. 1–2). Blocking the aldehydes also effectively inhibits cross-link formation, as blocked aldehydes cannot participate in the formation of intramolecular and intermolecular cross-links. Although lathyrogens and compounds that react with aldehydes are potent antifibrotic agents, concentrations needed to display antifibrotic effects have toxic effects, thus limiting its clinical use as antifibrotic drugs. An additional drawback is, that unphysiological collagen is formed, showing inferior biomechanical properties due to the lower cross-link levels. This unphysiological collagen is not only formed by proliferating fibroblasts but also by the cells surrounding the injury, thus impairing the biomechanical quality of healthy tissue as well. In this invention we will describe a method that does not show this drawback: agents can be developed that selectively inhibit the formation of unwanted hydroxyallysine cross-links in collagen of the fibrotic lesions, leaving synthesis of allysine cross-links in the intact tissue and healing wound unaffected.

In yet another approach minoxidil, an agent capable of suppressing fibroblast proliferation and expression of lysyl hydroxylase by fibroblasts, has been proposed as a drug for treating tissue disorders associated with fibroblast hyperproliferation and collagen accumulation (as is the case in fibrosis) [S. Murad & Pinnell, 1987, J. Biol. Chem., 262: 11973–11978; S. Murad et al., 1987, Arch. Biochem. Biophys., 292: 234–238; J. T. Handa et al., 1994, Invest. Ophthalmol. Vis. Sci., 35: 463–469; J. T. Handa et al., 1993, Invest. Ophthalmol. Vis. Sci., 34: 567–575; S. Murad et al., 1994, Arch. Biochem. Biophys., 308: 42–47]. With respect to the suppression of lysyl hydroxylase, it was suggested that "The rationale for this therapeutic approach to fibrosis is based on the consideration that a collagen deficient in hydroxylysine and therefore hydroxylysine-derived crosslinks would be deposited in the extracellular matrix as a nonfunctional protein with increased susceptibility to degradation by collagenase, thus limiting its amount in the fibrotic tissue" [S. Murad et al., 1994, Arch. Biochem. Biophys., 308: 42–47]. In the context of this and other papers of the same group it is clear that the authors believe that lowering the hydroxylysine levels in the telopeptides results in decreased cross-link levels. The authors specifically stated that minoxidil reduces cross-link levels [J. T. Handa et al., 1994, Invest. Ophthalmol. Vis. Sci., 35: 463–469; J. T. Handa et al., 1993, Invest. Ophthalmol. Vis. Sci., 34: 567–575; S. Murad et al., 1994, Arch. Biochem. Biophys., 308: 42–47]—despite the lack of any experimental evidence for this statement. Such a statement is not necessarily true and as a matter of fact even unlikely. Firstly, hydroxyallysine-derived cross-links are likely to be replaced by allysine-derived cross-links. Secondly, although minoxidil inhibits mRNA levels of PLOD1 (thereby reducing Hyl levels of the triple helical part of collagen) [e.g. T. Hautala et al., 1992, Biochem. J., 283: 51–54], it has never been shown that minoxidil reduces the lysyl hydroxylation level in the telopeptides: it was at that time believed that lysyl hydroxylase encoded by PLOD1 was capable of hydroxylating the lysine residues in both the triple helix and the telopeptides of collagen molecules, which is not the case. The abbreviation PLOD is derived from procollagen-lysine, 2-oxoglutarate 5-dioxygenase (which is the systematic name of lysyl hydroxylase), the 1 indicates that it is the first discovered PLOD gene.

The Heritable Connective Tissue Disease Ehlers-Danlos Type VI Syndrome Revealed Genetic Evidence That Lysyl Hydroxylation of Collacien is a Complex Process PLOD1 is the gene that is mutated in Ehlers-Danlos type VI syndrome (EDS-VI) [J. Brickmann et aL, 1998, Arch. Dermatol. Res., 290: 181–186], a disease that is biochemically characterized by a hydroxylysine deficiency of collagen. Close examination of EDS-VI patients revealed that, although collagen type I and III in most tissues are Hyl deficient, collagen type II and V are not [A. Ihme et al., 1984, J. Invest. Dermat., 83: 161–165]. Thus it appears, that collagen-type specific lysyl hydroxylases exist. The presence of such lysyl hydroxylases was also postulated by Risteli et al. [1980, Biochem. Biophys. Res. Commun., 96: 1778–1784], who found that lysyl hydroxylase of normal fibroblasts preferentially hydroxylated collagen type I, whereas the residual lysyl hydroxylase activity of EDS-VI fibroblasts was preferentially directed towards type IV collagen. In addition, EDS-VI patients show differences in the hydroxylation of collagen type I derived from various tissues: collagen type I from skin and bone are Hyl deficient, whereas collagen type I from tendon, kidney and lung was not [A. Ihme et al., 1984, J. Invest. Dermatol., 83: 161–165]. This indicates the existence of tissue-specific forms of collagen-type specific lysyl hydroxylases.

Recently, two other lysyl hydroxylases have been cloned, PLOD2 (SEQ ID NO. 7–12) and PLOD3 (SEQ ID NO. 13–16), with an overall amino acid sequence identity of 75% and 59% with that of PLOD1 (SEQ ID NO. 1–6), respectively. The three lysyl hydroxylases show a tissue-specific distribution [M. Valtavaara et al., 1997, J. Biol. Chem., 272: 6831–6834; M. Valtavaara et al., 1998, J. Biol. Chem., 273: 12881–12886; K. Passoja et al., 1998, Proc. Natl. Acad. Sci. USA, 95: 10482–10486]. PLOD2 also shows a tissue-specific splice variant [H. N. Yeowell & L. C. Walker, 1999, Matrix Biol., 18: 179–187]. Furthermore, there is some evidence at the DNA level that tissue-specific forms of PLOD1 exist [H. N. Yeowell et aL, 1994, J. Invest. Dermatol., 102: 382–384]. PLOD1-3 have been expressed in a baculovirus expression system; the proteins encoded by the cDNA exhibit activity towards the synthetic peptide containing the helical sequence IKGIKGIKG. Although the specificity of PLOD1-3 towards the different collagen types has so far not been investigated, the relatively low sequence homology indicates differences in the substrate properties of these enzymes.

Interestingly, EDS-VI patients show a normal level of pyridinolines in tissues (e.g. in collagen type I from bone) or a normal excretion level of pyridinolines in urine [B. Steinmann et al, 1995, Am. J. Hum. Genet., 57: 1505–1508]. Pyridinolines are cross-links derived from the hydroxyallysine route (FIG. 2). Thus, despite the deficiency of Hyl in the triple helix, a normal amount of Hyl is present in the telopeptides. This is circumstantial evidence for yet another set of lysyl hydroxylases, for which the term "telopeptide lysyl hydroxylase" has been coined (as opposed to "helical lysyl hydroxylase").

BRIEF SUMMARY OF THE INVENTION

If a telopeptide lysyl hydroxylase indeed exists, one would expect that diseases exist that are characterized by an upregulation or downregulation of telopeptide lysyl hydroxylase, resulting in an increase or decrease of telopeptide hydroxylysine and, consequently, in an increase or decrease of hydroxyallysine-derived cross-links. It is shown herein that the underlying molecular defect of the Bruck syndrome (a heritable connective tissue disease) is the virtual absence of telopeptide hydroxylysine of collagen type I in bone, thus providing for the first time genetic evidence for the presence of telopeptide lysyl hydroxylase. Furthermore, in Bruck syndrome a normal level of telopeptide hydroxylysine of collagen type I in joint ligament is seen, thus providing for the first time genetic evidence that tissue-specific telopeptide lysyl hydroxylases exist. Moreover, it is shown herein that there is a telopeptide lysyl hydroxylase which is located on chromosome 17p12, and that PLOD2 (located on chromosome 3) encodes for a telopeptide lysyl hydroxylase (SEQ ID NO. 7–12). Furthermore, it is shown herein that collagen molecules cross-linked by means of hydroxyallysine cross-links have a different intrafibrillar packing than molecules cross-linked by means of allysine, that telopeptide lysyl hydroxylase is upregulated in scars and other fibrotic tissues and that collagen molecules crosslinked by hydroxyallysine are more resistant toward proteolytic enzymes, explaining at least in part the irreversibility of collagen accumulation in fibrosis. It is an object of the present invention to provide a new method for the prevention of excessive collagen accumulation in wound healing and in other processes in which fibrosis occurs as the final outcome by inhibiting the formation of hydroxyallysine-derived cross-links.

This invention provides a method of treating a fibrotic condition in a mammal suffering from said condition comprising administration to said mammal of an effective amount of a composition that selectively inhibits the activity or production of telopeptide lysyl hydroxylase.

The words "selectively inhibits the activity or production of telopeptide lysyl hydroxylase" are used herein in a broad sense, in that they not only cover the actual inhibition of the enzyme as such, but also cover a selective inhibition of the transcription of a telopeptide lysyl hydroxylase gene, selective inhibition of the translation of mRNA derived from a telopeptide lysyl hydroxylase gene, and treatment with (a recombinant gene coding for) a mutated telopeptide lysyl hydroxylase that shows no activity towards telopeptides but that is competitive to endogenous telopeptide lysyl hydroxylase with respect to its natural substrate (collagen telopeptides).

The method of the invention is broadly applicable with mammals of any kind, but in a preferred embodiment said mammal is a human being.

Other objects, features and advantages of the present invention will become apparent as the description proceeds.

Figure 4:
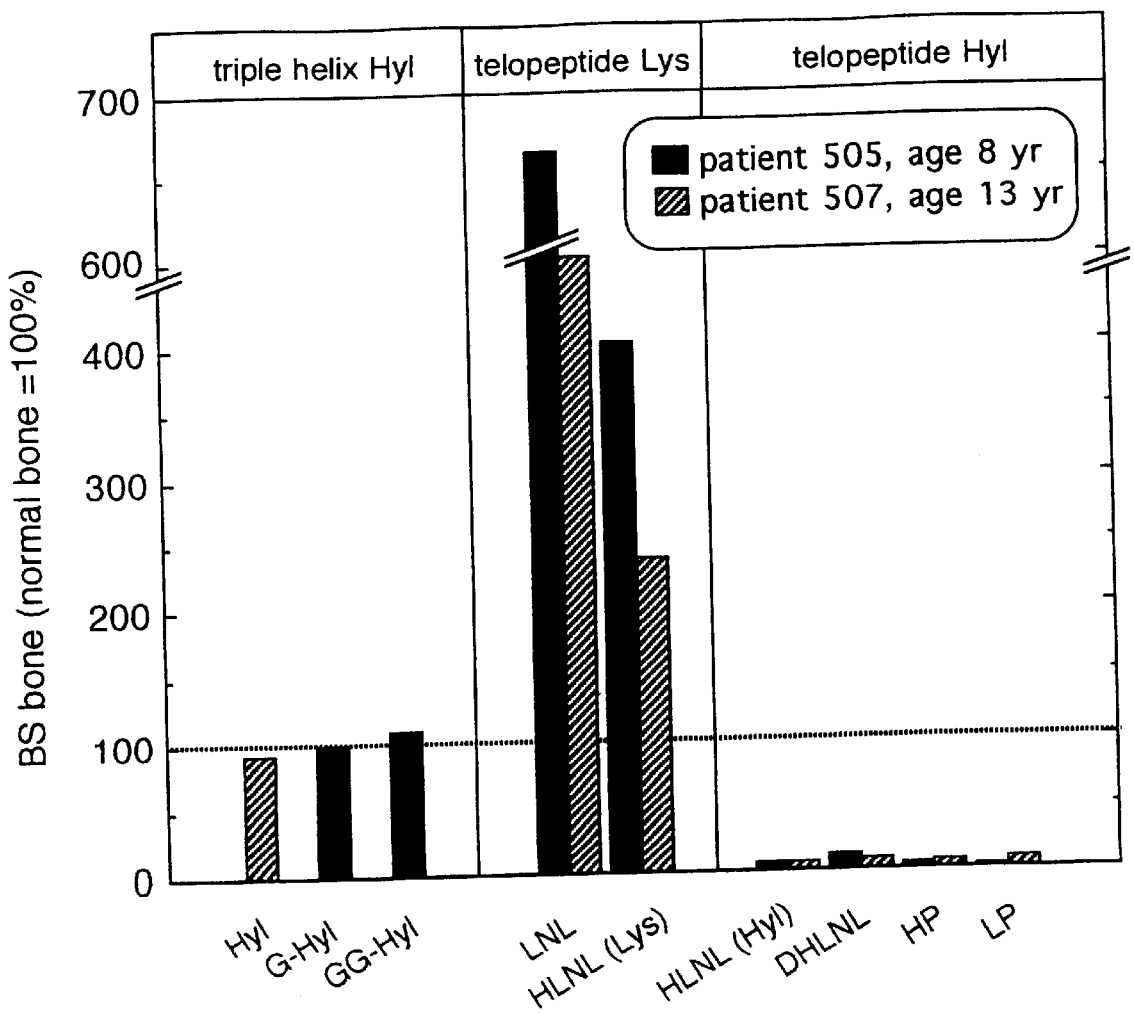
FIG. 4 is a graph showing posttranslational levels of type I collagen in Bruck syndrome bone normalized against posttranslational levels of type I collagen in normal bone. Bar graphs show that hydroxylysine (Hyl), galactosylhydroxylysine (G-Hyl) and glucosylgalactosylhydroxylysine (GG-Hyl) levels of the triple helix are normal, which is in contrast to that of the telopeptides, where hardly any hydroxylysine is seen. The lack of telopeptide Hyl-derived cross-links is compensated by increased levels of cross-links derived from the telopeptide lysine (Lys) route. LNL= lysinonorleucine; HLNL (Lys)=hydroxylysinonorleucine denved from telopeptidyl lysine; HLNL (Hyl)=hydroxylysino-norleucine derived from telopeptidyl hydroxylysine; DHLNL=dihydroxylysinonorleucine; HP=hydroxylysylpyridinoline; LP lysylpyridinoline.
Figure 5:
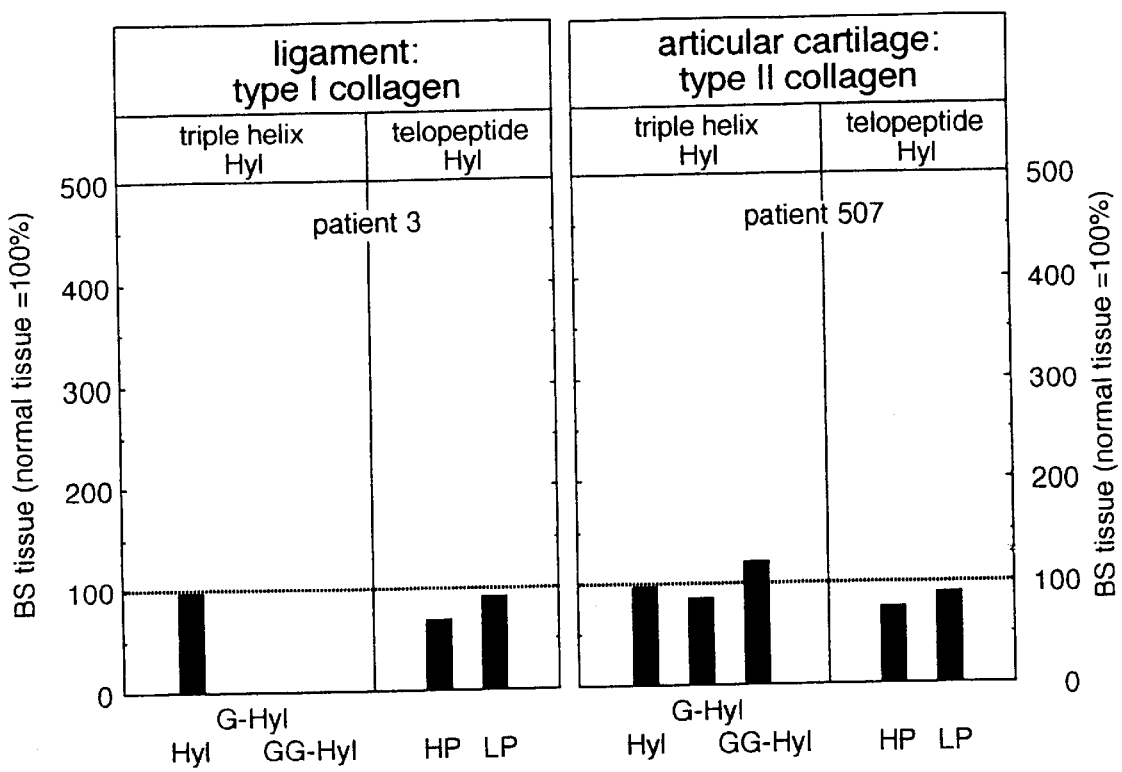

FIG. 5 is a graph showing that the lysyl hydroxylation level of the telopeptides and the triple helix of collagen type I in joint ligament of Bruck syndrome patient 3 is normal and that the lysyl hydroxylation level of the telopeptides and the triple helix of collagen type II in cartilage of Bruck syndrome patient 507 is normal as well. This is in contrast to the situation seen in the bone of these patients, where very low levels of hydroxylysine were found in the telopeptides of collagen type I (see FIG. 4). The data indicate that the defective telopeptide lysyl hydroxylation is restricted to bone. Hyl=hydroxylysine, HP=hydroxylysylpyrdinoline, LP=lysylpyridinoline, gal-hyl=galactosylhydroxy-lysine, glc-gal-hyl=glucosylgalactosylhydroxylysine.

Figure 6:
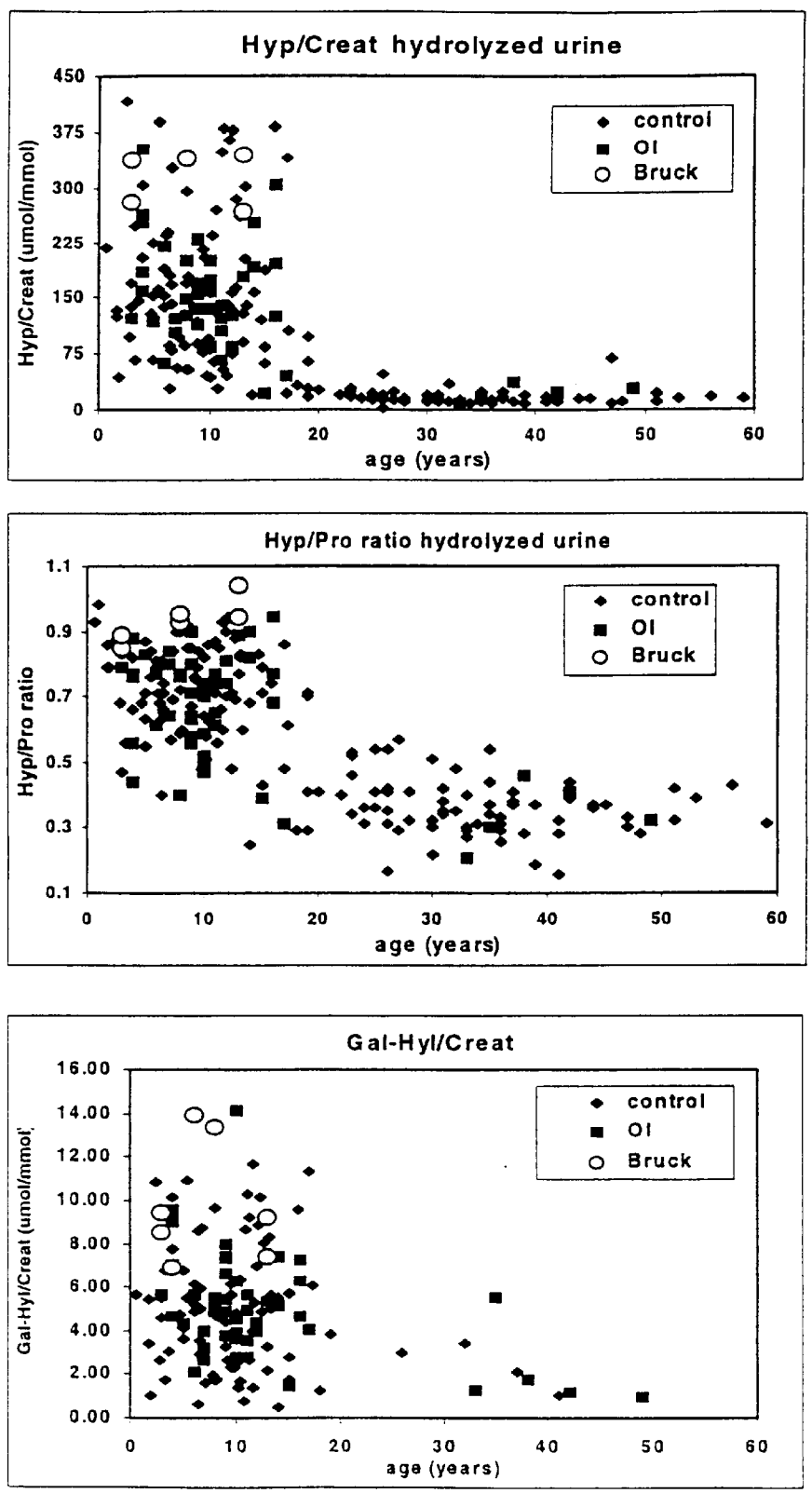

FIG. 6 shows the graphs depicting the level of collagen degradation products (Hyl=hydroxyproline, Gal-Hyl=galactosylhydroxylysine) as well as the hydroxyproline to proline (Hyp:Pro) ratio in Bruck syndrome urine compared to urine from healthy subjects and urine from osteogenesis imperfecta patients. The data indicate that the degradation of bone collagen in Bruck syndrome is significantly elevated.

Figure 7:
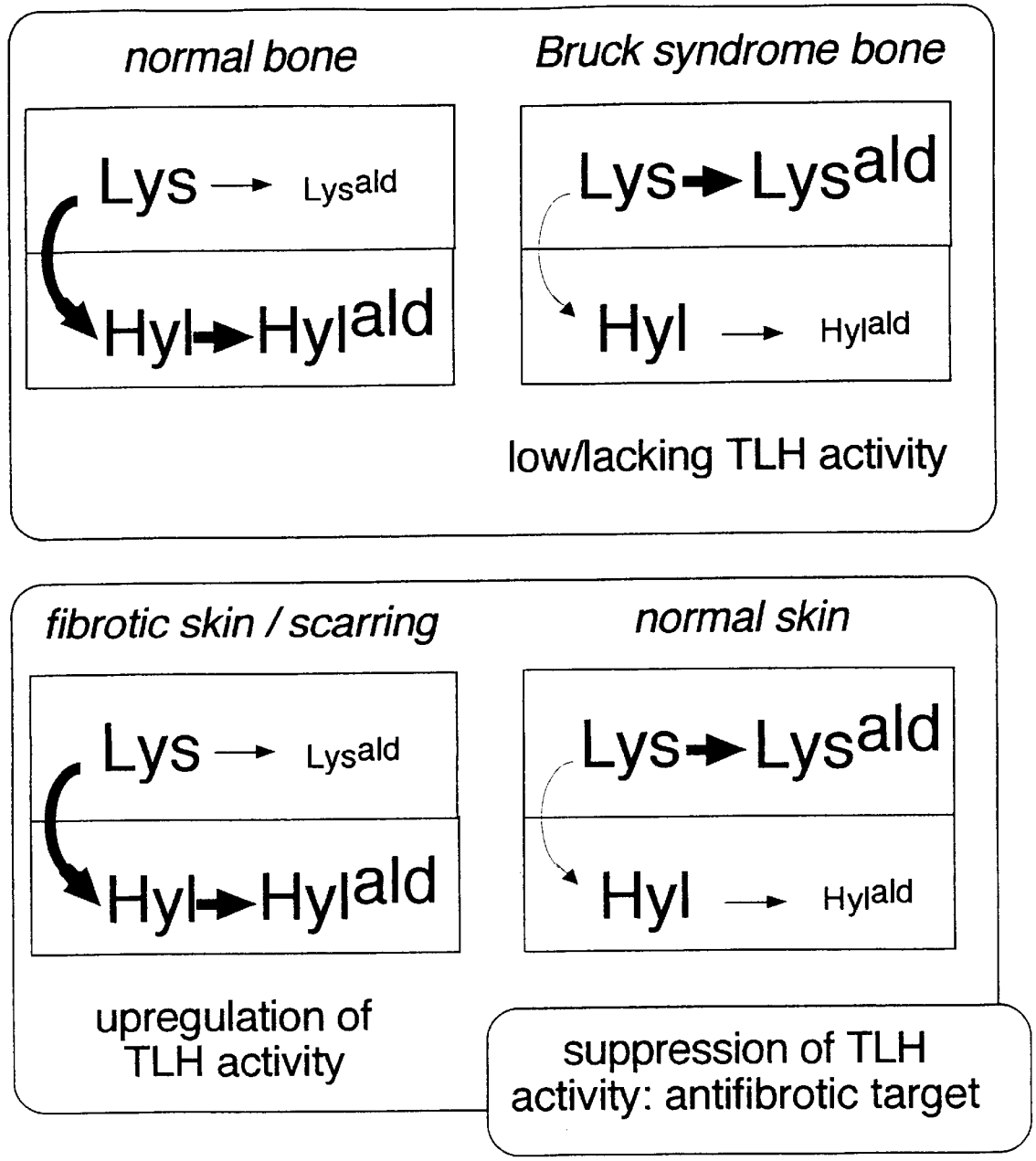

FIG. 7 is a diagram showing the molecular defect in Bruck syndrome and the relation of this discovery with respect to cross-link patterns in scars/fibrosis. In normal bone, most of the telopeptide lysine (Lys) residues are converted to hydroxylysine (Hyl) due to telopeptide lysyl hydroxylase (TLH); a dominance is found of hydroxyallysine ($Hyl^{ald}$) derived cross-links. In Bruck syndrome bone, only a small amount of telopeptide Lys is converted into Hyl (due to low activity levels of telopeptide lysyl hydroxylase), leading to a dominance of allysine ($Lys^{ald}$) derived cross-links. Fibrotic/scarred skin is the "opposite side of the coin" of the defect seen in Bruck syndrome bone: compared with normal skin, fibrotic/scarred skin shows abnormal high levels of hydroxyallysine-derived cross-links due increased activity levels of telopeptide lysyl hydroxylase.

Figure 8:
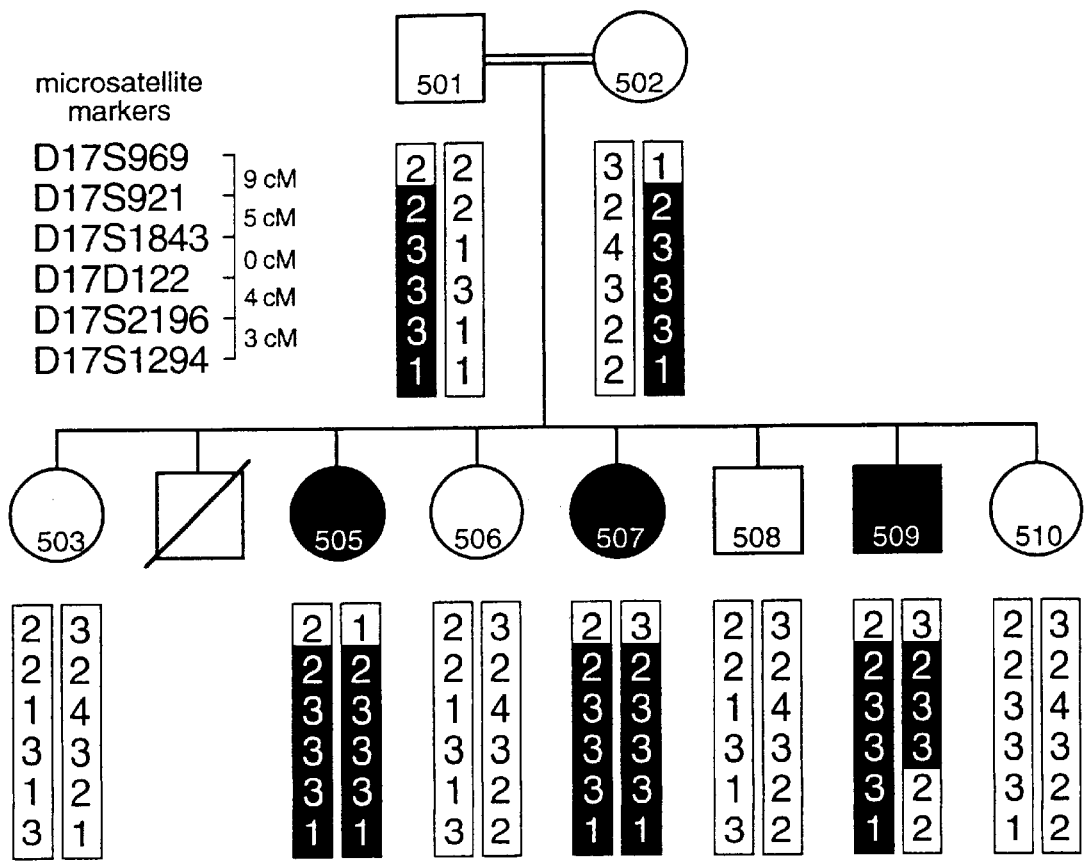

FIG. 8 is a pedigree of a Bruck syndrome family showing the genotypes in the region of homozygosity on chromosome 17p12. The regions of homozygosity in the affected children are boxed. The distances between the DNA markers are indicated next to the markers. These distances were extracted from the Marshfield genetic maps (http://www.marshmed.org).

FIG. 9 shows the sequence alignment of human lysyl hydroxylase encoded by PLOD1 (SEQ ID NO. 1–6), PLOD2 (SEQ ID NO. 7–12) and PLOD3 (SEQ ID NO. 13–16). The sequences shown are derived from cDNA; only the DNA stretch is shown that codes for the protein part of the gene. Stars show gaps introduced by insertions/deletions. The sequences have been expressed in the single letter code: A: Ala, C: Cys, D: Asp, E: Glu, F: Phe, G: Gly, H: His, I: Iie, K: Lys, L: Leu, M: Met, N: Asn, P: Pro, Q: Gin, R: Arg, S: Ser, T: Thr, V: Val, W: Trp, Y: Tyr. The residues of PLODZ that are of special interest with respect to inhibiting the activity of the encoded enzyme by means of site-directed mutagenesis are shown in bold. The sequences of PLOD1, PLOD2 and PLODS were obtained from GenBank (accession numbers L06419, 084573, and AF046889, respectively). FIG. 9a and 9d show the amino acid sequence and the nucleotide sequence, respectively of PLOD1; FIG. 9b and 9e show the amino acid sequence and the nucleotide sequence, respectively of PLOD2; FIG. 9c and 9f show the amino acid sequence and the nucleotide sequence, respectively of PLOD3.

Figure 10:
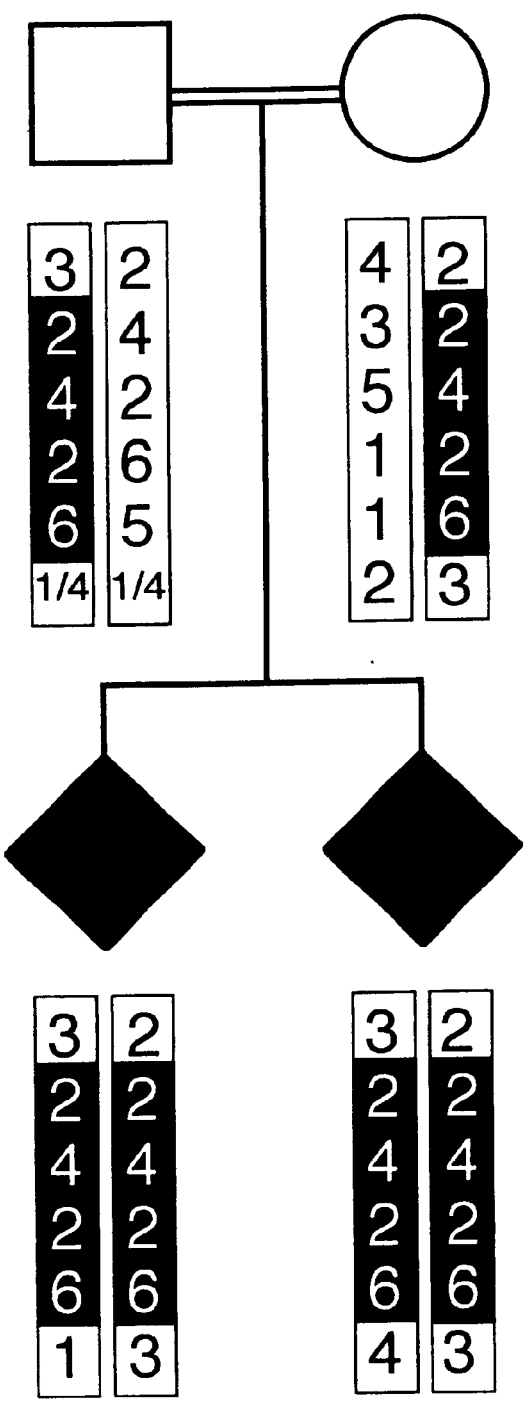

FIG. 10 is a pedigree of a Bruck syndrome family showing the genotypes in the region of homozygosity on chromosome 3 reference interval D3S1557–D3S1306 (164.6–168.3 cM) where the gene PLOD2 is located. The regions of homozygosity in the affected children are boxed.

DETAILED DESCRIPTION OF THE INVENTION

Figure 1:
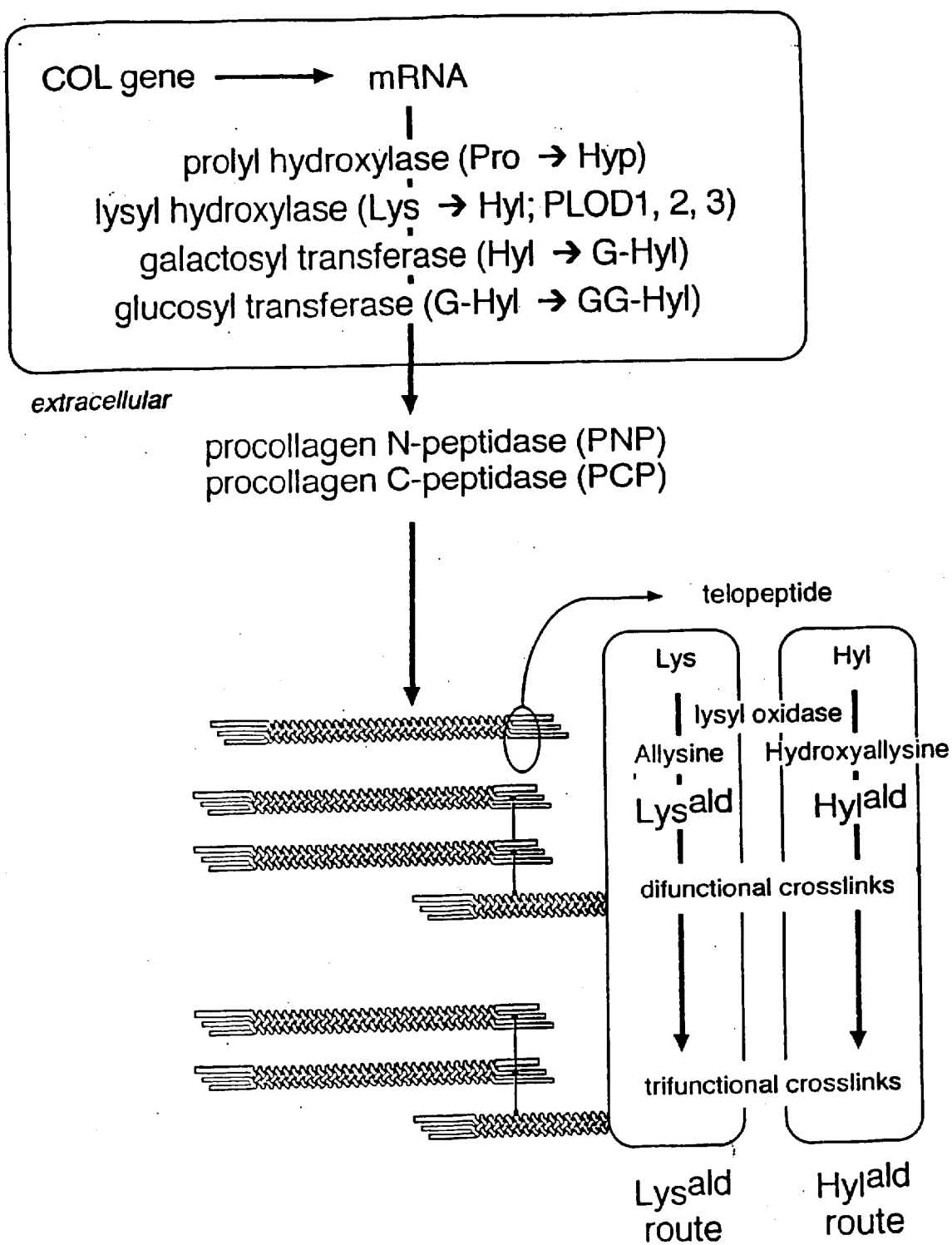
FIG. 1 is a diagram of some of the biosynthetic steps required for the formation of a stable collagen type I molecule, with special emphasis on the modifications occurring on the α-chain itself. After transcription of the collagen gene into mRNA, the mRNA is translated into a polypeptide backbone. The intracellular processing of the collagen polypeptide chain include amongst others (1) cleavage of the signalpeptide at the N-terminus of the chain, (2) hydroxylation of some of the proline and lysine residues of the Y position in the sequence Gly-X-Y-Gly to 4-hydroxyproline (4Hyp) and hydroxylysine (Hyl) by respectively prolyl 4-hydroxylase (EC 1.14.11.2) and lysyl hydroxylase (EC 1.14.11.4), (3) hydroxylation of a few X-position proline residues in the sequence Gly-X-4Hyp-Gly to 3-hydroxyproline (3Hyp) by prolyl 3-hydroxylase (EC 1.14.11.7), (4) addition of galactose to some of the hydroxy-lysine residues by hydroxylysyl galactosyltransferase (EC 2.4.1.50), and (5) addition of glucose to some of the galactosylhydroxylysine (Gal-Hyl) residues by hydroxylysyl glucosyl-transferase (EC 2.4.1.66). Once the folded collagen molecule is secreted, the N-propeptides and C-propeptides are cleaved by procollagen N-proteinase (EC 3.4.24.14) and procollagen C-proteinase (EC 3.4.24.19). After self-assembly into fibrils, lysyl oxidase (EC 1.4.3.13) converts specific lysine or hydroxylysine residues in the non-helical telopeptide regions into lysyl aldehyde (=allysine) and hydroxylysyl aldehyde (=hydroxyallysine), respectively. The aldehydes subsequently react with other amino acids and an assortment of di-, tri- and even tetrafunctional cross-links (FIG. 2) form spontaneously within the newly formed collagen polymers. It is not known whether the conversion of telopeptide lysine to hydroxylysine occurs intracellularly or extracellularly.
Figure 3:
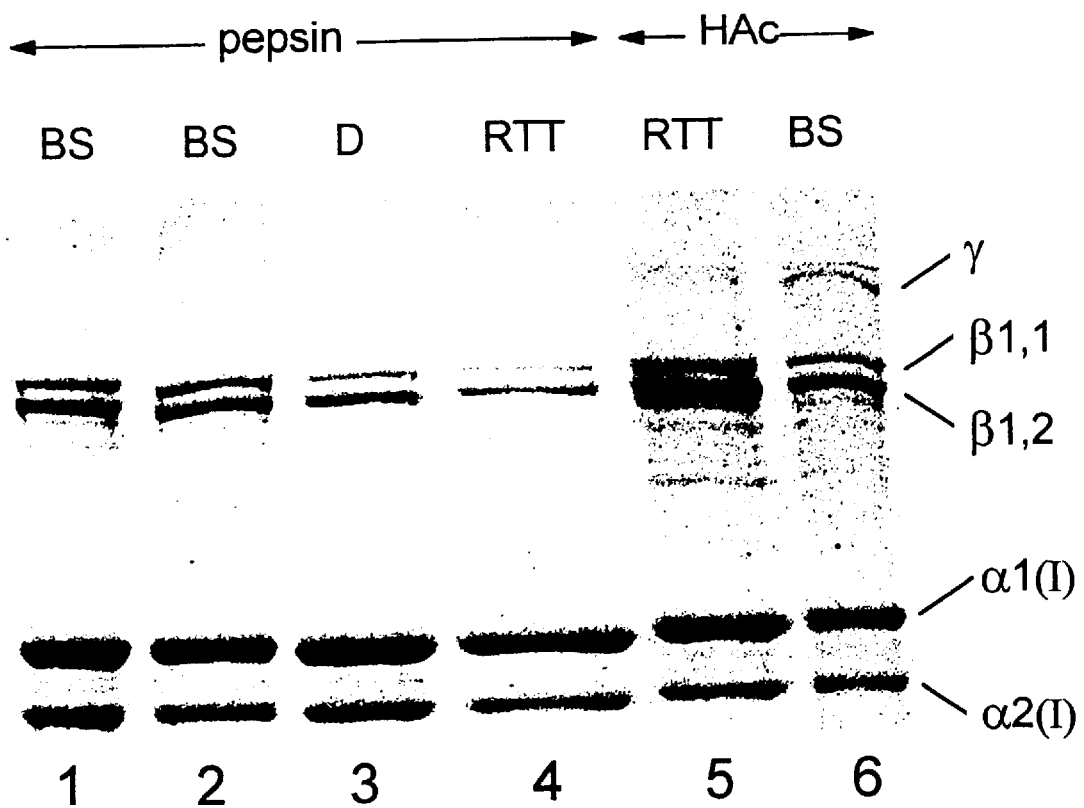
FIG. 3 is a photograph showing analysis by polyacrylamide gel electrophoresis in SDS of collagen type I derived from various sources. SDS-PAGE of Bruck syndrome (BS) bone collagen type I, either solubilized with pepsin (lanes 1 and 2) or extracted with 0.5 M acetic acid (lane 6), show no differences in electrophoretic mobility compared with pepsinized collagen type I from normal human dermis (D, lane 3) or rat tail tendon (RTT, lane 1), or with acetic acid extracted RTT (lane 5). Collagens solubilized with acetic acid contain intact telopeptides, accounting for the slightly slower electrophoresis migration rate compared with pepsinized collagen containing partly degraded telopeptides. Lanes 1 and 6: cortical BS bone, patient 505; lane 2: trabecular BS bone, patient 507. The normal migration of Bruck syndrome type I collagen, the normal ratio of α1(I):Δ2(I) chains and the presence of β-bands and γ-bands indicate that there is a proper processing of propeptides, that there is a proper modification of lysyl residues in the triple helix (no overmodification such as is often the case in osteogenesis imperfecta), that a proper heterotrimer is formed and that there is a proper initiation of cross-linking by lysyl oxidase.

Bruck Syndrome Provides Genetic Evidence for the Existence of TeloPeptide Lysvl Hydroxylases With a Tissue-specific Distribution The Bruck syndrome, an autosomal recessive disease discovered a century ago, is characterized by fragile bones with congenital joint contractures. A reduction of mineral content and an increase in size of the hydroxyapatite crystals was observed. World-wide only a few (less than 20) Bruck syndrome families have been reported. Although an abnormality in the bone collagen network was assumed, the underlying defect remained unknown [R. E. Brenner et al., 1993, Eur. J. Pediatr., 152: 505–508]. An amino acid substitution resulting in a delayed triple helical formation (and subsequent overmodification of hydroxylysine residues), which is seen in many osteogenesis imperfecta patients, can be excluded because the molecular weight of pepsin-treated α1(I) and α2(I) collagen chains is not increased (FIG. 3). The collagen is of a normal heterotrimeric origin, as a normal α1 (I):α2(I) ratio of 2:1 is seen (FIG. 3). Following ribosomal assembly, collagen undergoes several modifications by intra- and extracellular enzymes (FIG. 1). In Bruck syndrome, triple helical lysyl hydroxylase is present in normal amounts, as collagen derived from cortical and trabecular bone revealed a normal degree of lysyl hydroxylation of the triple helix (Table 1; FIG. 4). The same applies to hydroxylysyl glycosyl transferases: a normal glycosylation of triple helical Hyl was found (Table 1; FIG. 4). The N- and C-terminal propeptides were normally processed by their respective peptidases, since the migration of acid soluble collagen on SDS-PAGE indicated the absence of both propeptides (FIG. 3). The prominent presence of cross-linked β-bands. (FIG. 3) infers that the telopeptides are oxidized to aldehydes. Therefore, also no alterations are expected in lysyl oxidase, the enzyme that initiates cross-linking.

Figure 2:
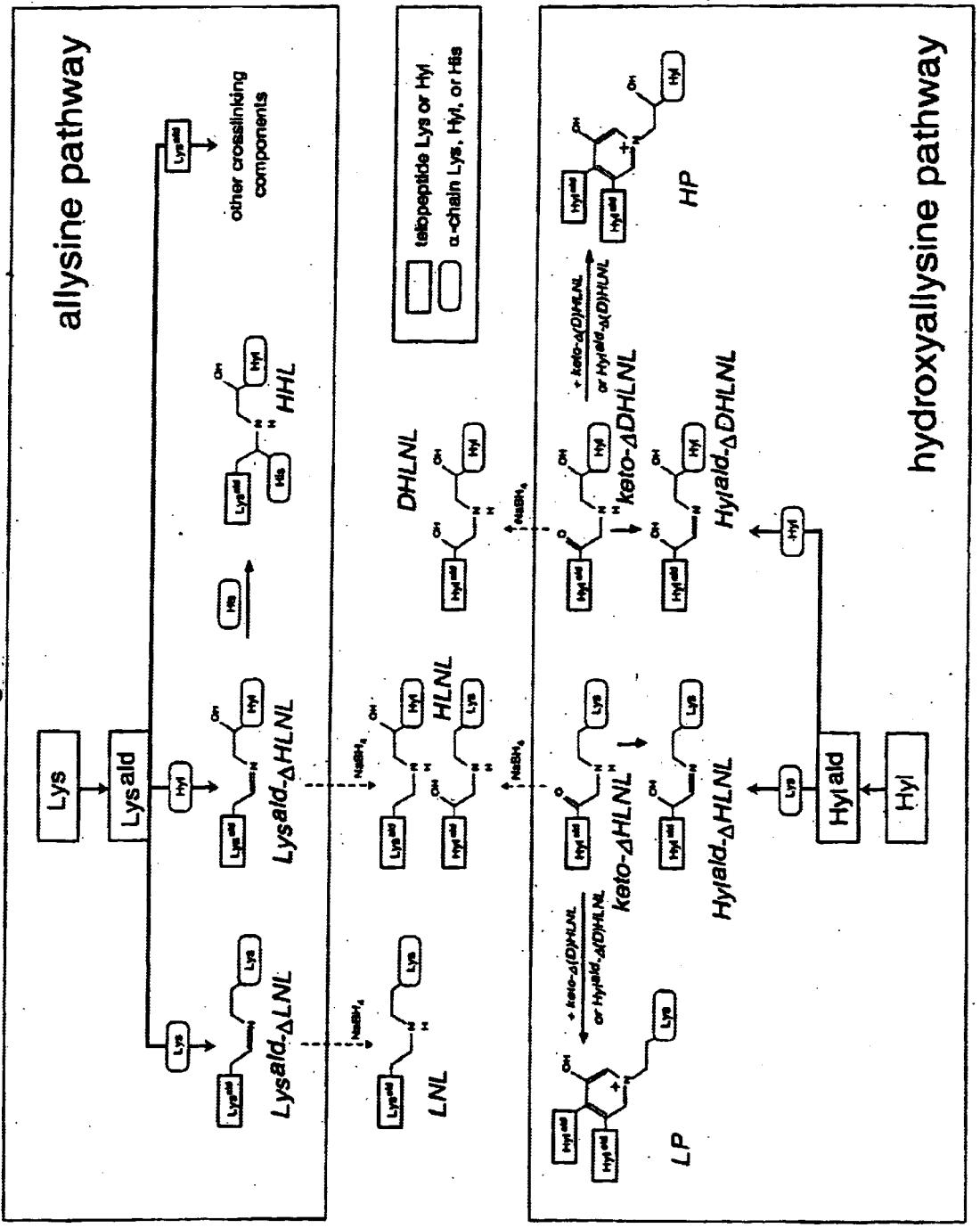
FIG. 2 is a diagram showing the reactions of telopeptidyl lysine (Lys) and hydroxylysine (Hyl) in collagen cross-link biosynthesis. Telopeptidyl Lys and Hyl are converted to aldehydes by lysyl oxidase into $Lys^{ald}$ and $Hyl^{ald}$, respectively. Crosslinks of the $Hyl^{ald}$ and $Lys^{ald}$ pathway found in vivo are placed in horizontally and vertically shaded boxes, respectively. Dehydro-crosslinks are labile and require reduction with borohydride before measurement; the reaction products obtained after reduction with borohydride are placed outside the shaded areas. Abbreviations: DHLNL= dihydroxylysinonorleucine (reduction product of $Hyl^{ald}$-ΔDHLNL and keto-ΔDHLNL); HHL= histidinohydroxylysinonorleucine; HLNL= hydroxylysinonorleucine (reduction product of $Lys^{ald}$-ΔHLNL, Hyl -ΔHLNL and keto-ΔHLNL); HP=hydroxylysylpyridinoline; $Hyl^{ald}$=hydroxyallysine; $Hyl^{ald}$-ΔDHLNL=dehydro-dihydroxylysinonorleucine derived from hydroxyallysine; $Hyl^{ald}$-ΔHLNL=dehydro-hydroxylysinonorleucine derived from hydroxyallysine; keto-ADHLNL=hydroxylysino-5-ketonorleucine; keto-ΔHLNL=lysino-5-ketonorleucine; LNL=lysinonorleucine (reduction product of $Lys^{ald}$-ΔLNL); LP=lysylpyridinoline; $Lys^{ald}$=allysine; $Lys^{ald}$-ΔHLNL=dehydro-hydroxylysinonorleucine derived from allysine; $Lys^{ald}$-ΔLNL=dehydro-lysinonorleucine derived from allysine.

Interestingly, cross-link patterns showed at least a 10-fold decrease in the amounts of trifunctional cross-links hydroxylysylpyridinoline (HP) and lysylpyridinoline (LP) (Table 1; FIG. 4). Although the total amount of intermolecular difunctional cross-links is about half of that in normal bone (Table 1), substantial levels of lysinonorleucine (LNL), hydroxylysinonorleucine (HLNL) and dihydroxylysino-norleucine (DHLNL) were found (Table 1; FIG. 4). As the formation of cross-links is under strict stereochemical control, this implies that collagen molecules in the extracellular matrix meet the spatial requirements for cross-linking. The relative abundance of the difunctional cross-links was, however, completely different from that observed in normal bone (Table 1; FIG. 4): DHLNL was the minor cross-link (predominant in normal bone), HLNL was the major difunctional cross-link and LNL was highly elevated (a minor component—or even lacking—in normal bone). The very low levels of HP, LP and DHLNL, products from the hydroxyallysine pathway (FIG. 2), indicate a low degree of lysyl hydroxylation in the telopeptides, similar to the situation that normally occurs in skin and cornea collagens. The low lysyl hydroxylation level of telopeptides was substantiated by the elevated presence of LNL, the condensation product of a telopeptide allysine with a triple helical lysine (FIG. 2), but also by the presence of HLNL. Essentially, HLNL can be derived from both cross-link pathways (FIG. 2). Smith degradation of HLNL in Bruck syndrome bone revealed that about 95% was derived from allysine. In contrast, in normal bone the majority of HLNL results from the hydroxyallysine cross-link route. Only small amounts of the non-reducible cross-link histidino-hydroxylysinonorleucine (HHL) were detected in the affected bone (Table 1). Apparently, the presence of the allysine cross-linking pathway in Bruck syndrome bone was not accompanied by maturation to HHL as in skin and cornea collagen [M. Yamauchi et al., 1996, Biochem. Biophys. Res. Commun., 219: 311–315]. Ligament (a tissue that contains, like bone, predominantly collagen type I) showed a normal HP level in Bruck syndrome (Table 2; FIG. 5). The same was observed in cartilage, a tissue containing predominantly collagen type II (Table 2; FIG. 5). As in bone, lysyl hydroxylation of the triple helix of collagen in ligament and cartilage was normal (Table 2; FIG. 5).

In conclusion, in Bruck syndrome lysine residues within the telopeptides of collagen type I in bone are underhydroxylated, leading to aberrant cross-linking, but the lysine residues in the triple helix are normally modified. In contrast to bone, cartilage and ligament show unaltered telopeptide hydroxylation as evidenced by normal patterns of cross-linking. Thus it was established that the Bruck syndrome provides compelling evidence that collagen cross-linking is regulated primarily by tissue-specific enzymes that hydroxylate only telopeptide lysine residues and not those destined for the helical portion of the molecule.

A genome-wide screen of a Bruck syndrome family with 244 DNA markers revealed that the disease locus is located on chromosome 17 to a region of maximally 18 cM at 17p12. This excludes the three lysyl hydroxylase genes encoded by PLOD1, PLOD2 and PLOD3 as candidate genes, as they are located on chromosome 1, 3 and 7, respectively.

A wide variety of mutations in Ehlers-Danlos type VI syndrome revealed that the lysyl hydroxylase encoded by PLOD1 is a helical lysyl hydroxylase [B. Steinmann et al., 1995, Am. J. Hum. Genet., 57: 1505–1508] (SEQ ID NO. 1–6). The substrate specificity of the lysyl hydroxylase encoded by PLOD2 (SEQ ID NO. 7–12) and PLOD3 (SEQ ID NO. 13–16) is not known; the only substrate studies performed on both enzymes are incubations with a peptide with a helical sequence. Both enzymes were capable of hydroxylating this helical sequence. Expression studies revealed circumstantial evidence that the lysyl hydroxylase encoded by PLOD2, but not PLOD3, is involved in the hydroxylation of telopeptides. More specifically, PLOD2 expression is associated with lysine hydroxylation in the telopeptides of collagen [K. Uzawa et al., 1999, J. Bone Miner. Res., 14: 12721280], an observation that correlates with earlier findings with respect to cross-link levels and expression levels of PLOD2 [R. J. Fernandes et al., 1998, Transact. Orthop. Res. Soc., 44: 933]. Thus, PLOD2 expression seems to be (partially) responsible for the tissue-specific collagen hydroxyallysine cross-linking pattern. PLOD2 (SEQ ID NO. 7–12) shows an overall amino acid identity of 75% with that of PLOD1, and shows the same reaction mechanism as PLOD1 with respect to the decarboxylation of 2-oxoglutarate [M. Valtavaara et al., 1997, J. Biol. Chem., 272: 6831–6834]. A tissue-specific distribution of two different splice forms of PLOD2 has been reported [H. N. Yeowell & L. C. Walker, 1999, Matrix Biology, 18: 179–187]. Interestingly, in another Bruck syndrome family, the disease locus was not linked to chromosome 17, but was linked to chromosome 3 to the region where PLOD2 is located. Consequently, in this family, PLOD2 is a candidate gene, indicating that the lysyl hydroxylase encoded by PLOD2 is a telopeptidyl lysyl hydroxylase. Thus, the Bruck syndrome provides the first genetic evidence that PLOD2 is a telopeptide lysyl hydroxylase Bruck Syndrome Provides Evidence That Allysine Cross-linked Collagen Molecules are More Easily Degraded by Proteolytic Enzymes As shown in the preceding section, the hydroxyallysine cross-links of normal bone are in Bruck syndrome bone replaced by allysine cross-links. Since Bruck syndrome patients are osteoporotic (an indication of increased collagen degradation), we investigated whether this change in cross-link pattern results in increased bone turnover. Therefore, urinary excretion of hydroxyproline (Hyp), galactosylhydroxylysine (GHyl) and glucosylgalactosylhydroxylysine (GGHyl) was measured in order to assess rates of bone collagen degradation. Indeed, a significant increase was found in urinary excretion rates of said collagen degradation products of Bruck syndrome patients compared to age-matched controls (FIG. 4). To corroborate further that allysine cross-linked collagen molecules are more prone to degradation by proteolytic enzymes, both demineralized Bruck syndrome (containing allysine cross-links) and demineralized control bone (containing hydroxyallysine cross-links) were treated with pepsin dissolved iri 0.5 M acetic acid. Demineralized Bruck syndrome bone treated with pepsin resulted in a release of 65% of the collagen molecules (compared to 5% of normal bone). Treatment of demineralized Bruck syndrome bone as well as demineralized control bone in 0.5 M acetic resulted in the solubilization of 7% and 1% of the collagen molecules, respectively, indicating that the value of 65% released collagen is mainly due to the action of pepsin.

In conclusion, we have shown that collagen molecules cross-linked by allysine are both in vitro and in vivo more prone to proteolytic degradation. This explains the high excretion of collagen degradation products in urine of Bruck syndrome patients and consequently the osteoporotic status of the patients.

Bruck Syndrome Provides Evidence That Allysine and Hydroxyallysine Cross-linked Collagen Molecules Show a Different Packing Within Collagen Fibrils Intermolecular cross-linking of collagen involves a few specific amino acids only. For steric and chemical reasons only these amino acids are able to react with each other when collagen molecules are correctly aligned. Consequently, variations in the packing arrangement must have an impact on the amount and nature of cross-links, or vice versa. In either case, cross-link patterns can be used as a marker to probe the alignment of intrafibrillar collagen molecules. X-ray diffraction studies revealed that collagen molecules cross-linked by HHL (an allysine cross-link) show a different tilting of collagen molecules along the axis of the fibril [J. Brinckmann et al., 1996, J. Invest. Dermatol., 107: 589–592]. It has been argued that this is the result of the specific properties of HHL [M. Yamauchi et al., 1996, Biochem. Biophys. Res. Commun., 219: 311–315].

In Bruck syndrome, no significant amounts of HHL are present in bone. Interestingly, pepsinized collagen from Bruck syndrome bone (containing predominantly allysine cross-links) show on SDS-electrophoresis two β-bands (β1,1 and β1,2 in a 1:2 ratio) whereas pepsinized collagen from normal bone (containing predominantly hydroxyallysine cross-links) show on SDS-electrophoresis three β-bands (β1,1, β1,2 and β2,2 in a 1:1:1 ratio). The β-bands are two α-chains connected to one another by means of a difunctional cross-link. It occurs to us that the difference in β-band patterns after pepsinization is the result of a different packing of the collagen molecules. We conclude that allysine cross-links give rise to a packing of collagen molecules within fibrils that is different from the packing that results from hydroxyallysine cross-links, and that this is a general feature (e.g., it is not restricted to HHL). We postulate that this difference in packing is causally involved in the observed increased degradation rate of allysine cross-linked collagen.

Telopeptide Lysyl Hydroxylase is a key Enzyme in Fibrosis

Note: Numbers between square brackets refer to references cited in Appendix 1 ("References showing that hydroxyallysine cross-links are increased in fibrosis/scarring").

In abnormal wound healing of the skin, such as in hypertrophic scarring, large amounts of hydroxyallysine-derived cross-links (such as DHLNL) are seen [1–6]. A predominance of DHLNL is also found in collagen produced after wounding of the corneal stroma; the resulting scar show markedly increased levels of hydroxyallysine derived cross-links at the expense of allysine cross-links [7]. The pioneering studies on elevated hydroxyallysine-derived cross-links in abnormal scarring were later confirmed [8–12], followed by reports on increased hydroxyallysine-derived cross-links in other (mainly fibrotic) disorders, such as various lung diseases (respiratory distress syndrome, idiopathic pulmonary fibrosis, hypersensitivity pneumonitis, respiratory bronchiolitis, silicosis and bleomycin-induced lung fibrosis) [13–22], chronic adriamycin nephropathy (an experimental model resulting in non-immunologic glomerulosclerosis and interstitial fibrosis) [23], infarct scar of the myocardium [24], joint contractures [25], vessel luminal narrowing [26]; lipodermatosclerosis [27], annulo-aortic ectasia [28], fibrotic lesions of Dupuytren's disease [29], skin of patients with lipoid proteinosis [30], diabetes [31–32], skin fibrosis due to chromoblastomycosis infection [33–34], skele muscle injury [35], tendon hypertrophy [36] and various liver diseases such as in alveolar echinococcosis (a dense and irreversible fibrosis), hepatocellular carcinoma, alcoholic cirrhosis or cirrhotic livers induced by viral hepatitis or by Schistosoma mansoni [37–44]. From this abundance of data on elevated hydroxyallysine cross-link levels in fibrotic tissues, in combination with our finding that tissue-specific telopeptide lysyl hydroxylase exists, we conclude that one of the characteristics of fibrotic lesions is an upregulation of telopeptide lysyl hydroxylase (FIG. 7).

In recent years, it has been suggested that the relative (and absolute) amount of hydroxyallysine cross-links are adequate biomarkers for the accumulation of collagen in lung and liver fibrosis [13, 15–18, 20–22, 38–40]. As the same is seen in other fibrotic tissues (such as skin and kidney), it was actually stated that "It is possible that organ fibrosis is a unique process ultimately associated with a change in cross-linking whereby the proportion of the allysine cross-links decreases in favor of the hydroxyallysine-derived crosslinks" [27]. Thus, hydroxyallysine cross-links are implicated in the pathogenesis of fibrosis. As a matter of fact, hydroxyallysine cross-link levels might be an important criterion in assessing the irreversibility of fibrosis. The validity of this statement is strengthened by cross-link patterns seen in acute (self-limiting) and progressive forms of fibrosis. Collagen produced in response to an injury of skin is initially stabilized by DHLNL [1–5], a cross-link derived from hydroxyallysine. In the early stages of wound healing, the collagen of both forms of fibrosis possess DHLNL as the major cross-link, but after a few months there is an approximately equal proportion of HLNL. Subsequently, acute and progressive fibrosis follow a different course. In hypertrophic scars, a progressive form of skin fibrosis, the 1:1 ratio of the two cross-links is retained. In contrast, the cross-link pattern in the self-limiting form of fibrosis gradually reverts to normal, i.e. there is a virtual disappearance of hydroxyallysine derived cross-links and replacement by allysine derived cross-links. In addition, the HLNL of old hypertrophic scars is derived from hydroxyallysine, and therefore stabilized by undergoing the Amadori rearrangement. The HLNL of normal scars is like normal dermis in being almost entirely derived from allysine [3, 5–6].

Clearly, fibroblasts in fibrotic tissues are fundamentally different from normal fibroblasts: fibrotic fibroblasts synthesize collagen with increased hydroxylysine levels of the telopeptides. Such collagen is destined to become irreversibly incorporated into the collagen network of the tissue by means of hydroxyallysine cross-links. The fact that HP, the maturation product of DHLNL, might serve as a permanent marker of a fibrotic event indicates that such cross-linked collagen molecules show a negligible rate of degradation. We conclude from the foregoing that controlling the telopeptide lysyl hydroxylation level is a central event in the pathogenesis of fibrosis (FIG. 7). As we found that hydroxylation of the telopeptide lysine is controlled by tissue-specific telopeptide lysyl hydroxylases, we conclude that telopeptide lysyl hydroxylase is a key enzyme in fibrosis.

Telopeptide Lysyl hydroxylase is an Attractive Target for Inhibition of Fibrosis as Inhibition of This Enzyme Selectively Inhibits Unwanted Hydroxvalivsine Cross-links in Wound Repair Without Affecting Allysine Cross-link Formation in the Surrounding Intact Tissues Correctly processed collagens contain a large condensed structure, known as the triple helix, which is resistant to cleavage by a variety of proteolytic enzymes. The resistance of collagen towards proteinases is enhanced when individual collagen molecules are assembled into fibrils; aggregation of collagen molecules into such fibrils is accompanied by the formation of covalent cross-links between the individual α-chains. Increasing the amount of cross-links results in an increased resistance of the fibril towards degradation by mammalian collagenase [C. A. Vater et al., 1979, Biochem. J., 181: 639–645]. Irihibition of cross-linking (in order to enhance proteolysis of collagen) has been considered a potential target in the treatment of fibrosis. Toxicity is the main reason why cross-linking-inhibiting drugs (lathyrogens; penicillamine), though effective antifibrotic drugs, never became a clinical modality [M. E. Nimni, 1983, Sem. Arthr. Rheum., 13: 1–86].

As has been stated in the previous section, an important aspect of fibrosis is the problem of irreversibility of collagen deposition. Remarkably, the effects of the type of crosslinks on the susceptibility of collagen to proteolytic enzymes has never been investigated, despite the fact that the presence of hydroxyallysine-derived cross-links is indicative for irreversible collagen deposition. As we have shown above, collagen molecules cross-linked by hydroxyallysine are less susceptible to degradation by proteolytic enzymes. The reduced proteolytic turnover of hydroxyallysine cross-linked collagen explains, at least in part, the irreversibility of collagen deposition. This resistance towards proteolytic enzymes is most probably caused by a changed packing of collagen molecules within the fibrils. Indeed, it has been demonstrated that the mode of packing of collagen molecules within the fibrils is dictated by the type of cross-links [M. Yamanuchi & E.P. Katz, 1993, Connect. Tissue Res., 29: 81–98]. Altogether, the data indicate that the type of cross-links provide a mechanism for regulating the rate of collagen catabolism: collagen with hydroxyallysine cross-links are less susceptible to proteolytic degradation than collagen cross-linked by allysine residues. Thus we found that inhibition of telopeptide lysyl hydroxylase (to enhance the formation of allysine cross-links at the expense of hydroxyallysine cross-links) is an attractive target for inhibition of fibrosis (FIG. 7).

Presently explored targets to inhibit collagen accumulation in fibrosis include inhibition of: transcription of collagen genes, translation of the mRNAs, hydroxylation of proline by prolyl hydroxylase, hydroxylation of triple helical lysine by helical lysyl hydroxylase, and/or cross-link formation. A drawback of all these approaches is, that unphysiological collagen is produced in wound healing, resulting in new tissue with impaired functional properties. In addition, physiological collagen production/modification in the healthy tissue surrounding the injury is affected as well. We believe that agents capable of regulating the expression or activity of telopeptide lysyl hydroxylase (which is upregulated in fibrosis/scarring) are potential antifibrotic drugs and do not exhibit these drawbacks. The rationale for this new therapeutic approach to fibrosis is based on the consideration that collagen deficient in hydroxyallysine cross-links is deposited in the extracellular matrix as a protein with increased susceptibility to proteinases. Since synthesis of telopeptide lysyl hydroxylase is upregulated in fibroblasts involved in wound healing, whereas normal fibroblasts do not express this enzyme, such agents are expected to selectively inhibit the formation of unwanted cross-links in collagen of the fibrotic lesions, leaving the intact tissue unaffected. In addition, the deposited collagen in the wound area is expected to be normally modified, and thus have the properties (e.g. with respect to tensile strength) required for normal function of the repaired tissue. This makes telopeptide lysyl hydroxylase a very attractive target for the inhibition of fibrosis/scarring.

Compounds Capable of Selectively Inhibiting Telopeptide Lysyl Hydroxylase

Prolyl hydroxylase and lysyl hydroxylase have very similar catalytic properties (e.g. they share the same co-substrates). In addition, the inhibition patterns of prolyl and lysyl hydroxylases are very similar as well, but differences exist in some details, suggesting that significant differences exist between the catalytic sites of said hydroxylases. For example, K values of the aliphatic and aromatic 2-oxoglutarate analogues (see below) are distinctively higher for helical lysyl hydroxylase encoded by PLOD1 than for prolyl 3-hydroxylase and prolyl 4-hydroxylase. The data that have previously been obtained with respect to the inhibition of prolyl 3-hydroxylase, prolyl 4-hydroxylase and helical lysyl hydroxylase encoded by PLOD1 can thus be used for a knowledge-based design of inhibitors of telopeptide lysyl hydroxylase.

Lysyl hydroxylase acts on lysine in a reaction that requires ferrous ion ($Fe^{2+}$), 2-oxoglutarate, molecular oxygen ($O_2$) and ascorbate. The 2-oxoglutarate is stoichiometrically decarboxylated during hydroxylation with one atom of the $O_2$ being incorporated into succinate while the other is complexed to the enzyme-bound ferrous ion. The latter results in a highly reactive iron-oxygen complex, fenryl ion. The oxygen atom of the ferryl ion is subsequently incorporated into the hydroxy group formed on the lysine residue, thereby converting the ferryl ion to the enzyme-bound ferrous ion. In the absence of a hydroxylatable substrate, lysyl hydroxylase is able to catalyze the decarboxylation reaction of 2-oxoglutarate in the presence of all the co-substrates [G. Tschank et al., 1994, Biochem. J., 300: 75–79]. In this so-called uncoupled reaction, the ferryl ion is converted to $Fe^{3+}$ and $OH^-$, and the $Fe^{3+}$ion remains bound to the active site, making the enzyme unavailable for new catalytic cycles until the $Fe^{3+}$ is reduced back to $Fe^{2+}$ by ascorbate. The main role of ascorbate in the lysyl hydroxylase reaction in vivo is that of reactivating the enzyme after an uncoupled reaction [R. Myllyla et al., 1984, J. Biol. Chem., 259: 5403–5405]. As such, ascorbate plays a housekeeping role of restoring the iron constituent of the enzyme to the reduced state should it become oxidized adventitiously. The uncoupled reaction (and thus the oxidation of the iron) can be enhanced by peptides containing an unhydroxylatable sequence [D. F. Counts et al., 1978, Proc. Natl. Acad. Sci. USA, 75: 2145–2149; N. V. Rao & E. Adams, 1978, J. Biol. Chem., 253: 6327–6330].

The enzymatic reaction that converts telopeptide lysine into hydroxylysine can be used for the design of compounds that inhibit the activity of telopeptide lysyl hydroxylase. Potential inhibitors are:

Compounds (such as aliphatic and aromatic structural analogues of 2-oxoglutarate) that bind to the subsite(s) of the active site of the enzyme destined for the binding of 2-oxoglutarate. The inhibition of telopeptide lysyl hydroxylase activity by said compounds is competitive with respect to 2-oxoglutarate. A selective compound is a compound that preferentially competes for 2-oxoglutarate in the active site of telopeptide lysyl hydroxylase but not for 2-oxoglutarate in the active site of helical lysyl hydroxylase and prolyl hydroxylase.

Compounds that chelate $Fe^{2+}$ bound in the active site of telopeptide lysyl hydroxylase. The inhibition of telopeptide lysyl hydroxylase activity by said compounds is competitive with respect to the oxygen atom acceptor function of $Fe^{2+}$ and/or with respect to the binding of $Fe^{2+}$ to 2-oxoglutarate. A selective compound is a compound that preferentially chelates $Fe^{2+}$ bound in the active site of telopeptide lysyl hydroxylase but not $Fe^{2+}$ bound in the active site of helical lysyl hydroxylase and prolyl hydroxylase.

Syncatalytic inactivation of telopeptide lysyl hydroxylase by anthracyclines or coumalic acid analogues. A selective compound is a compound that preferentially inactivates telopeptide lysyl hydroxylase, but not helical lysyl hydroxylase and prolyl hydroxylase.

Syncatalytic inactivation of telopeptide lysyl hydroxylases by peptides or peptidomimetics containing an unphysiologic lysine derivative in a hydroxylatable position. A selective compound is a compound that preferentially inactivates telopeptide lysyl hydroxylase, but not helical lysyl hydroxylase and prolyl hydroxylase.

Hydroxylatable peptides or peptidomimetics that are competitive to the natural substrate (telopeptides) of telopeptide lysyl hydroxylase. A selective peptide or peptidomimetic is much less competitive with respect to the natural substrate (nascent α-chains) of helical lysyl hydroxylase and prolyl hydroxylase.

Non-hydroxylatable peptides or peptidomimetics that are competitive with respect to the natural substrate (telopeptides) of telopeptide lysyl hydroxylase. A selective peptide or peptidomimetic is much less competitive with respect to the natural substrate (nascent α-chains) of helical lysyl hydroxylase and prolyl hydroxylase.

The uncoupled reaction of lysyl hydroxylase can be used for the design of compounds that inhibit the activity of telopeptide lysyl hydroxylase. Potent compounds are:

Non-reducing ascorbate analogues that bind to the enzyme's active site but are not able to act as a specific alternative acceptor of ferryl oxygen. The presence of such a compound in the active site instead of an ascorbate (or an ascorbate analogue capable of reducing the ferryl ion) results in the inactivation of the enzyme by self-oxidation. The inhibition of telopeptide lysyl hydroxylase activity by said non-reducing ascorbate analogues is competitive with respect to ascorbate. A good candidate compound is a compound that selectively binds to the active site of telopeptide lysyl hydroxylase, but not to the active site of helical lysyl hydroxylase and prolyl hydroxylase.

Peptides or peptidomimetics with an unhydroxylatable sequence, capable of enhancing the uncoupled reaction of telopeptide lysyl hydroxylase but not helical lysyl hydroxylase or prolyl hydroxylase. Said inhibitors result in increased levels of self-oxidized (non-active) levels of telopeptide lysyl hydroxylase. A good candidate fits within the active site of telopeptide lysyl hydroxylase, but not in the active site of helical lysyl hydroxylase and prolyl hydroxylase.

A large number of studies have been published with respect to the inhibition of prolyl hydroxylase and helical lysyl hydroxylase by means of peptides or other compounds. What follows are a few selected examples of studies that can be used as a starting point in the design of selective inhibitors for telopeptide lysyl hydroxylase. Examples of syncatalytic inactivation by peptides: V. Günzler et al., 1988, J. Biol. Chem., 263: 19498–19504; K. Karvonen et al., 1990, J. Biol. Chem., 265: 8145–8419. Examples of syncatalytic inactivation by coumalic acid and anthracyclines: V. Günzler et al., 1987, Biochem. J., 242: 163–169; V. Günzler et a/., 1988, Biochem. J., 251: 365–372. Examples of inhibitory competitive analogues of 2-oxoglutarate and ascorbate: K. Majamaa et al., 1984, Eur. J. Biochem., 138: 239–245; K. Majamaa et al., 1985, Biochem. J., 229: 127–133; K. Majamaa et al., 1986, J. Biol. Chem., 261: 7819–7823. Examples of conformational requirements of lysyl hydroxylatable peptides: P. Jiang & V. S. Ananthanarayanan, 1991, J. Biol. Chem., 266: 22960–22967.

Besides the knowledge-based design of inhibitors of telopeptide lysyl hydroxylase described above, a search can be performed with synthetic libraries of compounds (combinatorial chemistry) in order to find compounds that preferentially inhibit the activity of telopeptide lysyl hydroxylase, but not helical lysyl hydroxylase or prolyl hydroxylase.

Antibodies Capable of Selectively Inhibiting Telopeptide Lysyl Hydroxylase

A further example of inhibition of the catalytic properties of telopeptide lysyl hydroxylase is the use of antibodies. Antibodies directed against the enzyme and capable of blocking the active site or inhibiting the hydroxylation by telopeptide lysyl hydroxylase otherwise are potential inhibitors for the telopeptide lysyl hydroxylation reaction. These antibodies, preferably monoclonal, can be generated by immunization of mice with synthetic peptides or peptidomimetics containing stretches of amino acids of telopeptide lysyl hydroxylase (such as PLOD2), in particular sequences around the residues responsible for the binding of $Fe^{2+}$or 2-oxoglutarate to the enzyme. Promising candidate peptides or peptidomimetics for the generation of inhibiting antibodies are likely to be derived from sequences encompassing the last 60 residues at the carboxy-terminal end of the enzyme (i.e. the region containing the conserved residues known to play a role in the catalytic properties of lysyl hydroxylase 1). Monoclonal antibodies can also be generated by screening phage display libraries for their ability to block the activity of telopeptide lysyl hydroxylase. Antibodies not directed to the active site but directed against parts of the enzyme that are important for substrate binding are also potent inhibitors of the enzymatic reaction. In addition, antibodies directed towards the collagen telopeptides are also expected to inhibit the hydroxylation reaction of telopeptide lysyl hydroxylase, namely by means of steric hindrance.

Compounds Capable of Selectively Inhibiting the Transcription of Telopeptide Lysyl Hydroxylase Another approach to inhibit the conversion of telopeptide lysine into hydroxylysine is the inhibition of transcription of the responsible telopeptide lysyl hydroxylase gene. A compound capable of preferentially silencing the promotor region of telopeptide lysyl hydroxylase is a potentially attractive compound for inhibiting fibrosis. Compounds worthwhile to investigate are minoxidil analogues, compounds known to inhibit the transcription of the PLOD1 gene, but not the genes encoding for prolyl 4-hydroxylase [S. Murad et al., 1994, Arch. Biochem. Biophys., 308: 42–47]. Compounds that are capable of preferentially suppressing the transcription of telopeptide lysyl hydroxylase but not helical lysyl hydroxylase are selective compounds for the inhibition of the reaction involving conversion of telopeptide lysine into hydroxylysine.

Tools to be Used in Gene Therapy Resulting in Selectively Inhibiting Translation or Activity of Telopeptide Lysyl Hydroxylase A further approach to inhibit the synthesis of telopeptide lysyl hydroxylase (such as PLOD2) is the inhibition of mRNA translation by means of antisense RNA (the transcription product of the DNA antisense strand, i.e. the strand that does not encode a protein). For the cDNA sequence of the protein-coding part of PLOD2 see FIG. 9.

In yet another approach to inhibit the conversion of telopeptide lysine into hydroxylysine, local gene therapy can be carried out. Localized, direct plasmid gene delivery can e.g. be achieved from plasmid genes physically entrapped in a polymer matrix [J. Bonadio et al, 1999, Nature Medicine, 5: 753–759]. A good approach is the local delivery of constructs containing a telopeptidyl lysyl hydroxylase that is able to bind telopeptides but that is not capable to convert the lysine of the telopeptides into hydroxylysine. Such an exogenous telopeptide lysyl hydroxylase is competitive to endogenous telopeptide lysyl hydroxylase with respect to its natural substrate (telopeptides). For said construct nonfunctional telopeptide lysyl hydroxylase is used that is mutated by means of sitedirected mutagenesis. Candidate residues for site-directed mutagenesis are the residues that are needed for the full activity of helical lysyl hydroxylase [A. Pirskanen et al., 1996, J. Biol. Chem., 271: 9398–9402] and that are preserved in telopeptide lysyl hydroxylase (such as the one encoded by PLOD2). Especially interesting are the three ligands needed for the binding of Fe z+ to the catalytic site of lysyl hydroxylase (for helical lysyl hydroxylase encoded by PLOW this is His-638, Asp-640 and His-690; numbering begins with the first residue in the processed polypeptide) or the residue that is responsible for the binding of 2-oxoglutarate to the enzyme (which is Arg-700 for the helical lysyl hydroxylase encoded by PLOD1) (SEQ ID NO. 1–6). [K. Passoja et a/., 1998, FEBS Letters, 434: 145–148]. The same residues are conserved in PLOD2 (SEQ ID NO. 7–12)., which is a telopeptide lysyl hydroxylase. Residues that are also of potential interest are glycosylated Asn-X-Thr/Ser sequences: glycosylated lysyl hydroxylase encoded by PLOD1 has a higher activity than its de-glycosylated counterpart [R. Myllyla et aL, 1988, Biochem. J., 253: 489–496]. It thus seems that asparagine-linked oligosaccharides are required to obtain maximum lysyl hydroxylase activity. Two potential attachment sites for asparagine-linked oligosaccharides of the lysyl hydroxylase encoded by PLOD2 have an identical location in the sequence of the helical lysyl hydroxylase encoded by PLOD1. Other residues of potential interest are the cysteines of lysyl hydroxylase 2. All mentioned residues in this section that are of special interest with respect to inhibiting the activity of the telopeptide lysyl hydroxylase encoded by PLOD2 are shown in bold in the sequence of PLOD2 (FIG. 9).

EXAMPLES

Example 1

Bruck Syndrome Provides Genetic Evidence for the Existence of Telopeptide Lysyl Hydroxylase: Measurement of Hydroxylysine and Cross-link Levels in bone (Glycosylated) hydroxylysine and cross-link measurements were carried out with cortical Bruck syndrome bone (subject DaF,.female, 13 year=patient 507 or case 1 of E. J. Breslau-Siderius et a., 1998, J. Pediatr. Orthop. B, 7: 35–38), trabecular Bruck syndrome bone (subject DoF, female, 8 year =patient 505 or case 2 of said reference), and normal cortical bone (male, 14 year). In addition, cortical bone was obtained from a 4 year old boy (patient 3 =case 8 of said reference) of an unrelated Kurdish family with two children diagnosed as Bruck syndrome. Bone samples were demineralized (0.5 M EDTA in 0.05 M Tris pH 7.5; 2 weeks at 4° C.) and subsequently hydrolyzed in 6 M HCI (110° C., 20–24 h) in Teflon sealed glass tubes. After drying in a SpeedVac the hydrolysates were dissolved in water containing the internal standard pyridoxine (10 $\mu$M) and homoarginine (2.4 mM). Samples were diluted 5-fold with 0.5% (v/v) heptafluorobutyric acid in 10% (v/v) acetonitrile for pyridinoline analysis; aliquots of the 5-fold diluted samples were diluted 50-fold with 0.1 M sodium borate buffer pH 8.0 for amino acid analysis. Derivatization of the amino acids with 9-fluorenylmethyl chloroformate and reversed phase HPLC of the amino acids hydroxyproline (Hyp) and hydroxylysine (Hyl) as well as the cross-links hydroxylysylpyridinoline (HP) and lysylpyridinoline (LP) was performed on a Micropak ODS-80TM column (150×4.6 mm) as described previously [R. A. Bank et al., 1996, Anal. Biochem., 240: 167–176; R. A. Bank et aL, 1997, J. Chromatogr. B, 703: 37–44]. The amount of Hyl, HP and LP was expressed as number of residues per collagen molecule, assuming 300 Hyp residues per triple helix. The hydroxylysine glycosides galactosyl-hydroxylysine (G-Hyl) and glucosylgalactosyl-hydroxylysine (GG-Hyl) were determined after derivatization with 9-fluorenylmethyl chloroformate with reversed-phase high-performance liquid chromatography (RP-HPLC) in alkaline hydrolysates (2 M NaOH, 110° C.; 20–24 h) as described previously [R. A. Bank et al., 1997, J. Chromatogr. B, 703: 267–272] and was expressed as number of residues per collagen molecule, assuming 300 Hyp residues per triple helix.

For the determination of the reducible difunctional cross-links, bone samples of patient 505 and 507 as well as said control were reduced with $NaB^3H_4$ as described [S. P. Robins, 1982, Meth. Biochem. Analysis, 28: 330–379]. In aliquots of the acid hydrolysates (6 M HCI; 108° C.; 18 h) Hyp was measured calorimetrically and the remaining sample was fractionated on a Sephadex G10 column with 0.4 M acetic acid as eluent to remove the bulk of the amino acids. The higher-Mr fraction was analyzed by ion-exchange chromatography (IEC) with 0.225 M sodium citrate buffer, pH 4.7. The cross-links were identified by their chromatographic elution positions on the analyzer and quantified by their $^3$H-radioactivity using the calculated specific radioactivity of isolated HLNL after quantification by IEC with post-column o-phtalaldehyde (OPA) detection. HHL was analyzed directly by IEC with OPA detection. The Hyp values were used to calculate the molar proportions of reducible cross-links in collagen assuming 300 Hyp residues per triple helical collagen molecule. To identify the chemical nature of HLNL, the collected radioactive cross-link was subjected to Smith degradation [S. P. Robins, 1982, Meth. Biochem. Analysis, 28: 330–379]. The amounts of radioactivity in proline and lysine, which reflects the proportion of HLNL in keto-amine or aldimine form, respectively, was measured after their separation by IEC with 0.35 M sodium citrate buffer, pH 4.7 and 0.2 M sodium citrate, pH 3.34.

Table 1 and FIG. 4 present the (glycosylated) hydroxylysine and cross-link data of collagen type I as determined in said bone samples (three Bruck syndrome patients and one control). The amount of Hyl, reflecting the lysyl hydroxylation of the triple helix, was normal in Bruck syndrome bone; the same was observed with respect to the level of the two glycosylated forms of Hyl, G-Hyl and GG-Hyl. Thus, in Bruck syndrome, helical lysyl hydroxylase and hydroxylysyl glycosyl transferases are normal; as a consequence, the collagen triple helix in Bruck syndrome bone is not different from that of normal bone. In contrast, collagen type I from Bruck syndrome bone (patient 3, 505 and 507) showed strongly reduced levels of the pyridinium cross-links HP and LP (a 10-fold decrease compared with control bone); both cross-links are derived from telopeptide Hyl residues. The levels of the difunctional cross-link DHLNL, another cross-link that originates from hydroxylated telopeptides, were also <10% of normal values. These findings indicate that hydroxylation of the lysine residues in the telopeptides is very low. Normal amounts of HLNL were found; this cross-link can result from both telopeptide Lys or Hyl. To corroborate further that the telopeptides in Bruck syndrome contain little Hyl, the origin of HLNL was determined by Smith degradation. The percentage of HLNL derived from hydroxylated telopeptides in Bruck syndrome was around 5%; in normal bone this is around 75%. The sum of telopeptidyl Hyl-derived cross-link per collagen molecule (HP, LP, DHLNL, part of the HLNL pool) in Bruck syndrome bone was 0.14, whereas in normal bone this is around 2. The low hydroxylation level of the telopeptides was further substantiated by the observed 5-fold elevation over normal levels for LNL, a crosslink derived from telopeptide lysyl residues. Apparently, the presence of the allysine cross-linking pathway in Bruck syndrome bone was not accompanied by maturation to HHL as in skin and cornea collagen.

In summary, the relative abundance of the different di- and trifunctional cross-links in Bruck syndrome bone was completely different from that observed in normal bone: there is a preponderance of cross-links derived from lysine in the telopeptides with very low levels of telopeptide Hyl-derived cross-links. The normal levels of Hyl in the triple helix indicate that the hydroxylation defect is limited to the telopeptides. Thus, patients with the Bruck syndrome lacks the enzyme that is capable of hydroxylating telopeptide lysyl residues. As such, the Bruck syndrome provides genetic evidence for the existence of telopeptide lysyl hydroxylase.

Example 2

Bruck Syndrome Provides Genetic Evidence for the Existence of Tissue-specific Telopeptide Lysyl Hydroxylases: Measurement of Hydroxylysine and Pyridinoline Levels in Ligament and Cartilage (Glycosylated) hydroxylysine and pyridinoline levels in Bruck syndrome joint ligament (mainly containing type I collagen) of patient 3 and Bruck syndrome articular cartilage (mainly containing type II collagen) from patient 507 as well as joint ligament and articular cartilage from a control were determined according to the methods outlined in Example 1.

Table 2 and FIG. 5 present the (glycosylated) hydroxylysine and cross-link data of collagen as determined in said joint ligament and articular cartilage samples. The amount of Hyl, reflecting the lysyl hydroxylation of the triple helix, was normal in Bruck syndrome tissues; the same was observed with respect to the level of the two glycosylated forms of Hyl, G-Hyl and GG-Hyl. Thus, in Bruck syndrome, helical lysyl hydroxylase and hydroxylysyl glycosyl transferases are normal; as a consequence, the collagen triple helix in Bruck syndrome joint ligament and articular cartilage is not different from that of normal joint ligament and articular cartilage the same situation was seen in bone samples from Bruck syndrome patients (see Example 1 and Table 1 as well as FIG. 4). In contrast to collagen type I from bone, collagen type I from ligament and collagen type II from articular cartilage showed normal pyridinium (HP and LP) levels. Thus, aberrant cross-linking is restricted to bone. The normal cross-linking in joint ligament and articular cartilage reflects a normal telopeptide lysyl hydroxylation in these tissues. Thus, Bruck syndrome provides genetic evidence for the presence of tissue-specific form of telopeptide lysyl hydroxylases: in Bruck syndrome only bone is affected.

Example 3

Bruck Syndrome Provides Genetic Evidence That the Gene of one of the Tissue-specific Telopeptide Lysyl Hydroxylases is Located on Chromosome 17

The existence of affected inbred Bruck syndrome individuals made the localization of the gene underlying this disorder a suitable target for homozygosity mapping. This mapping approach is based on the inheritance of two identical copies of the disease locus by the affected inbred child from a common ancestor, i.e., homozygosity by descent. Therefore, a genome-wide screen on DNA extracted from blood samples from five members of the consanguineous Bruck syndrome family (501, 502, 505, 507, 509; FIG. 8) described by Breslau-Siderus et al. [J. Pediatr. Orthop. B, 7: 35–38] was performed using 244 markers (average spacing 10 cM; average heterozygosity 0.75) from the Marshfield screening set, version 6 (http://www.marshmed.org) in order to locate the gene responsible for the cross-linking defect in bone. Reverse primers were labelled with either 6-FAM, HEX or TET fluorescent dyes, allowing analysis of a high density of markers. PCR reactions were carried out in PCR buffer II/2.5 mM $MgCl_2$ with Amplitaq Gold. DNA was initially denatured at 94° C. for 10 min, followed by 32 cycles of denaturation at 94° C. for 30 s, annealing at 55° C. for 30 s, elongation at 72° C. for 30 s. The final step consisted of an additional elongation step at 72° C. for 10 min. The reaction mixture was mixed with a GeneScan-500 standard and separated on non-denaturing 5% polyacrylamide gels. Gel images were analyzed using GeneScan 2.1; allele sizes of the individual markers were determined using Genotyper 2.0. For each of the 244 markers it was determined whether the three affected sibs (505, 507 and 509) were heterozygous of homozygous for the same marker alleles. Regions in which two or more consecutive markers showed homozygosity by state were studied further by (i) screening the four healthy sibs (503, 506, 508, 510) with the same markers, and (ii) haplotype analysis to determine whether the regions were also identical by descent. Multilod scores were calculated with conservative allele frequencies of 0.33 for alleles using LINKAGE, version 5.03 [G. M. Lathrop et al., 1985, Am. J. Hum. Genet., 37: 428–498].

Of 244 markers, 34 showed homozygosity by state in all three affected sibs; they were scattered throughout the genome. Clusters of two or more adjacent homozygous markers were identified on chromosomes 1, 2, 8, and 17 and were considered putative Bruck syndrome candidate regions needing further investigation. Haplotype analysis excluded the chromosomes other than 17 as a candidate region for the Bruck syndrome locus since the three affected sibs did not show identity by descent. The affected individuals were homozygous for D17S921 and D17S122 and haplotype analysis showed that the affected individuals, in contrast to the four healthy sibs, inherited two identical copies of that chromosomal region (i.e., homozygous by descent). Further investigation with two additional markers refined the position of the Bruck syndrome further. The telomeric border was defined by D17S969; the recombination event in patient 509 localized the Bruck syndrome locus to a region of maximally 18 cM at 17p12 (FIG. 8). This chromosomal location by haplotype analysis was in agreement with the results of the lod score analysis. The peak lod score was obtained at D17S1843 (Z=2.5).

In conclusion, the investigated Bruck syndrome family provides genetic evidence that one of the tissue-specific telopeptide lysyl hydroxylases is located on the p12 region of chromosome 17. The three cloned lysyl hydroxylase genes (PLOD1, 2 and 3) can therefore be excluded as candidate genes for Bruck syndrome in this family, as said genes are localized on chromosomes 1, 3 and 7, respectively.

Example 4

Bruck Syndrome Provides Genetic Evidence That the Lysyl Hydroxylase Encoded by PLOD2 is a Telopeptide Lysyl Hydroxylase In another consanguineous Bruck syndrome family of Kurdish orgin with 2 affected children but without healthy children (one of the children is case 8 of E. J. Breslau-Siderius et al., 1998, J. Pediatr. Orthop. B, 7: 35–38) no linkage was found with the markers of chromosme 17 that are shown in FIG. 8: haplotype analysis revealed that the affected children inherited different maternal chromosomes.

The lysyl hydroxylase encoded by PLOD2 is, according to Gene Map 98, located on chromosome 3 between the interval D3S1550 and D3S1306 (sex average 159.8 cM and 164.25 cM, respectively). Haplotype analysis was carried out of the parents and the two affected with the DNA markers D3S1764 (sex average 152.62 cM), D3S1512 (sex average 158.38 cM), D3S1744 (161.04 cM), D3S3618 (163.18 cM), D3S1594 (168.94 cM) and D3S1763 (176.54 cM). The affected individuals were homozygous for D3S1512, D3S1744, D3S3618 and D3S1594 and haplotype analysis showed that the affected children inherited two identical copies of that chromosomal region (i.e. homozygous by descent) (FIG. 10). Thus, a good linkage was found in this Bruck syndrome family and the chromosomal region where PLOD2 is located, making PLOD2 the candidate gene per excellence.

In conclusion, the Bruck syndrome family investigated in this Example provides genetic evidence that the lysyl hydroxylase encoded by PLOD2 is a telopeptide hydroxylase.

Example 5

Pepsin Digestion of Normal and Bruck Syndrome Bone Show Differences in Collagen Degradation by Proteolytic Enzymes and Differences in Collagen Packing BS and normal bone was demineralized at 4° C. with 0.5 M EDTA, 0.05 M Tris-HCl, pH 7.5 over 2 weeks. Demineralized BS and normal bone was incubated for 24 h at 4° C. with 0.5 M acetic acid (HAc) or with pepsin (enzyme:substrate ratio 1:10, w/w) in 0.5 M HAc. The solubilized collagen (present in the supernatant) was separated from the insoluble collagen matrix (containing the non-solubilized collagen) by means of centrifugation; both were hydrolyzed with 6 M HCl in Teflon sealed glass tubes (110° C., 20–24 h). The amount of the collagen-specific amino acid hydroxyproline (Hyp) was measured with reversed-phase high-performance liquid chromatography [R. A. Bank et al., 1997, Matrix Biol., 16: 233–243]. The amount of solubilized collagen was expressed as a percentage of total collagen using the equation $Hyp_{sup}/(Hyp_{res}+Hyp_{sup})\times 100\%$ where $Hyp_{sup}$ is the amount of Hyp in the supernatant and $Hyp_{res}$ the amount of Hyp in the residual tissue.

Collagen solubility in 0.5 M acetic acid was 7% and 1% for Bruck syndrome and normal bone, respectively. Treatment with pepsin resulted in the release of 65% of the collagen from Bruck syndrome bone, whereas treatment with pepsin resulted in the release on only 5% of the collagen from normal bone. Clearly, the collagen molecules in the fibrils in Bruck syndrome bone are more prone to degradation by proteinases. As the triple helix of collagen type I in Bruck syndrome is normally modified, the increased release of collagen by pepsin of Bruck syndrome bone seems to be due to the replacement of hydroxyallysine cross-links by allysine cross-links.

The pepsin-solubilized collagen of normal bone and Bruck syndrome bone was subjected to SDS-polyacrylamide gel electrophoresis and subsequently stained with Coomassie Brilliant Blue; the staining pattern of normal bone revealed three β-bands (β1,1, β1,2 and β2,2) whereas the staining pattern of Bruck syndrome bone revealed two β-bands (β1 and β1,2). The β-band patterns show that there are differences in the packing of intrafibrillar collagen molecules between normal and Bruck syndrome bone.

Example 6

In Vivo Degradation of Bone Collagen is Enhanced in Bruck Syndrome

Hydroxyproline and proline was determined in urine hydrolyzed in 6 M HCl (overnight, 110° C.). Urine was obtained from healthy subjects, patients with osteogenesis imperfecta, and patients with Bruck syndrome. After drying in a SpeedVac the urine hydrolysates were dissolved in 0.1 M borate buffer pH 9.5; the amount of Hyp and Pro was measured with reversed-phase high-performance liquid chromatography [R. A. Bank et al., 1997, Matrix Biol., 16: 233–243]. For the determination of galactosylhydroxylysine, native urine was diluted in 0.3 M carbonate buffer pH 9.5, derivatized with dansylchloride and subsequently fractionated on a reversed-phase column by means of high-performance liquid chromatography [K. Yoshihara et al., 1993, Biol. Pharm. Bull., 16: 604–607].

FIG. 6 shows that the urinary level of hydroxyproline (μmol hydroxyproline/mmol creatinine) is higher than age-related controls or age-related osteogenesis imperfecta patients ($P<0.001$), showing that there is an increase of collagen degradation. The same conclusion can be drawn from the elevated hydroxyproline over proline ratio, and the elevated urinary levels of galactosylhydroxylysine (μmol galactosylhydroxylysine/mmol creatinine). As galactosylhydroxylysine is mainly derived from bone collagen [L. Moro et al., 1989, J. Chromatogr., 490: 285–292], we can conclude that the degraded collagen molecules mainly originated from bone.

Example 7

Telopeptide Lysyl Hydroxylation and Cross-linking are Tissue-specific and age-related, an Observation That can be Used to Elucidate the Mechanism of Transcription/translation of Telopeptide Lysyl Hydroxylase The degree of hydroxylation of the telopeptides of a single collagen type (e.g. type I collagen) is not constant but differs as a function of tissue [M. J. Barnes et al., 1974, Biochem. J., 139: 461–468; M. J. Barnes et al., Biochem. J., 135: 433–437]. In addition, changes in the telopeptide hydroxylation level are seen within a single tissue as a function of developmental stage. For example, the telopeptides of type I collagen in embryonic skin contains high levels of Hyl, whereas low levels are seen in newborns followed by a complete loss of hydroxylation at a later age. Thus, a marked fall occurs with age in telopeptide lysine hydroxylation of collagen type I in skin. In contrast, no such decrease is seen in bone, showing that developmental changes are tissue-specific [M. J. Barnes et al., 1971, Biochem. J., 125: 925–928]. Since the level of telopeptide Lys hydroxylation is both age-related and tissue-specific, it follows that the type of cross-linking (as well as its abundance) is age-related and tissue-specific as well. Indeed, the cross-links in collagen type I in skin, cornea, and certain tendons are mainly derived from the allysine route whereas collagen type I in bone is predominantly stabilized by cross-links derived from the hydroxyallysine route [D. R. Eyre, 1987, Meth. Enzymol., 144: 115–139]. Furthermore, developmental differences in the type of cross-linking are seen within the same tissue. The differences in expression of telopeptide lysyl hydroxylase as a function of tissue or age can be explored to elucidate the identity of telopeptide lysyl hydroxylase(s) and the processes responsible for the transcriptional activation/inhibition of the telopeptide lysyl hydroxylase gene(s) or activationlinhibition of its translation. The same can be said for fibrogenic fibroblasts or other fibrogenic cells as compared to their normal counterparts.

TABLE 1

Lysyl hydroxylation and cross-linking in bone (collagen type I)

| | Residues per collagen molecule | | |
|---|---|---|---|
| amino acid | patient 505 | patient 507 | control |
| Hyl | 13.7 | 13.1 | 14.4 |
| G-Hyl | <0.8 | <0.8 | <0.8 |
| GG-Hyl | 4.3 | 3.9 | 3.7 |
| HP | 0.011 | 0.021 | 0.35 |
| LP | 0.002 | 0.007 | 0.09 |
| DHLNL | 0.10 | 0.08 | 0.92 |
| HLNL | 0.55 | 0.33 | 0.52 |
| LNL | 0.20 | 0.14 | 0.03 |
| % HLNL (Hyl) | 4% | 6% | 75% |

TABLE 2

Lysyl hydroxylation and cross-linking in ligament and bone

| | Residues per collagen molecule | |
|---|---|---|
| amino acid | ligament (collagen type I) Bruck/control | cartilage (collagen type II) Bruck/control |
| Hyl | 20.5/21.3 | 42.4/43.7 |
| G-Hyl | not determined | 8.2/9.6 |
| GG-Hyl | not determined | 12.5/10.4 |
| HP | 0.28 ± 0.41 | 1.2/1.6 |
| LP | 0.018/0.020 | 15.6/20.5 |

APPENDIX 1: REFERENCES SHOWING THAT HYDROXYALLYSINE CROSS-LINKS ARE INCREASED IN FIBROSIS/SCARRING

[1] L. Forrest, A. Shuttleworth, D. S. Jackson & G. L. Mechanic (1972): A comparison between the reducible intermolecular crosslinks of the collagen from mature dermis and young dermal scar of the Guinea pig. —Biochem. Biophys. Res. Commun., 46: 1776–1781.

[2] A. J. Bailey, S. Bazin & A. Delauny (1973): Changes in the nature of the collagen during development and resorption of granulation tissue. —Biochim. Biophys. Acta, 328: 383–390.

[3] A. J. Bailey, S. Bazin, T. J. Sims, M. le Lous, C. Nicoletis & A. Delauny (1975): Characterization of the collagen of human hypertrophic and normal scars. —Biochim. Biophys. Acta, 405: 412–421.

[4] M. J. Bames, L. F. Morton, R. C. Bennett, Bailey A. J. & T. J. Sims (1976): Presence of type III collagen in Guinea-pig dermal scar. —Biochem. J., 157: 263–266.

[5] S. Bazin, M. le Lous & A. Delaunay (1976): Collagen in granulation tissues. —Agents and Actions, 6: 272–276.

[6] A. J. Bailey & N. D. Light (1985): Intermolecular cross-linking in fibrotic collagen. —Ciba Found. Symp., 114: 80–96.

[7] D. J. Cannon & C. Cintron (1975): Collagen cross-linking in comeal scar formation. —Biochim. Biophys. Acta, 412: 18–25.

[8] T. Moriguchi & D. Fujimoto (1979): Crosslink of collagen in hypertrophic scar. —J. Invest. Dermatol., 72: 143–145.

[9] K. C. Wan & W. H. P. Lewis (1996): Study of free iron and pyridinoline in hypertrophic scars and normal skin. —Br. J. Biomed. Sci., 53: 196–203.

[10] K. Uzawa, M. K. Marshall, E. P. Katz, H. Tanzawa, H. N. Yeowell & M. Yamauchi (1998): Altered posttranslational modifications of collagen in keloid. —Biochem. Biophys. Res. Commun., 249: 652–655.

[11] K. C. Wan & J. H. Evans (1999): Free radical involvement in hypertrophic scar formation. —Free Radic. Biol. Med., 26: 603–608.

[12] O. V. Podobed, N. N. Prozorovskii, E. A. Koziov, T. A. Tsvetkova, S. 1. Vozdvizhenskii & A. A. Del'vig (1996): Comparative study of collagen in hypertrophic and keloid cicatrix. —Vopr. Med. Khim., 42: 240–245. [Article in Russian]

[13] J. E. Gerriets, K. M. Reiser, J. A. Last (1996): Lung collagen cross-links in rats with experimentally induced pulmonary fibrosis. —Biochim. Biophys. Acta, 1316: 121–131.

[14] K. M. Reiser & J. A. Last (1986): Collagen crosslinking in lungs of rats with experimental silicosis. —Collagen Rel. Res., 6: 313–324.

[15] K. M. Reiser, A. F. Tryka, R. C. Lindenschmidt, J. A. Last & H. R. Witschi (1986): Changes in collagen crosslinking in bleomycin-induced pulmonary fibrosis. —J. Biochem. Toxicil., 1: 83–91.

[16] K. M. Reiser, W. S. Tyler, S. M. Hennessy, J. J. Dominguez & J. A. Last (1987): Long-term consequences of exposure to ozone. II. Structural alterations in lung collagen of monkeys. —Toxicol. Appl. Pharmacol., 89: 314–322.

[17] K. M. Reiser & J. A. Last (1987): A molecular marker for fibrotic collagen in lungs of infants with respiratory distress syndrome. —Biochem. Med. Metab. Biol., 37: 16–21.

[18] J. A. Last, T. E. King, A. G. Nerlich & K. M. Reiser (1990): Collagen cross-linking in adult patients with acute and chronic fibrotic lung disease. Molecular markers for fibrotic collagen. —Am. Rev. Respir. Dis., 141: 307–313.

[19] J. A. Last, J. E. Gerriets, L. C. Armstrong, T. R. Gelzleichter & K. M. Reiser (1990): Hydroxylation of collagen by lungs of rats administered bleomycin. —Am. J. Respir. Cell Mol. Biol., 2: 543–548.

[20] J. A. Last & K. M. Reiser (1989): Biosynthesis of collagen crosslinks. III. In vivo labeling and stability of lung collagen in rats with bleomycin-induced pulmonary fibrosis. —Am. J. Respir. Cell Mol. Biol., 1: 111–117.

[21] J. A. Last & K. M. Reiser (1986): Effects of silica on lung collagen. —Ciba Found. Symp., 121: 180–193.

[22] J. A. Last, L. G. Armstrong & K. M. Reiser (1990): Biosynthesis of collagen crosslinks. —Int. J. Biochem., 22: 559–564.

[23] A. di Donato, G. M. Ghiggeri, M. di Duca, E. Jivotenko, R. Acinni, J. Campolo, F. Ginevri & R. Gusmano (1997): Lysyl oxidase expression and collagen cross-linking during chronic adriamycin nephropathy. —Nephron, 76: 192–200.

[24] R. J. McCormick, T. I. Musch, B. C. Bergman & D. P. Thomas (1994): Regional differences in LV collagen accumulation and mature cross-linking after myocardial infarction in rats. —Am. J. Physiol., 266: H354–H359.

[25] W. H. Akeson, D. Amiel, G. L. Mechanic, S. L. Y. Woo, F. L. Harwood & M. L. Hamet (1977): Collagen cross-linking alterations in joint contractures: changes in the reducible cross-links in periarticular connective tissue collagen after nine weeks of immobilization. —Connect. Tissue Res., 5: 15–19.

[26] J. R. Spears, H. Zhan, S. Khurana, R. L. Karvonen & K. M. Reiser (1994): Modulation by β-aminopropionitrile of vessel luminal narrowing and structural abnormalities in arterial wall collagen in a rabbit model of conventional balloon angioplasty versus laser balloon angioplasty. —J. Clin. Invest., 93: 1543–1553.

[27] J. Brinckmann, Y. Acil, M. Tronnier, H. Notbohm, B. B ätge, W. Schmeller, M. H. J. Koch, P. K. Müller & H. Wolff (1996): Altered X-ray diffraction pattern is accompanied by a change in the mode of cross-link formation in lipodermatosclerosis. —J. Invest. Dermatol., 107: 589–592.

[28] T. Halme, J. Peltonen, T. J. Sims & T. Vihersaari & R. Penttinen (1986): Collagen in human aorta. Changes in the type III/I ratio and concentration of the reducible crosslink, dehydrohydroxylysinonorleucine in ascending aorta from healthy subjects of different age and patients with annulo-aortic ectasia. —Biochim. Biophys. Acta, 881: 222–228.

[29] S. Bazin, M. le Lous, V. C. Duance, T. J. Sims, A. J. Bailey, G. Gabbiani, G. d'Andiran, G. Pizzolato, A. Browski, C. Nicoletis & A. Delaunay (1980): Biochemistry and histology of the connective tissue of Dupuytren's disease lesions. —Eur. J. Clin. Invest., 10: 9–16.

[30] J. I. Harper, V. C. Duance, T. J. Sims & N. D. Light (1985): Lipoid proteinosis: an inherited disorder of collagen metabolism? —Br. J. Dermatol., 113: 145–151.

[31] B. Buckingham & K. M. Reiser (1990): Relationship between the content of lysyl oxidase-dependent crosslinks in skin collagen, nonenzymatic glycation, and long-term complications in type I diabetes mellitus. —J. Clin. Invest., 86: 1046–1054.

[32] K. M. Reiser, E. C. Crouch, K. Chang & J. R. Williamson (1991): Lysyl oxidase-mediated crosslinking in granulation tissue collagen in two models of hyperglycemia. —Biochim. Biophys. Acta, 1097: 55–61.

[33] S. Ricard-Blum, P. Esterre & J. A. Grimaud (1993): Collagen cross-linking by pyridinoline occurs in non-reversible skin fibrosis. —Cell Mol. Biol., 39: 723–727.

[34] S. Ricard-Blum, D. J. Hartmann & P. Esterre (1998): Monitoring of extracellular matrix metabolism and cross-linking in tissue, serum and urine of patients with chromoblastomycosis, a chronic skin fibrosis. —Eur. J. Clin. Invest., 28: 748–754.

[35] M. Lehto, T. J. Sims & A. J. Bailey (1985): Skeletal muscle injury—molecular changes in the collagen during healing. —Res. Exp. Med., 185: 95–106.

[36] J. E. Gerriets, S. L. Curwin & J. A. Last (1993): Tendon hypertrophy is associated with increased hydroxylation of nonhelical lysine residues at two specific cross-linking sites in type I collagen. —J. Biol. Chem., 286: 25553–25560.

[37] D. Herbage, O. Chevalier, H. Hassanein & B. Janin (1983): Collagen solubility and cross-linking in normal and fibrotic human livers. —Contr. Microbiol. Immunol., 7: 237–244.

[38] S. Ricard-Blum, S. Bresson-Hadni, D. A. Vuitton, G. Ville & J. A. Grimaud (1992): Hydroxypyridinium collagen cross-links in human liver fibrosis: study of alveolar echinococcosis. —Hepatology, 15: 599–602.

[39] S. Ricard-Blum, G. Ville & J. A. Grimaud (1992): Pyridinoline, a mature collagen cross-link, in fibrotic livers from Schistosoma mansoni-infected mice. —Am. J. Trop. Med. Hyg., 47: 816–820.

[40] S. Ricard-Blum, M. Liance, R. Houin, J. A. Grimaud & D. A. Vuitton (1995): Covalent cross-linking of liver collagen by pyridinoline increases in the course of experimental alveolar echinococcosis. —Parasite, 2: 113–118.

[41] S. Ricard-Blum, S. Bresson-Hadni, S. Guerret, P. Grenard, P. J. Volle, L. Risteli, J. A. Grimaud & D. A. Vuitton (1996): Mechanism of collagen network stabilization in human irreversible granulomatous liver fibrosis. —Gastroenterology, 111: 172–182.

[42] A. Hayasaka, S. IIda, N. Suzuki, F. Kondo, M. Miyazaki & H. Yonemitsu (1996): Pyridinoline collagen cross-links in patients with chronic viral hepatites and cirrhosis. —J. Hepatol., 24: 692–698.

[43] P. Grenard, B. Blanquier & S. Ricard-Blum (1997): Urinary excretion of the collagen cross-link pyridinoline increases during liver fibrosis. —J. Hepatol., 26: 1356–1362.

[44] S. Ricard-Blum, S. Bresson-Hadni, P. Grenard, P. Humbert, J. P. Carbillet, L. Risteli & D. A. Vuitton (1998): The level of the collagen cross-link pyridinoline reflects the improvement of cutaneous lesions in one case of skin alveolar echinococcosis. —Parasitol. Res., 84: 715–719.

---

What is claimed is:

1. A method for enhancing the degradability of collagen, said method comprising the step of modifying the collagen with at least one composition that selectively inhibits the activity or production of telopeptide lysyl hydroxylase.

2. The method of claim 1, wherein the telopeptide lysyl hydoxylase is according to the amino acid sequence described in at least one of SEQ ID NOS 8, 10 and 12.

3. The method of claim 1, the method further comprising the steps,
   maintaining a mammalian cell or tissue in an environment conducive to permitting the cell or tissue to synthesize and secrete collagen, wherein the synthesized and secreted collagen comprises telopeptides having at least one lysine,
   contacting the cell or tissue with an effective amount of at least one structural analogue of at least one compound selected from the group consisting of 2-oxoglutarate, anthracycline, coumalic acid, ascorbate, and minoxidil (2,4-diamino-6-piperidino-pyrimidine-3-oxide),
   continuing the maintaining of the cell or tissue in the presence of the at least one analogue, and
   assessing the degradability of the synthesized and secreted collagen.

4. The method of claim 3 wherein the cell or tissue has an enzyme having the amino acid sequence according to at least one of SEQ ID NOS 8, 10 and 12.

5. The method of claim 3, wherein the cell or tissue has an enzyme having at least 90% amino acid Identity to at least one of SEQ ID NOS 8, 10 and 12.

6. The method of claim 3, wherein the cell or tissue has an enzyme encoded by the polynucleotide sequence according to SEQ ID NOS 7, 9 and 11 or a polynucleotide sequence complementary thereto.

7. The method of claim 3 wherein the cell or tissue has an enzyme encoded by a polynucleotide sequence having at least 70% identity to the polynucleotide sequence of SEQ ID NOS 7, 9 and 11 or a polynucleotide sequence complementary thereto.

8. A method for enhancing the degradability of collagen, said method comprising the step of modifying the collagen with at least one composition that selectively inhibits the activity or production of telopeptide lysyl hydroxylase, the method further comprising the steps,
   maintaining a mammalian cell or tissue in an environment conducive to permitting the cell or tissue to synthesize and secrete collagen, wherein the synthesized and secreted collagen comprises telopeptides having at least one lysine,
   contacting the cell or tissue with an effective amount of at least one structural analogue of at least one compound selected from the group consisting of 2-oxoglutarate, anthracycline, coumalic acid, ascorbate, and minoxidil (2,4-diamino-6-piperidino-pyrimidine-3-oxide),
   continuing the maintaining of the cell or tissue in the presence of the at least one analogue, and
   assessing the degradability of the synthesized and secreted collagen.

\* \* \* \* \*

SEQUENCE LISTING

```
<160> NUMBER OF SEQ ID NOS: 16

<210> SEQ ID NO 1
<211> LENGTH: 210
<212> TYPE: DNA
<213> ORGANISM: Homo sapiens
<220> FEATURE:
<221> NAME/KEY: CDS
<222> LOCATION: (1)..(210)
<223> OTHER INFORMATION: /note="Sequence of human lysyl hydroxylase
      encoded by PLOD1"

<400> SEQUENCE: 1 atg cgg ccc ctg ctg cta ctg gcc ctg ctg ggc tgg ctg ctg ctg gcc      48
Met Arg Pro Leu Leu Leu Leu Ala Leu Leu Gly Trp Leu Leu Leu Ala
 1               5                  10                  15
```

```
gaa gcg aag ggc gac gcc aag ccg gag gac aac ctt tta gtc ctc acg        96
Glu Ala Lys Gly Asp Ala Lys Pro Glu Asp Asn Leu Leu Val Leu Thr
             20                  25                  30 gtg gcc act aag gag acc gag gga ttc cgt cgc ttc aag cgc tca gct       144
Val Ala Thr Lys Glu Thr Glu Gly Phe Arg Arg Phe Lys Arg Ser Ala
         35                  40                  45 cag ttc ttc aac tac aag atc cag gcg ctt ggc cta ggg gag gac tgg      192
Gln Phe Phe Asn Tyr Lys Ile Gln Ala Leu Gly Leu Gly Glu Asp Trp
     50                  55                  60 aat gtg gag aag ggg acg                                               210
Asn Val Glu Lys Gly Thr
 65                  70

<210> SEQ ID NO 2
<211> LENGTH: 70
<212> TYPE: PRT
<213> ORGANISM: Homo sapiens

<400> SEQUENCE: 2

Met Arg Pro Leu Leu Leu Ala Leu Leu Gly Trp Leu Leu Leu Ala
  1               5                  10                  15

Glu Ala Lys Gly Asp Ala Lys Pro Glu Asp Asn Leu Leu Val Leu Thr
             20                  25                  30

Val Ala Thr Lys Glu Thr Glu Gly Phe Arg Arg Phe Lys Arg Ser Ala
         35                  40                  45

Gln Phe Phe Asn Tyr Lys Ile Gln Ala Leu Gly Leu Gly Glu Asp Trp
     50                  55                  60

Asn Val Glu Lys Gly Thr
 65                  70

<210> SEQ ID NO 3
<211> LENGTH: 1422
<212> TYPE: DNA
<213> ORGANISM: Homo sapiens
<220> FEATURE:
<221> NAME/KEY: CDS
<222> LOCATION: (1)..(1422)
<223> OTHER INFORMATION: /note="Sequence of human lysyl hydroxylase
      encoded by PLOD1"

<400> SEQUENCE: 3 tcg gca ggt gga ggg cag aag gtc cgg ctg ctg aag aaa gct ctg gag        48
Ser Ala Gly Gly Gly Gln Lys Val Arg Leu Leu Lys Lys Ala Leu Glu
  1               5                  10                  15 aag cac gca gac aag gag gat ctg gtc att ctc ttc aca gac agc tat        96
Lys His Ala Asp Lys Glu Asp Leu Val Ile Leu Phe Thr Asp Ser Tyr
             20                  25                  30 gac gtg ctg ttt gca tcg ggg ccc cgg gag ctc ctg aag aag ttc cgg       144
Asp Val Leu Phe Ala Ser Gly Pro Arg Glu Leu Leu Lys Lys Phe Arg
         35                  40                  45 cag gcc agg agc cag gtg gtc ttc tct gct gag gag ctc atc tac cca       192
Gln Ala Arg Ser Gln Val Val Phe Ser Ala Glu Glu Leu Ile Tyr Pro
     50                  55                  60 gac cgc agg ctg gag acc aag tat ccg gtg gtg tcc gat ggc aag agg       240
Asp Arg Arg Leu Glu Thr Lys Tyr Pro Val Val Ser Asp Gly Lys Arg
 65                  70                  75                  80 ttc ctg ggc tct gga ggc ttc atc ggt tat gcc ccc aac ctc agc aaa       288
Phe Leu Gly Ser Gly Gly Phe Ile Gly Tyr Ala Pro Asn Leu Ser Lys
                 85                  90                  95 ctg gtg gcc gag tgg gag ggc cag gac agc gac agc gat cag ctg ttt       336
Leu Val Ala Glu Trp Glu Gly Gln Asp Ser Asp Ser Asp Gln Leu Phe
```

```
              100                 105                 110
tac acc aag atc ttc ttg gac ccg gag aag agg gag cag atc aat atc      384
Tyr Thr Lys Ile Phe Leu Asp Pro Glu Lys Arg Glu Gln Ile Asn Ile
        115                 120                 125 acc ctg gac cac cgc tgc cgt atc ttc cag aac ctg gat gga gcc ttg      432
Thr Leu Asp His Arg Cys Arg Ile Phe Gln Asn Leu Asp Gly Ala Leu
    130                 135                 140 gat gag gtc gtg ctc aag ttt gaa atg ggc cat gtg aga gcg agg aac      480
Asp Glu Val Val Leu Lys Phe Glu Met Gly His Val Arg Ala Arg Asn
145                 150                 155                 160 ctg gcc tat gac acc ctc ccg gtc ctg atc cat ggc aac ggg cca acc      528
Leu Ala Tyr Asp Thr Leu Pro Val Leu Ile His Gly Asn Gly Pro Thr
                165                 170                 175 aag ctg cag ttg aac tac ctg ggc aac tac atc ccg cgc ttc tgg acc      576
Lys Leu Gln Leu Asn Tyr Leu Gly Asn Tyr Ile Pro Arg Phe Trp Thr
            180                 185                 190 ttc gaa aca ggc tgc acc gtg tgt gac gaa ggc ttg cgc agc ctc aag      624
Phe Glu Thr Gly Cys Thr Val Cys Asp Glu Gly Leu Arg Ser Leu Lys
        195                 200                 205 ggc att ggg gat gaa gct ctg ccc acg gtc ctg gtc ggc gtg ttc atc      672
Gly Ile Gly Asp Glu Ala Leu Pro Thr Val Leu Val Gly Val Phe Ile
    210                 215                 220 gaa cag ccc acg ccg ttt gtg tcc ctg ttc ttc cag cgg ctc ctg cgg      720
Glu Gln Pro Thr Pro Phe Val Ser Leu Phe Phe Gln Arg Leu Leu Arg
225                 230                 235                 240 ctc cac tac ccc cag aaa cac atg cga ctt ttc atc cac aac cac gag      768
Leu His Tyr Pro Gln Lys His Met Arg Leu Phe Ile His Asn His Glu
                245                 250                 255 cag cac cac aag gct cag gtg gaa gag ttc ctg gca cag cat ggc agc      816
Gln His His Lys Ala Gln Val Glu Glu Phe Leu Ala Gln His Gly Ser
            260                 265                 270 gag tac cag tct gtg aag ctg gtg ggc cct gag gtg cgg atg gcg aat      864
Glu Tyr Gln Ser Val Lys Leu Val Gly Pro Glu Val Arg Met Ala Asn
        275                 280                 285 gca gat gcc agg aac atg ggc gca gac ctg tgc cgg cag gac cgc agc      912
Ala Asp Ala Arg Asn Met Gly Ala Asp Leu Cys Arg Gln Asp Arg Ser
    290                 295                 300 tgc acc tac tac ttc agc gtg gat gct gac gtg gcc ctg acc gag ccc      960
Cys Thr Tyr Tyr Phe Ser Val Asp Ala Asp Val Ala Leu Thr Glu Pro
305                 310                 315                 320 aac agc ctg cgg ctg ctg atc caa cag aac aag aat gtc att gcc ccg     1008
Asn Ser Leu Arg Leu Leu Ile Gln Gln Asn Lys Asn Val Ile Ala Pro
                325                 330                 335 ctg atg acc cgg cat ggg agg ctg tgg tcg aac ttc tgg ggg gct ctc     1056
Leu Met Thr Arg His Gly Arg Leu Trp Ser Asn Phe Trp Gly Ala Leu
            340                 345                 350 agt gca gat ggc tac tat gcc cgt tcc gag gac tac gtg gac att gtg     1104
Ser Ala Asp Gly Tyr Tyr Ala Arg Ser Glu Asp Tyr Val Asp Ile Val
        355                 360                 365 cag ggg cgg cgt gtt ggt gtc tgg aat gtg ccc tat att tca aac atc     1152
Gln Gly Arg Arg Val Gly Val Trp Asn Val Pro Tyr Ile Ser Asn Ile
    370                 375                 380 tac ttg atc aag ggc agt gcc ctg cgg ggt gag ctg cag tcc tca gat     1200
Tyr Leu Ile Lys Gly Ser Ala Leu Arg Gly Glu Leu Gln Ser Ser Asp
385                 390                 395                 400 ctc ttc cac cac agc aag ctg gac ccc gac atg gcc ttc tgt gcc aac     1248
Leu Phe His His Ser Lys Leu Asp Pro Asp Met Ala Phe Cys Ala Asn
                405                 410                 415 atc cgg cag cag gat gtg ttc atg ttc ctg acc aac cgg cac acc ctt     1296
```

-continued

```
Ile Arg Gln Gln Asp Val Phe Met Phe Leu Thr Asn Arg His Thr Leu
            420                 425                 430
ggc cat ctg ctc tcc cta gac agc tac cgc acc acc cac ctg cac aac      1344
Gly His Leu Leu Ser Leu Asp Ser Tyr Arg Thr Thr His Leu His Asn
            435                 440                 445
gac ctc tgg gag gtg ttc agc aac ccc gag gac tgg aag gag aag tac      1392
Asp Leu Trp Glu Val Phe Ser Asn Pro Glu Asp Trp Lys Glu Lys Tyr
450                 455                 460
atc cac cag aac tac acc aaa gcc ctg gca                              1422
Ile His Gln Asn Tyr Thr Lys Ala Leu Ala
465                 470
```

<210> SEQ ID NO 4
<211> LENGTH: 474
<212> TYPE: PRT
<213> ORGANISM: Homo sapiens

<400> SEQUENCE: 4

```
Ser Ala Gly Gly Gln Lys Val Arg Leu Leu Lys Ala Leu Glu
 1               5                  10                  15

Lys His Ala Asp Lys Glu Asp Leu Val Ile Leu Phe Thr Asp Ser Tyr
                20                  25                  30

Asp Val Leu Phe Ala Ser Gly Pro Arg Glu Leu Leu Lys Lys Phe Arg
            35                  40                  45

Gln Ala Arg Ser Gln Val Val Phe Ser Ala Glu Glu Leu Ile Tyr Pro
        50                  55                  60

Asp Arg Arg Leu Glu Thr Lys Tyr Pro Val Val Ser Asp Gly Lys Arg
65                  70                  75                  80

Phe Leu Gly Ser Gly Gly Phe Ile Gly Tyr Ala Pro Asn Leu Ser Lys
                85                  90                  95

Leu Val Ala Glu Trp Glu Gly Gln Asp Ser Asp Ser Asp Gln Leu Phe
            100                 105                 110

Tyr Thr Lys Ile Phe Leu Asp Pro Glu Lys Arg Glu Gln Ile Asn Ile
        115                 120                 125

Thr Leu Asp His Arg Cys Arg Ile Phe Gln Asn Leu Asp Gly Ala Leu
    130                 135                 140

Asp Glu Val Val Leu Lys Phe Glu Met Gly His Val Arg Ala Arg Asn
145                 150                 155                 160

Leu Ala Tyr Asp Thr Leu Pro Val Leu Ile His Gly Asn Gly Pro Thr
                165                 170                 175

Lys Leu Gln Leu Asn Tyr Leu Gly Asn Tyr Ile Pro Arg Phe Trp Thr
            180                 185                 190

Phe Glu Thr Gly Cys Thr Val Cys Asp Glu Gly Leu Arg Ser Leu Lys
        195                 200                 205

Gly Ile Gly Asp Glu Ala Leu Pro Thr Val Leu Val Gly Val Phe Ile
    210                 215                 220

Glu Gln Pro Thr Pro Phe Val Ser Leu Phe Phe Gln Arg Leu Leu Arg
225                 230                 235                 240

Leu His Tyr Pro Gln Lys His Met Arg Leu Phe Ile His Asn His Glu
                245                 250                 255

Gln His His Lys Ala Gln Val Glu Glu Phe Leu Ala Gln His Gly Ser
            260                 265                 270

Glu Tyr Gln Ser Val Lys Leu Val Gly Pro Glu Val Arg Met Ala Asn
        275                 280                 285

Ala Asp Ala Arg Asn Met Gly Ala Asp Leu Cys Arg Gln Asp Arg Ser
    290                 295                 300
```

```
Cys Thr Tyr Tyr Phe Ser Val Asp Ala Asp Val Ala Leu Thr Glu Pro
305                 310                 315                 320

Asn Ser Leu Arg Leu Leu Ile Gln Gln Asn Lys Asn Val Ile Ala Pro
            325                 330                 335

Leu Met Thr Arg His Gly Arg Leu Trp Ser Asn Phe Trp Gly Ala Leu
            340                 345                 350

Ser Ala Asp Gly Tyr Tyr Ala Arg Ser Glu Asp Tyr Val Asp Ile Val
            355                 360                 365

Gln Gly Arg Arg Val Gly Val Trp Asn Val Pro Tyr Ile Ser Asn Ile
370                 375                 380

Tyr Leu Ile Lys Gly Ser Ala Leu Arg Gly Glu Leu Gln Ser Ser Asp
385                 390                 395                 400

Leu Phe His His Ser Lys Leu Asp Pro Asp Met Ala Phe Cys Ala Asn
                405                 410                 415

Ile Arg Gln Gln Asp Val Phe Met Phe Leu Thr Asn Arg His Thr Leu
                420                 425                 430

Gly His Leu Leu Ser Leu Asp Ser Tyr Arg Thr Thr His Leu His Asn
            435                 440                 445

Asp Leu Trp Glu Val Phe Ser Asn Pro Glu Asp Trp Lys Glu Lys Tyr
        450                 455                 460

Ile His Gln Asn Tyr Thr Lys Ala Leu Ala
465                 470

<210> SEQ ID NO 5
<211> LENGTH: 549
<212> TYPE: DNA
<213> ORGANISM: Homo sapiens
<220> FEATURE:
<221> NAME/KEY: CDS
<222> LOCATION: (1)..(549)
<223> OTHER INFORMATION: /note="Sequence of human lysyl hydroxylase
      encoded by PLOD1"

<400> SEQUENCE: 5 ggg aag ctg gtg gag acg ccc tgc ccg gat gtc tat tgg ttc ccc atc      48
Gly Lys Leu Val Glu Thr Pro Cys Pro Asp Val Tyr Trp Phe Pro Ile
1               5                   10                  15 ttc acg gag gtg gcc tgt gat gag ctg gtg gag gag atg gag cac ttt      96
Phe Thr Glu Val Ala Cys Asp Glu Leu Val Glu Glu Met Glu His Phe
            20                  25                  30 ggc cag tgg tct ctg ggc aac aac aag gac aac cgc atc cag ggt ggc     144
Gly Gln Trp Ser Leu Gly Asn Asn Lys Asp Asn Arg Ile Gln Gly Gly
        35                  40                  45 tac gag aac gtg ccg act att gac atc cac atg aac cag atc ggc ttt     192
Tyr Glu Asn Val Pro Thr Ile Asp Ile His Met Asn Gln Ile Gly Phe
    50                  55                  60 gag cgg gag tgg cac aaa ttc ctg ctg gag tac att gcg ccc atg acg     240
Glu Arg Glu Trp His Lys Phe Leu Leu Glu Tyr Ile Ala Pro Met Thr
65                  70                  75                  80 gag aag ctc tac ccc ggc tac tac acc agg gcc cag ttt gac ctg gcc     288
Glu Lys Leu Tyr Pro Gly Tyr Tyr Thr Arg Ala Gln Phe Asp Leu Ala
                85                  90                  95 ttt gtc gtc cgc tac aag cct gat gag cag ccc tca ctg atg cca cac     336
Phe Val Val Arg Tyr Lys Pro Asp Glu Gln Pro Ser Leu Met Pro His
            100                 105                 110 cat gat gcc tcc acc ttc acc atc aac atc gcc ctg aac cga gtc ggg     384
His Asp Ala Ser Thr Phe Thr Ile Asn Ile Ala Leu Asn Arg Val Gly
        115                 120                 125
```

```
gtg gat tac gag ggc ggg ggc tgt cgg ttc ctg cgc tac aac tgt tcc      432
Val Asp Tyr Glu Gly Gly Gly Cys Arg Phe Leu Arg Tyr Asn Cys Ser
    130                 135                 140 atc cga gcc cca agg aag ggc tgg acc ctc atg cac cct gga cga ctc      480
Ile Arg Ala Pro Arg Lys Gly Trp Thr Leu Met His Pro Gly Arg Leu
145                 150                 155                 160 acg cat tac cat gag ggg ctc ccc acc acc agg ggc acc cgc tac atc      528
Thr His Tyr His Glu Gly Leu Pro Thr Thr Arg Gly Thr Arg Tyr Ile
                165                 170                 175 gca gtc tcc ttc gtc gat ccc                                          549
Ala Val Ser Phe Val Asp Pro
            180
```

<210> SEQ ID NO 6
<211> LENGTH: 183
<212> TYPE: PRT
<213> ORGANISM: Homo sapiens

<400> SEQUENCE: 6

```
Gly Lys Leu Val Glu Thr Pro Cys Pro Asp Val Tyr Trp Phe Pro Ile
 1               5                  10                  15

Phe Thr Glu Val Ala Cys Asp Glu Leu Val Glu Met Glu His Phe
                20                  25                  30

Gly Gln Trp Ser Leu Gly Asn Asn Lys Asp Asn Arg Ile Gln Gly Gly
            35                  40                  45

Tyr Glu Asn Val Pro Thr Ile Asp Ile His Met Asn Gln Ile Gly Phe
 50                  55                  60

Glu Arg Glu Trp His Lys Phe Leu Leu Glu Tyr Ile Ala Pro Met Thr
 65                  70                  75                  80

Glu Lys Leu Tyr Pro Gly Tyr Tyr Thr Arg Ala Gln Phe Asp Leu Ala
                85                  90                  95

Phe Val Arg Tyr Lys Pro Asp Glu Gln Pro Ser Leu Met Pro His
                100                 105                 110

His Asp Ala Ser Thr Phe Thr Ile Asn Ile Ala Leu Asn Arg Val Gly
            115                 120                 125

Val Asp Tyr Glu Gly Gly Gly Cys Arg Phe Leu Arg Tyr Asn Cys Ser
130                 135                 140

Ile Arg Ala Pro Arg Lys Gly Trp Thr Leu Met His Pro Gly Arg Leu
145                 150                 155                 160

Thr His Tyr His Glu Gly Leu Pro Thr Thr Arg Gly Thr Arg Tyr Ile
                165                 170                 175

Ala Val Ser Phe Val Asp Pro
            180
```

<210> SEQ ID NO 7
<211> LENGTH: 849
<212> TYPE: DNA
<213> ORGANISM: Homo sapiens
<220> FEATURE:
<221> NAME/KEY: CDS
<222> LOCATION: (1)..(849)
<223> OTHER INFORMATION: /note="Sequence of human lysyl hydroxylase encoded by PLOD2"

<400> SEQUENCE: 7

```
atg ggg gga tgc acg gtg aag cct cag ctg ctg ctc ctg gcg ctc gtc      48
Met Gly Gly Cys Thr Val Lys Pro Gln Leu Leu Leu Leu Ala Leu Val
 1               5                  10                  15 ctc cac ccc tgg aat ccc tgt ctg ggt gcg gac tcg gag aag ccc tcg      96
Leu His Pro Trp Asn Pro Cys Leu Gly Ala Asp Ser Glu Lys Pro Ser
```

-continued

```
                 20                  25                  30
agc atc ccc aca gat aaa tta tta gtc ata act gta gca aca aaa gaa      144
Ser Ile Pro Thr Asp Lys Leu Leu Val Ile Thr Val Ala Thr Lys Glu
             35                  40                  45 agt gat gga ttc cat cga ttt atg cag tca gcc aaa tat ttc aat tat      192
Ser Asp Gly Phe His Arg Phe Met Gln Ser Ala Lys Tyr Phe Asn Tyr
         50                  55                  60 act gtg aag gtc ctt ggt caa gga gaa gaa tgg aga ggt ggt gat gga      240
Thr Val Lys Val Leu Gly Gln Gly Glu Glu Trp Arg Gly Gly Asp Gly
 65                  70                  75                  80 att aat agt att gga ggg ggc cag aaa gtg aga tta atg aaa gaa gtc      288
Ile Asn Ser Ile Gly Gly Gly Gln Lys Val Arg Leu Met Lys Glu Val
                 85                  90                  95 atg gaa cac tat gct gat caa gat gat ctg gtt gtc atg ttt act gaa      336
Met Glu His Tyr Ala Asp Gln Asp Asp Leu Val Val Met Phe Thr Glu
            100                 105                 110 tgc ttt gat gtc ata ttt gct ggt ggt cca gaa gaa gtt cta aaa aaa      384
Cys Phe Asp Val Ile Phe Ala Gly Gly Pro Glu Glu Val Leu Lys Lys
        115                 120                 125 ttc caa aag gca aac cac aaa gtg gtc ttt gca gca gat gga att ttg      432
Phe Gln Lys Ala Asn His Lys Val Val Phe Ala Ala Asp Gly Ile Leu
130                 135                 140 tgg cca gat aaa aga cta gca gac aag tat cct gtt gtg cac att ggg      480
Trp Pro Asp Lys Arg Leu Ala Asp Lys Tyr Pro Val Val His Ile Gly
145                 150                 155                 160 aaa cgc tat ctg aat tca gga gga ttt att ggc tat gct cca tat gtc      528
Lys Arg Tyr Leu Asn Ser Gly Gly Phe Ile Gly Tyr Ala Pro Tyr Val
                165                 170                 175 aac cgt ata gtt caa caa tgg aat ctc cag gat aat gat gat gat cag      576
Asn Arg Ile Val Gln Gln Trp Asn Leu Gln Asp Asn Asp Asp Asp Gln
            180                 185                 190 ctc ttt tac act aaa gtt tac att gat cca ctg aaa agg gaa gct att      624
Leu Phe Tyr Thr Lys Val Tyr Ile Asp Pro Leu Lys Arg Glu Ala Ile
        195                 200                 205 aac atc aca ttg gat cac aaa tgc aaa att ttc cag acc tta aat gga      672
Asn Ile Thr Leu Asp His Lys Cys Lys Ile Phe Gln Thr Leu Asn Gly
    210                 215                 220 gct gta gat gaa gtt gtt tta aaa ttt gaa aat ggc aaa gcc aga gct      720
Ala Val Asp Glu Val Val Leu Lys Phe Glu Asn Gly Lys Ala Arg Ala
225                 230                 235                 240 aag aat aca ttt tat gaa aca tta cca gtg gca att aat gga aat gga      768
Lys Asn Thr Phe Tyr Glu Thr Leu Pro Val Ala Ile Asn Gly Asn Gly
                245                 250                 255 ccc acc aag att ctc ctg aat tat ttt gga aac tat gta ccc aat tca      816
Pro Thr Lys Ile Leu Leu Asn Tyr Phe Gly Asn Tyr Val Pro Asn Ser
            260                 265                 270 tgg aca cag gat aat ggc tgc act ctt tgt gaa                          849
Trp Thr Gln Asp Asn Gly Cys Thr Leu Cys Glu
        275                 280

<210> SEQ ID NO 8
<211> LENGTH: 283
<212> TYPE: PRT
<213> ORGANISM: Homo sapiens

<400> SEQUENCE: 8

Met Gly Gly Cys Thr Val Lys Pro Gln Leu Leu Leu Leu Ala Leu Val
 1               5                  10                  15

Leu His Pro Trp Asn Pro Cys Leu Gly Ala Asp Ser Glu Lys Pro Ser
                20                  25                  30
```

```
Ser Ile Pro Thr Asp Lys Leu Leu Val Ile Thr Val Ala Thr Lys Glu
             35                  40                  45

Ser Asp Gly Phe His Arg Phe Met Gln Ser Ala Lys Tyr Phe Asn Tyr
         50                  55                  60

Thr Val Lys Val Leu Gly Gln Gly Glu Glu Trp Arg Gly Gly Asp Gly
 65                  70                  75                  80

Ile Asn Ser Ile Gly Gly Gln Lys Val Arg Leu Met Lys Glu Val
                 85                  90                  95

Met Glu His Tyr Ala Asp Gln Asp Leu Val Val Met Phe Thr Glu
             100                 105                 110

Cys Phe Asp Val Ile Phe Ala Gly Gly Pro Glu Glu Val Leu Lys Lys
             115                 120                 125

Phe Gln Lys Ala Asn His Lys Val Val Phe Ala Ala Asp Gly Ile Leu
        130                 135                 140

Trp Pro Asp Lys Arg Leu Ala Asp Lys Tyr Pro Val Val His Ile Gly
145                 150                 155                 160

Lys Arg Tyr Leu Asn Ser Gly Gly Phe Ile Gly Tyr Ala Pro Tyr Val
                165                 170                 175

Asn Arg Ile Val Gln Gln Trp Asn Leu Gln Asp Asn Asp Asp Gln
             180                 185                 190

Leu Phe Tyr Thr Lys Val Tyr Ile Asp Pro Leu Lys Arg Glu Ala Ile
        195                 200                 205

Asn Ile Thr Leu Asp His Lys Cys Lys Ile Phe Gln Thr Leu Asn Gly
        210                 215                 220

Ala Val Asp Glu Val Val Leu Lys Phe Glu Asn Gly Lys Ala Arg Ala
225                 230                 235                 240

Lys Asn Thr Phe Tyr Glu Thr Leu Pro Val Ala Ile Asn Gly Asn Gly
                245                 250                 255

Pro Thr Lys Ile Leu Leu Asn Tyr Phe Gly Asn Tyr Val Pro Asn Ser
                260                 265                 270

Trp Thr Gln Asp Asn Gly Cys Thr Leu Cys Glu
        275                 280

<210> SEQ ID NO 9
<211> LENGTH: 810
<212> TYPE: DNA
<213> ORGANISM: Homo sapiens
<220> FEATURE:
<221> NAME/KEY: CDS
<222> LOCATION: (1)..(810)
<223> OTHER INFORMATION: /note="Sequence of human lysyl hydroxylase
      encoded by PLOD2"

<400> SEQUENCE: 9 gat aca gtc gac ttg tct gca gta gat gtc cat cca aac gta tca ata        48
Asp Thr Val Asp Leu Ser Ala Val Asp Val His Pro Asn Val Ser Ile
 1               5                  10                  15 ggt gtt ttt att gag caa cca acc cct ttt cta cct cgg ttt ctg gac        96
Gly Val Phe Ile Glu Gln Pro Thr Pro Phe Leu Pro Arg Phe Leu Asp
             20                  25                  30 ata ttg ttg aca ctg gat tac cca aaa gaa gca ctt aaa ctt ttt att       144
Ile Leu Leu Thr Leu Asp Tyr Pro Lys Glu Ala Leu Lys Leu Phe Ile
         35                  40                  45 cat aac aaa gaa gtt tat cat gaa aag gac atc aag gta ttt ttt gat       192
His Asn Lys Glu Val Tyr His Glu Lys Asp Ile Lys Val Phe Phe Asp
     50                  55                  60 aaa gct aag cat gaa atc aaa act ata aaa ata gta gga cca gaa gaa       240
```

-continued

```
Lys Ala Lys His Glu Ile Lys Thr Ile Lys Ile Val Gly Pro Glu Glu
 65                  70                  75                  80 aat cta agt caa gcg gaa gcc aga aac atg gga atg gac ttt tgc cgt    288
Asn Leu Ser Gln Ala Glu Ala Arg Asn Met Gly Met Asp Phe Cys Arg
                 85                  90                  95 cag gat gaa aag tgt gat tat tac ttt agt gtg gat gca gat gtt gtt    336
Gln Asp Glu Lys Cys Asp Tyr Tyr Phe Ser Val Asp Ala Asp Val Val
            100                 105                 110 ttg aca aat cca agg act tta aaa att ttg att gaa caa aac aga aag    384
Leu Thr Asn Pro Arg Thr Leu Lys Ile Leu Ile Glu Gln Asn Arg Lys
        115                 120                 125 atc att gct cct ctt gta act cgt cat gga aag ctg tgg tcc aat ttc    432
Ile Ile Ala Pro Leu Val Thr Arg His Gly Lys Leu Trp Ser Asn Phe
    130                 135                 140 tgg gga gca ttg agt cct gat gga tac tat gca cga tct gaa gat tat    480
Trp Gly Ala Leu Ser Pro Asp Gly Tyr Tyr Ala Arg Ser Glu Asp Tyr
145                 150                 155                 160 gtg gat att gtt caa ggg aat aga gta gga gta tgg aat gtc cca tat    528
Val Asp Ile Val Gln Gly Asn Arg Val Gly Val Trp Asn Val Pro Tyr
                165                 170                 175 atg gct aat gtg tac tta att aaa gga aag aca ctc cga tca gag atg    576
Met Ala Asn Val Tyr Leu Ile Lys Gly Lys Thr Leu Arg Ser Glu Met
            180                 185                 190 aat gaa agg aac tat ttt gtt cgt gat aaa ctg gat cct gat atg gct    624
Asn Glu Arg Asn Tyr Phe Val Arg Asp Lys Leu Asp Pro Asp Met Ala
        195                 200                 205 ctt tgc cga aat gct aga gaa atg ggt gta ttt atg tac att tct aat    672
Leu Cys Arg Asn Ala Arg Glu Met Gly Val Phe Met Tyr Ile Ser Asn
    210                 215                 220 aga cat gaa ttt gga agg cta tta tcc act gct aat tac aat act tcc    720
Arg His Glu Phe Gly Arg Leu Leu Ser Thr Ala Asn Tyr Asn Thr Ser
225                 230                 235                 240 cat tat aac aat gac ctc tgg cag att ttt gaa aat cct gtg gac tgg    768
His Tyr Asn Asn Asp Leu Trp Gln Ile Phe Glu Asn Pro Val Asp Trp
                245                 250                 255 aag gaa aag tat ata aac cgt gat tat tca aag att ttc act            810
Lys Glu Lys Tyr Ile Asn Arg Asp Tyr Ser Lys Ile Phe Thr
            260                 265                 270
```

<210> SEQ ID NO 10
<211> LENGTH: 270
<212> TYPE: PRT
<213> ORGANISM: Homo sapiens

<400> SEQUENCE: 10

```
Asp Thr Val Asp Leu Ser Ala Val Asp Val His Pro Asn Val Ser Ile
  1               5                  10                  15

Gly Val Phe Ile Glu Gln Pro Thr Pro Phe Leu Pro Arg Phe Leu Asp
                 20                  25                  30

Ile Leu Leu Thr Leu Asp Tyr Pro Lys Glu Ala Leu Lys Leu Phe Ile
            35                  40                  45

His Asn Lys Glu Val Tyr His Glu Lys Asp Ile Lys Val Phe Phe Asp
        50                  55                  60

Lys Ala Lys His Glu Ile Lys Thr Ile Lys Ile Val Gly Pro Glu Glu
 65                  70                  75                  80

Asn Leu Ser Gln Ala Glu Ala Arg Asn Met Gly Met Asp Phe Cys Arg
                 85                  90                  95

Gln Asp Glu Lys Cys Asp Tyr Tyr Phe Ser Val Asp Ala Asp Val Val
            100                 105                 110
```

```
Leu Thr Asn Pro Arg Thr Leu Lys Ile Leu Ile Glu Gln Asn Arg Lys
        115                 120                 125

Ile Ile Ala Pro Leu Val Thr Arg His Gly Lys Leu Trp Ser Asn Phe
    130                 135                 140

Trp Gly Ala Leu Ser Pro Asp Gly Tyr Tyr Ala Arg Ser Glu Asp Tyr
145                 150                 155                 160

Val Asp Ile Val Gln Gly Asn Arg Val Gly Val Trp Asn Val Pro Tyr
                165                 170                 175

Met Ala Asn Val Tyr Leu Ile Lys Gly Lys Thr Leu Arg Ser Glu Met
            180                 185                 190

Asn Glu Arg Asn Tyr Phe Val Arg Asp Lys Leu Asp Pro Asp Met Ala
        195                 200                 205

Leu Cys Arg Asn Ala Arg Glu Met Gly Val Phe Met Tyr Ile Ser Asn
    210                 215                 220

Arg His Glu Phe Gly Arg Leu Leu Ser Thr Ala Asn Tyr Asn Thr Ser
225                 230                 235                 240

His Tyr Asn Asn Asp Leu Trp Gln Ile Phe Glu Asn Pro Val Asp Trp
                245                 250                 255

Lys Glu Lys Tyr Ile Asn Arg Asp Tyr Ser Lys Ile Phe Thr
            260                 265                 270

<210> SEQ ID NO 11
<211> LENGTH: 549
<212> TYPE: DNA
<213> ORGANISM: Homo sapiens
<220> FEATURE:
<221> NAME/KEY: CDS
<222> LOCATION: (1)..(549)
<223> OTHER INFORMATION: /note="Sequence of human lysyl hydroxylase
      encoded by PLOD2"

<400> SEQUENCE: 11 gaa aat ata gtt gaa cag ccc tgt cca gat gtc ttt tgg ttc ccc ata      48
Glu Asn Ile Val Glu Gln Pro Cys Pro Asp Val Phe Trp Phe Pro Ile
  1               5                  10                  15 ttt tct gaa aaa gcc tgt gat gaa ttg gta gaa gaa atg gaa cat tac      96
Phe Ser Glu Lys Ala Cys Asp Glu Leu Val Glu Glu Met Glu His Tyr
             20                  25                  30 ggc aaa tgg tct ggg gga aaa cat cat gat agc cgt ata tct ggt ggt     144
Gly Lys Trp Ser Gly Gly Lys His His Asp Ser Arg Ile Ser Gly Gly
         35                  40                  45 tat gaa aat gtc cca act gat gat atc cac atg aag caa gtt gat ctg     192
Tyr Glu Asn Val Pro Thr Asp Asp Ile His Met Lys Gln Val Asp Leu
     50                  55                  60 gag aat gta tgg ctt gat ttt atc cgg gag ttc att gca cca gtt aca     240
Glu Asn Val Trp Leu Asp Phe Ile Arg Glu Phe Ile Ala Pro Val Thr
 65                  70                  75                  80 ctg aag gtc ttt gca ggc tat tat acg aag gga ttt gca cta ctg aat     288
Leu Lys Val Phe Ala Gly Tyr Tyr Thr Lys Gly Phe Ala Leu Leu Asn
                 85                  90                  95 ttt gta gta aaa tac tcc cct gaa cga cag cgt tct ctt cgt cct cat     336
Phe Val Val Lys Tyr Ser Pro Glu Arg Gln Arg Ser Leu Arg Pro His
            100                 105                 110 cat gat gct tct aca ttt acc ata aac att gca ctt aat aac gtg gga     384
His Asp Ala Ser Thr Phe Thr Ile Asn Ile Ala Leu Asn Asn Val Gly
        115                 120                 125 gaa gac ttt cag gga ggt ggt tgc aaa ttt cta agg tac aat tgc tct     432
Glu Asp Phe Gln Gly Gly Gly Cys Lys Phe Leu Arg Tyr Asn Cys Ser
    130                 135                 140
```

-continued

```
att gag tca cca cga aaa ggc tgg agc ttc atg cat cct ggg aga ctc      480
Ile Glu Ser Pro Arg Lys Gly Trp Ser Phe Met His Pro Gly Arg Leu
145                 150                 155                 160 aca cat ttg cat gaa gga ctt cct gtt aaa aat gga aca aga tac att      528
Thr His Leu His Glu Gly Leu Pro Val Lys Asn Gly Thr Arg Tyr Ile
                165                 170                 175 gca gtg tca ttt ata gat ccc                                          549
Ala Val Ser Phe Ile Asp Pro
            180
```

<210> SEQ ID NO 12
<211> LENGTH: 183
<212> TYPE: PRT
<213> ORGANISM: Homo sapiens

<400> SEQUENCE: 12

```
Glu Asn Ile Val Glu Gln Pro Cys Pro Asp Val Phe Trp Phe Pro Ile
1               5                   10                  15

Phe Ser Glu Lys Ala Cys Asp Glu Leu Val Glu Glu Met Glu His Tyr
                20                  25                  30

Gly Lys Trp Ser Gly Gly Lys His His Asp Ser Arg Ile Ser Gly Gly
            35                  40                  45

Tyr Glu Asn Val Pro Thr Asp Asp Ile His Met Lys Gln Val Asp Leu
        50                  55                  60

Glu Asn Val Trp Leu Asp Phe Ile Arg Glu Phe Ile Ala Pro Val Thr
65                  70                  75                  80

Leu Lys Val Phe Ala Gly Tyr Tyr Thr Lys Gly Phe Ala Leu Leu Asn
                85                  90                  95

Phe Val Val Lys Tyr Ser Pro Glu Arg Gln Arg Ser Leu Arg Pro His
                100                 105                 110

His Asp Ala Ser Thr Phe Thr Ile Asn Ile Ala Leu Asn Asn Val Gly
            115                 120                 125

Glu Asp Phe Gln Gly Gly Gly Cys Lys Phe Leu Arg Tyr Asn Cys Ser
        130                 135                 140

Ile Glu Ser Pro Arg Lys Gly Trp Ser Phe Met His Pro Gly Arg Leu
145                 150                 155                 160

Thr His Leu His Glu Gly Leu Pro Val Lys Asn Gly Thr Arg Tyr Ile
                165                 170                 175

Ala Val Ser Phe Ile Asp Pro
            180
```

<210> SEQ ID NO 13
<211> LENGTH: 849
<212> TYPE: DNA
<213> ORGANISM: Homo sapiens
<220> FEATURE:
<221> NAME/KEY: CDS
<222> LOCATION: (1)..(849)
<223> OTHER INFORMATION: /note="Sequence of human lysyl hydroxylase encoded by PLOD3"

<400> SEQUENCE: 13

```
atg acc tcc tcg ggg cct gga ccc cgg ttc ctg ctg ctg ctg ccg ctg      48
Met Thr Ser Ser Gly Pro Gly Pro Arg Phe Leu Leu Leu Leu Pro Leu
1               5                   10                  15 ctg ctg ccc cct gcg gcc tca gcc tcc gac cgg ccc cgg ggc cga gac      96
Leu Leu Pro Pro Ala Ala Ser Ala Ser Asp Arg Pro Arg Gly Arg Asp
                20                  25                  30 ccg gtc aac cca gag aag ctg ctg gtg atc act gtg gcc aca gct gaa     144
```

```
Pro Val Asn Pro Glu Lys Leu Leu Val Ile Thr Val Ala Thr Ala Glu
            35                  40                  45 acc gag ggg tac ctg cgt ttc ctg cgc tct gcg gag ttc ttc aac tac      192
Thr Glu Gly Tyr Leu Arg Phe Leu Arg Ser Ala Glu Phe Phe Asn Tyr
        50                  55                  60 act gtg cgg acc ctg ggc ctg gga gag gag tgg cga ggg ggt gat gtg      240
Thr Val Arg Thr Leu Gly Leu Gly Glu Glu Trp Arg Gly Gly Asp Val
65                  70                  75                  80 gct cga aca gtt ggt gga gga cag aag gtc cgg tgg tta aag aag gaa      288
Ala Arg Thr Val Gly Gly Gly Gln Lys Val Arg Trp Leu Lys Lys Glu
                85                  90                  95 atg gag aaa tac gct gac cgg gag gat atg atc atc atg ttt gtg gat      336
Met Glu Lys Tyr Ala Asp Arg Glu Asp Met Ile Ile Met Phe Val Asp
            100                 105                 110 agc tac gac gtg att ctg gcc ggc agc ccc aca gag ctg ctg aag aag      384
Ser Tyr Asp Val Ile Leu Ala Gly Ser Pro Thr Glu Leu Leu Lys Lys
        115                 120                 125 ttc gtc cag agt ggc agc cgc ctg ctc ttc tct gca gag agc ttc tgc      432
Phe Val Gln Ser Gly Ser Arg Leu Leu Phe Ser Ala Glu Ser Phe Cys
130                 135                 140 tgg ccc gag tgg ggg ctg gcg gag cag tac cct gag gtg ggc acg ggg      480
Trp Pro Glu Trp Gly Leu Ala Glu Gln Tyr Pro Glu Val Gly Thr Gly
145                 150                 155                 160 aag cgc ttc ctc aat tct ggt gga ttc atc ggt ttt gcc acc acc atc      528
Lys Arg Phe Leu Asn Ser Gly Gly Phe Ile Gly Phe Ala Thr Thr Ile
                165                 170                 175 cac caa atc gtg cgc cag tgg aag tac aag gat gat gac gac gac cag      576
His Gln Ile Val Arg Gln Trp Lys Tyr Lys Asp Asp Asp Asp Asp Gln
            180                 185                 190 ctg ttc tac aca cgg ctc tac ctg gac cca gga ctg agg gag aaa ctc      624
Leu Phe Tyr Thr Arg Leu Tyr Leu Asp Pro Gly Leu Arg Glu Lys Leu
        195                 200                 205 agc ctt aat ctg gat cat aag tct cgg atc ttt cag aac ctc aac ggg      672
Ser Leu Asn Leu Asp His Lys Ser Arg Ile Phe Gln Asn Leu Asn Gly
210                 215                 220 gct tta gat gaa gtg gtt tta aag ttt gat cgg aac cgt gtg cgt atc      720
Ala Leu Asp Glu Val Val Leu Lys Phe Asp Arg Asn Arg Val Arg Ile
225                 230                 235                 240 cgg aac gtg gcc tac gac acg ctc ccc att gtg gtc cat gga aac ggt      768
Arg Asn Val Ala Tyr Asp Thr Leu Pro Ile Val Val His Gly Asn Gly
                245                 250                 255 ccc act aag ctg cag ctc aac tac ctg gga aac tac gtc ccc aat ggc      816
Pro Thr Lys Leu Gln Leu Asn Tyr Leu Gly Asn Tyr Val Pro Asn Gly
            260                 265                 270 tgg act cct gag gga ggc tgt ggc ttc tgc aac                          849
Trp Thr Pro Glu Gly Gly Cys Gly Phe Cys Asn
        275                 280

<210> SEQ ID NO 14
<211> LENGTH: 283
<212> TYPE: PRT
<213> ORGANISM: Homo sapiens

<400> SEQUENCE: 14

Met Thr Ser Ser Gly Pro Gly Pro Arg Phe Leu Leu Leu Leu Pro Leu
1               5                   10                  15

Leu Leu Pro Pro Ala Ala Ser Ala Ser Asp Arg Pro Arg Gly Arg Asp
            20                  25                  30

Pro Val Asn Pro Glu Lys Leu Leu Val Ile Thr Val Ala Thr Ala Glu
        35                  40                  45
```

```
Thr Glu Gly Tyr Leu Arg Phe Leu Arg Ser Ala Glu Phe Phe Asn Tyr
 50                  55                  60

Thr Val Arg Thr Leu Gly Leu Gly Glu Trp Arg Gly Gly Asp Val
 65              70                  75                  80

Ala Arg Thr Val Gly Gly Gln Lys Val Arg Trp Leu Lys Lys Glu
                85                  90                  95

Met Glu Lys Tyr Ala Asp Arg Glu Asp Met Ile Ile Met Phe Val Asp
            100                 105                 110

Ser Tyr Asp Val Ile Leu Ala Gly Ser Pro Thr Glu Leu Leu Lys Lys
        115                 120                 125

Phe Val Gln Ser Gly Ser Arg Leu Leu Phe Ser Ala Glu Ser Phe Cys
130                 135                 140

Trp Pro Glu Trp Gly Leu Ala Glu Gln Tyr Pro Glu Val Gly Thr Gly
145                 150                 155                 160

Lys Arg Phe Leu Asn Ser Gly Gly Phe Ile Gly Phe Ala Thr Thr Ile
                165                 170                 175

His Gln Ile Val Arg Gln Trp Lys Tyr Lys Asp Asp Asp Asp Gln
            180                 185                 190

Leu Phe Tyr Thr Arg Leu Tyr Leu Asp Pro Gly Leu Arg Glu Lys Leu
        195                 200                 205

Ser Leu Asn Leu Asp His Lys Ser Arg Ile Phe Gln Asn Leu Asn Gly
210                 215                 220

Ala Leu Asp Glu Val Val Leu Lys Phe Asp Arg Asn Arg Val Arg Ile
225                 230                 235                 240

Arg Asn Val Ala Tyr Asp Thr Leu Pro Ile Val Val His Gly Asn Gly
                245                 250                 255

Pro Thr Lys Leu Gln Leu Asn Tyr Leu Gly Asn Tyr Val Pro Asn Gly
            260                 265                 270

Trp Thr Pro Glu Gly Gly Cys Gly Phe Cys Asn
        275                 280

<210> SEQ ID NO 15
<211> LENGTH: 1362
<212> TYPE: DNA
<213> ORGANISM: Homo sapiens
<220> FEATURE:
<221> NAME/KEY: CDS
<222> LOCATION: (1)..(1362)
<223> OTHER INFORMATION: /note="Sequence of human lysyl hydroxylase
      encoded by PLOD3"

<400> SEQUENCE: 15 gac cgg agg aca ctc ccg ggg ggg cag cct ccc ccc cgg gtg ttt ctg       48
Asp Arg Arg Thr Leu Pro Gly Gly Gln Pro Pro Pro Arg Val Phe Leu
 1               5                  10                  15 gcc gtg ttt gtg gaa cag cct act ccg ttt ctg ccc cgc ttc ctg cag      96
Ala Val Phe Val Glu Gln Pro Thr Pro Phe Leu Pro Arg Phe Leu Gln
                20                  25                  30 cgg ctg cta ctc ctg gac tat ccc ccc gac agg gtc acc ctt ttc ctg     144
Arg Leu Leu Leu Leu Asp Tyr Pro Pro Asp Arg Val Thr Leu Phe Leu
            35                  40                  45 cac aac aac gag gtc ttc cat gaa ccc cac atc gct gac tcc tgg ccg     192
His Asn Asn Glu Val Phe His Glu Pro His Ile Ala Asp Ser Trp Pro
 50                  55                  60 cag ctc cag gac cac ttc tca gct gtg aag ctc gtg ggg ccg gag gag     240
Gln Leu Gln Asp His Phe Ser Ala Val Lys Leu Val Gly Pro Glu Glu
 65                  70                  75                  80
```

| | | |
|---|---|---|
| gct ctg agc cca ggc gag gcc agg gac atg gcc atg gac ctg tgt cgg<br>Ala Leu Ser Pro Gly Glu Ala Arg Asp Met Ala Met Asp Leu Cys Arg<br>                    85                    90                    95 | 288 |
| cag gac ccc gag tgt gag ttc tac ttc agc ctg gac gcc gac gct gtc<br>Gln Asp Pro Glu Cys Glu Phe Tyr Phe Ser Leu Asp Ala Asp Ala Val<br>            100                    105                    110 | 336 |
| ctc acc aac ctg cag acc ctg cgt atc ctc att gag gag aac agg aag<br>Leu Thr Asn Leu Gln Thr Leu Arg Ile Leu Ile Glu Glu Asn Arg Lys<br>                115                    120                    125 | 384 |
| gtg atc gcc ccc atg ctg tcc cgc cac ggc aag ctg tgg tcc aac ttc<br>Val Ile Ala Pro Met Leu Ser Arg His Gly Lys Leu Trp Ser Asn Phe<br>130                    135                    140 | 432 |
| tgg ggc gcc ctg agc ccc gat gag tac tac gcc cgc tcc gag gac tac<br>Trp Gly Ala Leu Ser Pro Asp Glu Tyr Tyr Ala Arg Ser Glu Asp Tyr<br>145                    150                    155                    160 | 480 |
| gtg gag ctg gtg cag cgg aag cga gtg ggt gtg tgg aat gta cca tac<br>Val Glu Leu Val Gln Arg Lys Arg Val Gly Val Trp Asn Val Pro Tyr<br>                165                    170                    175 | 528 |
| atc tcc cag gcc tat gtg atc cgg ggt gat acc ctg cgg atg gag ctg<br>Ile Ser Gln Ala Tyr Val Ile Arg Gly Asp Thr Leu Arg Met Glu Leu<br>            180                    185                    190 | 576 |
| ccc cag agg gat gtg ttc tcg ggc agt gac aca gac ccg gac atg gcc<br>Pro Gln Arg Asp Val Phe Ser Gly Ser Asp Thr Asp Pro Asp Met Ala<br>                195                    200                    205 | 624 |
| ttc tgt aag agc ttt cga gac aag ggc atc ttc ctc cat ctg agc aat<br>Phe Cys Lys Ser Phe Arg Asp Lys Gly Ile Phe Leu His Leu Ser Asn<br>210                    215                    220 | 672 |
| cag cat gaa ttt ggc cgg ctc ctg gcc act tcc aga tac gac acg gag<br>Gln His Glu Phe Gly Arg Leu Leu Ala Thr Ser Arg Tyr Asp Thr Glu<br>225                    230                    235                    240 | 720 |
| cac ctg cac ccc gac ctc tgg cag atc ttc gac aac ccc gtc gac tgg<br>His Leu His Pro Asp Leu Trp Gln Ile Phe Asp Asn Pro Val Asp Trp<br>                245                    250                    255 | 768 |
| aag gag cag tac atc cac gag aac tac agc cgg gcc ctg gaa ggg gaa<br>Lys Glu Gln Tyr Ile His Glu Asn Tyr Ser Arg Ala Leu Glu Gly Glu<br>            260                    265                    270 | 816 |
| gga atc gtg gag cag cca tgc ccg gac gtg tac tgg ttc cca ctg ctg<br>Gly Ile Val Glu Gln Pro Cys Pro Asp Val Tyr Trp Phe Pro Leu Leu<br>                275                    280                    285 | 864 |
| tca gaa caa atg tgt gat gag ctg gtg gca gag atg gag cac tac ggc<br>Ser Glu Gln Met Cys Asp Glu Leu Val Ala Glu Met Glu His Tyr Gly<br>290                      295                    300 | 912 |
| cag tgg tca ggc ggc cgg cat gag gat tca agg ctg gct gga ggc tac<br>Gln Trp Ser Gly Gly Arg His Glu Asp Ser Arg Leu Ala Gly Gly Tyr<br>305                    310                    315                    320 | 960 |
| gag aat gtg ccc acc gtg gac atc cac atg aag cag gtg ggg tac gag<br>Glu Asn Val Pro Thr Val Asp Ile His Met Lys Gln Val Gly Tyr Glu<br>                325                    330                    335 | 1008 |
| gac cag tgg ctg cag ctg ctg cgg acg tat gtg ggc ccc atg acc gag<br>Asp Gln Trp Leu Gln Leu Leu Arg Thr Tyr Val Gly Pro Met Thr Glu<br>            340                    345                    350 | 1056 |
| agc ctg ttt ccc ggt tac cac acc aag gcg cgg gcg gtg atg aac ttt<br>Ser Leu Phe Pro Gly Tyr His Thr Lys Ala Arg Ala Val Met Asn Phe<br>                355                    360                    365 | 1104 |
| gtg gtt cgc tac cgg cca gac gag cag ccg tct ctg cgg cca cac cac<br>Val Val Arg Tyr Arg Pro Asp Glu Gln Pro Ser Leu Arg Pro His His<br>370                    375                    380 | 1152 |
| gac tca tcc acc ttc acc ctc aac gtt gcc ctc aac cac aag ggc ctg<br>Asp Ser Ser Thr Phe Thr Leu Asn Val Ala Leu Asn His Lys Gly Leu<br>385                    390                    395                    400 | 1200 |

```
gac tat gag gga ggt ggc tgc cgc ttc ctg cgc tac gac tgt gtg atc      1248
Asp Tyr Glu Gly Gly Gly Cys Arg Phe Leu Arg Tyr Asp Cys Val Ile
            405                 410                 415 tcc tcc ccg agg aag ggc tgg gca ctc ctg cac ccc ggc cgc ctc acc      1296
Ser Ser Pro Arg Lys Gly Trp Ala Leu Leu His Pro Gly Arg Leu Thr
        420                 425                 430 cac tac cac gag ggg ctg cca acg acc tgg ggc aca cgc tac atc atg      1344
His Tyr His Glu Gly Leu Pro Thr Thr Trp Gly Thr Arg Tyr Ile Met
    435                 440                 445 gtg tcc ttt gtc gac ccc                                              1362
Val Ser Phe Val Asp Pro
450

<210> SEQ ID NO 16
<211> LENGTH: 454
<212> TYPE: PRT
<213> ORGANISM: Homo sapiens

<400> SEQUENCE: 16

Asp Arg Arg Thr Leu Pro Gly Gly Gln Pro Pro Arg Val Phe Leu
  1               5                  10                  15

Ala Val Phe Val Glu Gln Pro Thr Pro Phe Leu Pro Arg Phe Leu Gln
                 20                  25                  30

Arg Leu Leu Leu Asp Tyr Pro Pro Asp Arg Val Thr Leu Phe Leu
             35                  40                  45

His Asn Asn Glu Val Phe His Glu Pro His Ile Ala Asp Ser Trp Pro
         50                  55                  60

Gln Leu Gln Asp His Phe Ser Ala Val Lys Leu Val Gly Pro Glu Glu
 65                  70                  75                  80

Ala Leu Ser Pro Gly Glu Ala Arg Asp Met Ala Met Asp Leu Cys Arg
                 85                  90                  95

Gln Asp Pro Glu Cys Glu Phe Tyr Phe Ser Leu Asp Ala Asp Ala Val
                100                 105                 110

Leu Thr Asn Leu Gln Thr Leu Arg Ile Leu Ile Glu Glu Asn Arg Lys
            115                 120                 125

Val Ile Ala Pro Met Leu Ser Arg His Gly Lys Leu Trp Ser Asn Phe
        130                 135                 140

Trp Gly Ala Leu Ser Pro Asp Glu Tyr Tyr Ala Arg Ser Glu Asp Tyr
145                 150                 155                 160

Val Glu Leu Val Gln Arg Lys Arg Val Gly Val Trp Asn Val Pro Tyr
                165                 170                 175

Ile Ser Gln Ala Tyr Val Ile Arg Gly Asp Thr Leu Arg Met Glu Leu
            180                 185                 190

Pro Gln Arg Asp Val Phe Ser Gly Ser Asp Thr Asp Pro Asp Met Ala
        195                 200                 205

Phe Cys Lys Ser Phe Arg Asp Lys Gly Ile Phe Leu His Leu Ser Asn
    210                 215                 220

Gln His Glu Phe Gly Arg Leu Leu Ala Thr Ser Arg Tyr Asp Thr Glu
225                 230                 235                 240

His Leu His Pro Asp Leu Trp Gln Ile Phe Asp Asn Pro Val Asp Trp
                245                 250                 255

Lys Glu Gln Tyr Ile His Glu Asn Tyr Ser Arg Ala Leu Glu Gly Glu
            260                 265                 270

Gly Ile Val Glu Gln Pro Cys Pro Asp Val Tyr Trp Phe Pro Leu Leu
        275                 280                 285
```

-continued

```
Ser Glu Gln Met Cys Asp Glu Leu Val Ala Glu Met Glu His Tyr Gly
    290                 295                 300
Gln Trp Ser Gly Gly Arg His Glu Asp Ser Arg Leu Ala Gly Gly Tyr
305                 310                 315                 320
Glu Asn Val Pro Thr Val Asp Ile His Met Lys Gln Val Gly Tyr Glu
                325                 330                 335
Asp Gln Trp Leu Gln Leu Leu Arg Thr Tyr Val Gly Pro Met Thr Glu
                340                 345                 350
Ser Leu Phe Pro Gly Tyr His Thr Lys Ala Arg Ala Val Met Asn Phe
                355                 360                 365
Val Val Arg Tyr Arg Pro Asp Glu Gln Pro Ser Leu Arg Pro His His
    370                 375                 380
Asp Ser Ser Thr Phe Thr Leu Asn Val Ala Leu Asn His Lys Gly Leu
385                 390                 395                 400
Asp Tyr Glu Gly Gly Gly Cys Arg Phe Leu Arg Tyr Asp Cys Val Ile
                405                 410                 415
Ser Ser Pro Arg Lys Gly Trp Ala Leu Leu His Pro Gly Arg Leu Thr
                420                 425                 430
His Tyr His Glu Gly Leu Pro Thr Thr Trp Gly Thr Arg Tyr Ile Met
                435                 440                 445
Val Ser Phe Val Asp Pro
450
```